US006683059B1

(12) United States Patent
Hung et al.

(10) Patent No.: US 6,683,059 B1
(45) Date of Patent: Jan. 27, 2004

(54) MINI-E1A GENE AND GENE PRODUCTS

(75) Inventors: Mien-Chie Hung, Houston, TX (US); Hua Chen, Houston, TX (US); Dihua Yu, Houston, TX (US); Ralph Wilfred Paul, Seattle, WA (US); Aaron Garth Loomis, Seattle, WA (US); Daniel Nathan Andrew LaFoc, Seattle, WA (US)

(73) Assignee: Board of Regents, The University of Texas System, Austin, TX (US)

( * ) Notice: Subject to any disclaimer, the term of this patent is extended or adjusted under 35 U.S.C. 154(b) by 286 days.

(21) Appl. No.: 09/718,865

(22) Filed: Nov. 21, 2000

Related U.S. Application Data

(63) Continuation of application No. 08/945,424, filed as application No. PCT/US97/19042 on Oct. 20, 1997, now Pat. No. 6,197,754, which is a continuation-in-part of application No. 08/730,910, filed on Oct. 18, 1996.

(51) Int. Cl.$^7$ .................. A01N 43/04; A01N 63/00; A61K 48/00; A61K 31/70; C12N 15/00

(52) U.S. Cl. .................. 514/44; 435/320.1; 435/325; 424/93.21

(58) Field of Search .................. 514/44; 424/93.1; 435/325, 320.1

(56) References Cited

U.S. PATENT DOCUMENTS

| | | | |
|---|---|---|---|
| 4,394,448 A | 7/1983 | Szoka, Jr. et al. | 435/172 |
| 4,920,211 A | 4/1990 | Tibbetts et al. | 536/27 |
| 5,516,631 A | 5/1996 | Frisch | 435/5 |
| 5,578,482 A | 11/1996 | Lippman et al. | 435/240.1 |
| 5,641,484 A | 6/1997 | Hung | |
| 5,643,567 A | 7/1997 | Hung | |
| 5,677,178 A | 10/1997 | McCormick | 435/325 |
| 5,776,743 A | 7/1998 | Frisch | |
| 5,801,029 A | 9/1998 | McCormick | 435/172.3 |
| 5,846,945 A | 12/1998 | McCormick | 514/44 |
| 5,851,818 A | 12/1998 | Huang et al. | 435/320.1 |
| 5,856,181 A | 1/1999 | McCormick | 435/325 |
| 5,972,706 A | 10/1999 | McCormick | 435/440 |
| 6,197,754 B1 * | 3/2001 | Hung et al. | 514/44 |
| 6,326,356 B1 * | 12/2001 | Hung et al. | 514/44 |

FOREIGN PATENT DOCUMENTS

| | | |
|---|---|---|
| WO | WO 90/15595 | 12/1990 |
| WO | WO 93/03769 | 3/1993 |
| WO | WO 94/18992 | 9/1994 |
| WO | WO 94/21115 | 9/1994 |
| WO | WO 95/16051 | 6/1995 |
| WO | WO 96/07322 | 3/1996 |
| WO | WO 97/30732 | 8/1997 |

OTHER PUBLICATIONS

Barbacid, "ras Genes," *Ann. Rev. Biochem.* 56:779–827, 1987.

Bargmann & Weinberg, "Increased Tyrosine Kinase Activity Associated with the Protein Encoded by the Activated neu Oncogene," *Proc. Natl. Acad. Sci. USA*, 85:5394–5398, 1988.

Bargmann, et al., "Multiple Independent Activations of the neu Oncogene by a Point Mutation Altering the Transmembrane Domain of p185," *Cell*, 45:649–657, 1986.

Bargmann, et al., "The neu Oncogene Encodes an Epidermal Growth Factor Receptor–Related Protein," *Nature*, 319:226–230, 1986.

Berk and Sharp, "Structure and the Adenovirus 2 Earyl mRNAs," *Cell*, 14:695–711, 1978.

Berk, "Adenovirus Promoters and E1A Transsativation," *Ann. Rev. Genet.*, 20:45–79, 1986.

Brunet and Burk "Concentration Dependence of Transcriptional Transactivation in Inducible E1A–Containing Human Cells," *Mol. Cell. Bio.*, 8(11):4799–4807, 1988.

Buchman, et al., Appendix A: "The SV40 Nucleotide Sequence," In Molecular Biology of Tumor Viruses, Part 2, 2nd. Edition, ed. J. Tooze, 799–813, 1980.

Chan, et al., "Selective Inhibition of the Growth of Ras–Transformed Human Bronchial Epithelial Cells by Emodin, A Protein–Tyrosine Kinase Inhibitor," *Biochemical and Biophysical Research Communications*, 193(3), 1152–58, 1993.

Chang, et al., "Inhibition of Intratracheal Lung Cancer Development by Systemic Delivery of E1A," *Oncogene* 13:1405–12, 1996.

Chang, et al., "Adeno–Associated Virus P5 Promoter Contains an Adenovirus E1A–Inducible Element and a Binding Site for the Major Late Transcription Factor," *Journal of Virology*, 63(8):3479–88, 1989.

Cook and Lewis, "Differential NK Cell Cell and Macrophage Killing of Hamster Cells Infected with Nononcogenic or Oncogenic Adenovirus," *Science*, 224:612–15, 1984.

Cook, et al., "Role of Tumor Necrosis Factor–α in E1A Oncogene–Induced Susceptibility of Neoplastic Cells to Lysis by Natural Killer Cells and Activated Macrophages," *The Journal of Immunology*, 142(12):4527–34, 1989.

(List continued on next page.)

*Primary Examiner*—Deborah Crouch
(74) *Attorney, Agent, or Firm*—Fulbright & Jaworski L.L.P.

(57) ABSTRACT

The present invention provides methods and compositions for the suppression of oncogenic transformation, tumorigenesis and metastasis. The present invention discloses functional domains of E1A responsible for the suppression of transformation, and provides mini-E1A constructs that can be used for tumor suppression. The invention also discloses methods for the novel use of mini-E1A in combination with chemotherapeutic drugs and/or tyrosine kinase inhibitors.

28 Claims, 16 Drawing Sheets

OTHER PUBLICATIONS

Corbeil and Branton, "Functional Importance of Complex Formation between the Retinoblastoma Tumor Suppressor Family and Adenovirus E1A Proteins as Determined by Mutational Analysis of E1A Conserved Region 2," *Journal of Virology*, 68(10):6697–6709, 1994.

Coussens, et al., "Tyrosine Kinase Receptor with Extensive Homology to EGF Receptor Shares Chromosomal Location with neu Oncogene," *Science*, 230:1132–1139, 1985.

DeCaprio, et al., "S V40 Large Tumor Forms a Specific Complex with the Product of the Retinoblastoma Susceptibility Gene," *Cell*, 54:275–283, 1988.

Dobashi, et al., "Characterization of a neu/c–erbB–2 Protein–Specific Activating Factor," *Proc. Natl. Acad. Sci. USA*, 88:8582–86, 1991.

Dougall, et al., "The neu–Oncogene: Signal Transduction Pathways, Transformation Mechanisms and Evolving Therapies," *Oncogene*, 9:2109–23, 1994.

Douglas, et al., "Modulation of Transformation of Primary Epithelial Cells by the Second Exon of the Ad5 E1A12S Gene," *Oncogene*, 6:2093–2103, 1991.

Downward, et al., "Close Similarity of Epidermal Growth Factor Receptor and v–erb–B Oncogene Protein Sequences," *Nature*, 307:521–527, 1984.

Earp, et al., "Heterodimerization and Functional Interaction Between EGF Receptor Family Members: A New SignalingParadigm with Implications for Breast Cancer Eeserach," *Breast Cancer Research and Treatment*, 35:115–32, 1995.

Edlund, et al., "Cell–Specific Expression of the Rat Insulin Gene: Evidence for Role of Two Distinct 5' Flanking Elements," *Science*, 230:912–16, 1985.

Egan, et al., "Transformation by Oncogenes Encoding Protein Kinases Induces the Metastatic Phenotype," *Science*, 238:202–205, 1987.

Evan, et al., "Induction of Apoptosis in Fibroblasts by c–myc Protein," *Cell*, 69:119–28, 1992.

Felgner and Rhodes, "Gene Therapeutics: The Direct Delivery of Purified Genes in vivo and Their Application as Drugs, Without the Use of Retroviruses, Is Discussed," *Nature*, 349:351–52, 1991.

Felgner and Ringold "Cationic Liposome–Mediated Transfection," *Nature*, 337:387–88, 1989.

Figge and Smith, "Cell–Division Sequence Motif," *Nature*, 334:198, 1988.

Figge, et al., Prediction of Similar Transforming Regions in Simian Virus 40 Large T, Adenovirus E1A, and myc Oncoproteins, *Journal of Virology*, 62:(5)1814–18, 1988.

Flint and Shenk, "Adenovirus E1A Protein Paradigm Viral Transactivator," *Annu. Rev. Genet.*, 23:141–61, 1989.

Freedman and Shin, "Use of Nude Mice for Studies on the Tumorigenicity of Animal Cells," The Nude Mouse in Experimental and Clinical Research, Fogh and Gavinella, eds., Academic Press, pp. 354–384, 1978.

Frisch, et al., "Adenovirus E1A Represses Protease Expression and Inhibits Metastasis of Human Tumor Cells," *Oncogene*, 5:75–83, 1990.

Frisch, "Antioncogenic Effect of Adenovirus E1A in Human Tumor Cells," *Proc. Natl. Acad. Sci. USA*, 88:9077–81, 1991.

Fung, et al., "Activation of the Cellular Oncogene c–erbB by LTR Insertion: Molecular Basis for Induction of Erythroblastosis by Avian Leukosis Virus," *Cell*, 33:357–68, 1983.

Gao, X., and Huang, L., A Novel Cationic Liposome Reagent for Efficient Transfection of Mammalian Cells, *Biochemical and Biophysical Research Communication*, 179:(1)280–85, 1991.

Gazit, et al., "Chemo–Adoptive Immunotherapy of Nude Mice Implanted with Human Colorectal Carcinoma and Melanoma Cell Lines," *Cancer Immunology Immunotherapy*, 35:135–44, 1992.

Griffin, et al., "Sequence and Analysis of Polyoma Virus DNA," Molecular Biology of Tumor Viruses, 2nd Edition, Part 2, ed. J. Tooze, 831–846, 1980.

Haley, et al., "Transformation Properties of Type 5 Adenovirus Mutants that Differentially Express the E1A Gene Products," *Proc. Natl. Acad. Sci. USA*, 81:5734–38, 1984.

Harlow, et al., "Monoclonal Antibodies Specific for Adenovirus Early Region 1A Proteins: Extensive Heterogeneity in Early Region 1A Products," *J. of Virology*, 55(3):533–46, 1985.

Hearing, et al., "Sequence–Independent Autoregulation of the Adenovirus Type 5 E1A Transcription Unit," *Mol. Cell. Bio.*, 5(11):3214–21, 1985.

Holmes, et al., "Identification of Heregulin, a Specific Activator of p185erB2", *Science*, 256:1205–10, 1992.

Horikoshi, et al., "Two Domains of p53 Interact with the TATA–Binding Protein, and the Adenovirus 13S E1A Protein Disrupts the Association, Relieving p53–Mediated Transcriptional Repression," *Molecular and Cellular Biology*, 15(1):227–34, 1995.

Houweling, et al., "Partial Transformation of Primary Rat Cells by the Leftmost 4.5% Fragment of Adenovirus 5 DNA," *J. Virology*, 105:537–50, 1980.

Huang and Huang, "Purification and Characterization of the neu/erb B2 Ligand–Growth Factor from Bovine Kidney," *The Journal of Biological Chemistry*, 267(16):11508–12, 1992.

Hudziak, et al., "Amplified Expression of the HER2/ERBB2 Oncogene Induces Resistance to Tumor Necrosis Factor $\alpha$ in NIH 3T3 Cells," *Proc. Natl. Acad. Sci. USA*, 85:5102–06, 1988.

Hung, et al., "Molecular Cloning of the neu Gene: Absence of Gross Structural Alteration in Oncogenic Alleles," *Proc. Natl. Acad. Sci. USA*, 83:261–64, 1986.

Hung, "The neu Proto–Oncogene and Breast Cancer," *Cancer Bull.*, 40(5):300–303, 1988.

Hung, et al., "Amplification of the Proto–neu Oncogene Activation by a Single Point Mutation," *Proc. Natl. Acad. Sci. USA*, 86:2545–48, 1989.

Hung, et al., "Transcriptional Repression of the HER–2/neu Protooncogene by Transforming Oncogenes from DNA Tumor Virus," *Proc. AM. Assoc. Cancer Res., 81st Annual Meeting*, 31:13, Mar. 1990.

Hung, et al., "Aberrant Expression of the c–erbB–2/neu Protooncogene in Ovarian Cancer," *Cancer Letters*, 61:95–103, 1992.

Hung, et al., "HER–2/neu–Targeting Gene Therapy—A Review," *Gene*, 159:65–17, 1995.

Inoue, et al., "Consideration of Simultaneous Combination Chemotherapy—Employing a Sensitivity Test in Dunn Osteosarcoma and NR Fibrosarcoma by Intra–Test Tube Contact of Tumor Cell Suspension, and Subcutaneous Inoculation–," *J. Jpn. Soc. Cancer Ther.* 25(12):2781–89, 1990.

Jayasuriya, et al., "Emodin, A Protein Tyrosine Kinase Inhibitor from Polygonum Cuspidatum," *Journal of Natural Products*, 55(5):696–98, 1992.

Jelsma, et al, "Use of Deletion and Point Mutants Spanning the Coding Region of the Adenovirus 5 E1A Gene to Define a Domain That is Essential for Transcriptional Activation," *Virology*, 164:494–502, 1988.

Jelsma, et al., "Sequences in E1A Proteins of Human Adenovirus 5 Required for Cell Transformation, Repression of a Transcriptional Enhacer, and Induction of Proliferating Cell Nuclear Antigen," *Virology*, 171:120–30, 1989.

Johnson, et al., "Epidermal Growth Factor Receptor Gene Promoter," *The Journal of Biological Chemistry*, 263(12) 5693–99, 1988.

Kalderon and Smith, In Vitro Mutagenesis of a Putative DNA Binding Domain of SV40 Large–T, *Virology*, 139:109–37, 1984.

Karlsson, et al., "Stable Gene Transfer and Tissue–Specific Expression of a Human Globin Gene Using Adenoviral Vectors," *The EMBO Journal*, 5(9):2377–85, 1986.

Kiyokawa, et al., "Cell Cycle–Dependent Regulation of p18$^{neu}$: A Relationship Between Disruption of This Regulation and Transformation," *Proc. Natl. Acad. Sci. USA*, 92:1092–96, 1995.

Kraus, et al., "Overexpression of the EGF Receptor–Related Proto–Oncogene erbB–2 in Human Mammary Tumor Cells Lines by Different Molecular Mechanisms," *EMBO J.*, 6(3):605–10, 1987.

Kuppuswamy and Chinnadurai, "Relationship Between the Transforming and Transcriptional Regulatory Functions of Adenovirus 2 E1a Oncogene," *Virology*, 159:31–8, 1987.

Land, et al., "Tumorigenic Conversion of Primary Embryo Fibroblasts Requires at Least Two Cooperating Oncogenes," *Nature* 304:596–602, 1983.

Land, et al., "Cellular Oncogenes and Multistep Carcinogenesis," *Science*, 222:771–76, 1983.

Lehväslaiho, et al., "A Chimeric EGF–R–neu Proto–Oncogene Allows EGF to Regulate neu Tyrosine Kinase and Cell Transformation," *EMBO Journal*, 8:(1)159–66, 1989.

Leiberger, et al., "Expression of Exogenous DNA in Rat Liver Cells afte Liposome–Mediated Transfection in vivo," *Biochemical and Biophysical Research Communications*, 174:(3)1223–31, 1991.

Lillie, et al., "An Adenovirus E1a Protein Region Required for Transformation and Transcriptional Repression," *Cell*, 46:1043–51, 1986.

Liu and Green, "Promoter Targeting by Adenovirus E1a Through Interaction with Different Cellular DNA–binding Domains," *Nature*, 368:520–25, 1994.

Lupu, et al., "Direct Interaction of a Ligand for the erbB2 Oncogene Product with the EGF Receptor and p185$^{erbB2}$," *Science*, 249:1552–54, 1990.

Matin and Hung, "Negative Regulation of the Neu Promoter by the SV40 Large T Antigen," *Cell Growth & Differentiation*, 4:1051–56, 1993.

Matin, "Regulation of neu gene expression by the simian virus 40 large T antigen and tumor suppressors Rb and p53," *Diss. Abstr. Int. B*, 54(5):2365, 1993. Abstract only.

McGrath, et al., "Structure and Organization of the Human Ki–ras Proto–Oncogene and a Related Processed Pseudogene," *Nature*,304:501–06, 1983.

Mitchell and Tjian, "Transcriptional Regulation in Mammalian Cells by Sequence–Specific DNA Binding Proteins," *Science*, 245:371–78, 1989.

Montell, et al., "Complete Transformation by Adenovirus 2 Requires Both E1A Proteins," *Cell*, 36:951–61, 1984.

Moran, et al., "Lytic and Transforming Functions of Individual Products of the Adenovirus E1A Gene," *Journal of Virology*, 57(3):765–75, 1986.

Moran, et al., "Multiple Functional Domains in the Adenovirus E1A Gene," *Cell*, 48:177–78 1987.

Müller, et al., "Differential Expression of Cellular Oncogenes During Pre–and Postnatal Development of the Mouse," *Nature*, 299:640–44, 1982.

Nabel, et al., "Site–Specific Gene Expression in Vivo by Direct Gene Transfer into the Arterial Wall," *Science*, 249:1285–88, 1990.

Nelson, et al., "E1a–Dependent Expression of Adenovirus Genes in OTF963 Embryonal Carcinoma Cells: Role of E1a–Induced Differentiation," *Proc. Natl. Acad. Sci. USA*, 87:8041–45, 1990.

Nicolau, et al., Liposomes as Carriers for Gene Transfer in Vivo, *Biology Cell*, 47:121–130, 1983.

Nicolua, et al., Liposomes as Carriers for in Vivo Gene Transfer and Expression, *Methods in Enzymology*, 149:157–177, 1987.

Nicolau, et al., "Liposomes for Gene Transfer and Expression in Vivo," *Colloids and Surfaces*, 14:325–37, 1985.

Offringa, et al., "A Novel Function of the Transforming Domain of E1a: Repression of AP–1 Activity," *Cell*, 62:527–38, 1990.

Peles, et al, "Isolation of the Neu/HER–2 Stimulatory Ligand: A 44 kd Glycoprotein That Induces Differentiation of Mammary Tumor Cells," *Cell* 69:205–16, 1992.

Pozzatti, et al., "Primary Rat Embryo Cells Transformed by One or Two Oncogenes Show Different Metastatic Potentials," *Science*, 232:223–27, 1986.

Pozzatti, et al., "The E1a Gene of Adenovirus Type 2 Reduces the Metastatic Potential of ras–Transformed Rat Embryo Cells," *Mol. Cell Biol.*, 8(7):2984–88, 1988.

Rao, et al., "The Adenovirus E1A Proteins Induce Apoptosis, Which Is Inhibited by the E1B 19–kDa and Bcl2 Proteins," *Proc. Natl. Acad. Sci. USA*, 89:7742–46, 1992.

Roberts, et al., "Individual Adenovirus Type 5 Early Region 1A Gene Products Elicit Distinct Alterations of Cellular Morphology and Gene Expression," *Journal of Virology*, 56(2):404–13, 1985.

Ruley, "Adenovirus Early Region 1A Enables Viral and Cellular Transforming Genes to Transform Primary Cells in Culture," *Nature*, 304:602–06, 1983.

Rustgi, et al., "Amino–Terminal Domains of c–myc and N–myc Proteins Mediate Binding to the Retinoblastoma Ggene Product," *Nature*, 352:541–44, 1991.

Sanchez–Prieto, et al., "Human and Murine Carcinoma Cell Lines Become Sensitive to DNA–Damaging Agents by Expression of the E1a Gene." *Cancer Therapy 2*, Suppl. 1, S26, 1995.

Sanchez–Prieto, et al., "Carcinoma Cell Lines Become Sensitive to DNA–Damaging Agents by the Expression of the Adenovirus E1A Gene," *Oncogene*, 13:1083–92, 1996.

Sassone–Corsi & Borrelli, "Promoter Trans–Activation of Protooncogenes c–fos and c–myc, but not c–Hs–ras, by Products of Adenovirus Early Region 1A," *Proc. Natl. Acad. Sci. USA*, 84:6430–33, 1987.

Sawada, et al., "Tumorigenicity of Adenovirus–Transformed Cells: Region E1A of Adenovirus 12 Confers Resistance to Natural Killer Cells", *Virology*, 147:413–21, 1985.

Schechter, et al., "The neu Oncogene: An erb–B–Related Gene Encoding a 185,000–M, Tumour Antigen," *Nature*, 312:513–16, 1984.

Schechter, et al., "The neu Gene: An erbB–Homologous Gene Distinct from and Unlinked to the Gene Encoding the EGF Receptor," *Science*, 229:976–78, 1985.

Schneider, et al., "Mutational Analysis of the Adenovirus E1a Gene: The Role of Transcriptional Regulation in Transformation," *The EMBO Journal*, 6(7):2053–60, 1987.

Semba, et al., "A v–erbB–Related Protooncogene, c–erbB–2, Is Distinct from the c–erbB–1/Epidermal Growth Factor–Receptor Gene and Is Amplified in a Human Salivary Gland Adenocarcinoma," *Proc. Natl. Acad. Sci. USA*, 82:6497–501, 1985.

Senear and Lewis, "Morphological Transformation of Established Rodent Cell Lines by High–Level Expression of the Adenovirus Type 2 E1a Gene," *Mol. Cell. Bio.*, 6(4):1253–60, 1986.

Shih, et al., "Transforming Genes of Carcinomas and Neuroblastomas Introduced into Mouse Fibroblasts," *Nature* 290:261–64, 1981.

Shin, "Use of Nude Mice for Tumorigenicity Testing and Mass Propagation," *Methods in Enzymology*, 58:370–379, 1979.

Slamon, et al., "Human Breast Cancer: Correlation of Relapse and Survival with Amplification of the HER–2/neu Oncogene," *Science*, 235:177–181, 1987.

Slamon, et al., "Studies of the HER–2/neu Proto–Oncogene in Human Breast and Ovarian Cancer," *Science*, 244:707–12, 1989.

Smith & Ziff, "The Amino–Terminal Region of the Adenovirus Serotype 5 E1a Protein Performs Two Separate Functions when Expressed in Primary Baby Rat Kidney Cells," *Mol. Cell. Biol.*, 8(9):3882–90, 1988.

Steeg, et al., "Altered Expression of NM22, a Gene Associated with Low Tumor Metastatic Potential, during Adenovirus 2 E1a Inhibition of Experimental Metastasis," *Cancer Res.*, 48:6550–54, 1988.

Stern, et al., "p185, a Product of the neu Proto–Oncogene, Is a Receptorlike Protein Associated with Tyrosine Kinase Activity," *Mol. Cell. Biol*, 6(5):1729–40, 1986.

Suen, et al., "Transcriptional Regulation of neuOncogene," *Breast Cancer Research and Treatment*, 14(1):Abstract 213, 1989.

Suen and Hung, "Multiple cis–and trans–Acting Elements Involved in Regulation of the neu Gene," *Molecular and Cellular Biology*, 10:(12)6306–15, 1990.

Suen and Hung, "c–myc Reverses neu–Induced Transformed Morphology by Transcriptional Repression," *Molecular and Cellular Biology*, 11(1):354–62, 1991.

Teramota, et al., "Serum Enzyme Immunoassay Kit for the Detection of c–erbB–2 Oncoprotein," Annual AACI Meeting, Abstract #1446, 1991.

Tsai, et al., "Correlation of Intrinsic Chemoresistance of Non–Small–Cell Lung Cancer Cell Lines with HER–2/neu Gene Expression but Not with ras Gene Mutations," *Journal of the National Cancer Institute*, 85(11):897–901, 1993.

Tsai et al., "Enhanced Chemoresistance by Elevation of p185$^{neu}$ Levels in HER–2/neu–Transfected Human Lung Cancer Cells," *Journal of the National Cancer Institute*, 87(9):682–84, 1995.

Tzeng, et al., "Breast Cancer Formation in Transgenic Animals Induced by the Whey Acidic Protein SV40 T Antigen (WAP–SV–T) Hybrid Gene," *Oncogene* 8:1965–71, 1993.

Vousden and Jat, "Functional Similarity between HPV16 E7, SV40 Large T and Adenovirus E1a Proteins," *Oncogene*, 4:153–58, 1989.

Wallich, et al., "Abrogation of Metastatic Properties of Tumour Cells by de novo Expression of H–2K Antigens Following H–2 Gene Transfection," *Nature*, 315:301–05, 1985.

Wang, et al., "E1A Induces Phosphorylation of the Retinoblastoma Protein Independently of Direct Physical Association between the E1A and Retinoblastoma Products," *Molecular and Cellular Biology*, 11(8):4253–65, 1991.

Weinberg, R.A., "The Action of Oncogenes in the Cytoplasm and Nucleus," *Science*, 230:770–76. 1985.

Whyte, et al., "Association between an Oncogene and an Anti–Oncogene: The Adenovirus E1A Proteins Bind to the Retinoblastoma Gene Product," *Nature*, 334:124–29, 1988.

Whyte, et al., "Two Regions of the Adenovirus Early Region 1A Proteins Are Required for Transformation," *J. Virol.*, 62(1):257–65, 1988.

Whyte, et al., "Cellular Targets for Transformation by the Adenovirus E1A Proteins," *Cell*, 56:67–75, 1989.

Wolff, et al., Differential Effects of the Simian Virus 40 Early Genes on Mammary Epithelial Cell Growth, Morphology, and Gene Expression, *Experimental Cell Research*, 202:67–76, 1992.

Xie and Hung, "Nuclear Localization of p185$^{NEU}$ Tyrosine Kinase and Its Association with Transcriptional Transactivation," *Biochemical and Biophysical Research Communications*, 203(3):1589–98, 1994.

Yamamoto, et al., "Similarity of Protein Encoded by the Human c–erb–B–2 Gene to Epidermal Growth Factor Receptor," *Nature*, 319:230–32, 1986.

Yarden and Weinberg, "Experimental Approaches to Hypothetical Hormones: Detection of a Candidate Ligand of the neu Protooncogene," *Proc. Natl. Acad. Sci. USA*, 86:3179–83, 1989.

Yarden and Peles, "Biochemical Analysis of the Ligand for the ne Oncogenic Receptor," *Biochemistry*, 30:3543–50, 1991.

Yeh, et al., "Effects of Anthraquinones of *Polygonum cuspidatum* on HL–60 Cells," *Planta medica*, 413–14, 1988.

Yu, et al., "Transcriptional Repression of the neu Protooncogene by the Adenovirus 5 E1A Gene Products," *Proc. Natl. Acad. Sci. USA*, 87:4499–503, 1990.

Yu, et al., "Adenovirus Type 5 E1A Gene Products Act as Transformation Suppressors of the neu Oncogene," *Mol. Cell. Bio.*, 11(3):1745–1750, 1991.

Yu, et al., "Expression of Activated Rat neu Is Sufficient to Induce Experimental Metastasis in 3T3 Cells," *Oncogene* 5:1991–96, 1991.

Yu, et al., "Mechanisms of c–erbB2/neu Oncogene Induced Metastasis and Repression of Metastatic Properties by Adenovirus 5 E1A Gene Products," *Oncogene* 7:2263–70, 1992.

Yu, et al., "The Retinoblastoma Gene Product Suppresses neu Oncogene–induced Transformation via Transcriptional Repression of neu," *The Journal of Biological Chemistry*, 267(15):10203–206, 1992.

Yu, et al., "Enhanced c–erbB–2/neu Expression in Human Ovarian Cancer Cells Correlates with More Severe Malignancy That Can Be Suppressed by E1A," *Cancer Research*, 53:891–98, 1993.

Yu, et al., "Liposome–mediated in vivo E1A Gene Transfer Suppressed Dissemination of Ovarian Cancer Cells that Overexpress HER–2/neu," *Oncogene* 11:1383–88, 1995.

Xing, et al., "Mutant SV40 Large T Antigen As A Therapeutic Agent for HER–2/neu–Overexpressing Ovarian Cancer", *Cancer Gene Therapy*, 3(3):168–74, 1996.

Zerler, et al., "Adenovirus E1A Coding Sequences that Enable ras and pmt Oncogenes to Transform Cultured Primary Cells," *Molecular and Cellular Biology*, 6(3):887–99, 1986.

Zerler, et al., "Different Functional Domains of the Adenovirus E1A Gene and Involved in Regulation of Host Cell Cycle Products," *Molecula and Cellular Biology*, 7(2):821–29, 1987.

Zhang, et al., "Amplification and Rearrangement of c–erb B Proto–Oncogenes in Cancer of Human Female Genital Tract," *Oncogene*, 4:985–89, 1989.

Zhang, et al., "HER–2/neu–Targeting Cancer Therapy via Adenovirus–Mediated E1A Delivery in an Animal Model," *Oncogene*, 10:1947–54, 1995.

Zhau, et al., "Amplification and Expression of the c–erbB–2/neu Proto–Oncogene in Human Bladder Cancer," Chemical Abstracts, 114(21):205–Abstract No. 114;200732Z, 1991.

Zhou, et al., "A Retrovirus Vector which Transducers a Functional Estrogen Receptor Gene at High Efficiency," *Mol. Endocrinology*, 3(7):1157–64, 1989.

Ames et al., "Induction of sensitivity to the cytotoxic action of tumor necrosis factor alpha by adenovirus E1A is independent of transformation and transcriptional activation," *J. Virol.*, 64(9): 4115–4122, 1990.

Barbeau, et al., "Functional interactions within adenovirus E1A protein complexes," *Oncogene*, 9:359–373, 1994.

Leclere et al., "Comparison between E1A gene from oncogenic and non–oncogenic adenoviruses in cellular transformation (Ad E1A conserved region)," *Arch. Virol.*, 132:343–357, 1993.

Chen et al., "Mapping of adenovirus 5 E1A domains responsible for suppression of neu–mediated transformation via transcriptional repression of neu," *Oncogene*, 14:1965–1971, 1997.

Fattaey et al., "Independent regions of adenovirus E1A are required for binding to and dissociation of E2F–protein complexes," *Mol. Cell. Biol.*, 13(12):7267–7277, 1993.

Mymryk, "Tumor suppressive properties of the adenovirus 5 E1A oncogene," *Oncogene*, 13:1581–1589, 1996.

Zhang and Hung, "Sensitization of HER–2/neu–overexpressing non–small cell lung cancer cells to chemotherapeutic drugs by tyrosine inhibitor emodin," *Oncogene*, 12:571–576, 1996.

\* cited by examiner

MINI-E1A GENE AND GENE PRODUCTS

This application is a continuation of application Ser. No. 08/945,424, filed Oct. 20, 1997. Application Ser. No. 08/945,424 is the U.S. National Phase of PCT/US97/19042, which is a continuation-in-part of U.S. patent application Ser. No. 08/730,910 filed Oct. 18, 1996. The entire text of each of the above-referenced disclosures is specifically incorporated herein by reference without disclaimer.

FIELD OF THE INVENTION

The present invention relates to methodology and associated genetic constructs for the suppression of oncogenic transformation, tumorigenesis and metastasis.

BACKGROUND

An extensive body of research exists to support the involvement of a multistep process in the conversion of normal cells to the tumorigenic phenotype (see, e.g., Land et al., 1983). Molecular models supporting this hypothesis were first provided by studies on two DNA tumor viruses, adenovirus and polyomavirus. In the case of adenovirus, it was found that transformation of primary cells required the expression of both the early region 1A (E1A) and 1B (E1B) genes (Houweling et al., 1980). It was later found that the E1A gene products could cooperate with middle T antigen or with activated H-ras gene to transform primary cells (Ruley, 1985). In addition, during the last decade, a number of human malignancies have been discovered to be correlated with the presence and expression of "oncogenes" in the human genome. More than twenty different oncogenes have now been implicated in tumorigenesis, and are thought to play a direct role in human cancer (Weinberg, 1985). Many of these oncogenes apparently evolve through mutagenesis of a normal cellular counterpart, termed a "proto-oncogene", which leads to either an altered expression or activity of the expression product. There is considerable data linking proto-oncogenes to cell growth, including their expression in response to certain proliferation signals (see, e.g., Campisi et al., 1983) and expression during embryonic development (Muller et al., 1982). Moreover, a number of the proto-oncogenes are related to either a growth factor or a growth factor receptor. These observations suggested the involvement of multiple functions in the transformation process, and that various oncogenes may express similar functions on a cellular level.

The adenovirus E1A gene codes for several related proteins to which a number of interesting properties have been attributed. In addition to its ability to complement a second oncogene in transformation, a closely related function allows E1A to immortalize primary cells (Ruley, 1985). For example, introduction of E1A gene products into primary cells has been shown to provide these cells with an unlimited proliferative capacity when cultured in the presence of serum. Another interesting action of E1A function is so-called "trans-activation", wherein E1A gene products stimulate transcription from a variety of viral and cellular promoters, including the adenovirus early and major late promoter as well as other promoters. However, trans-activation is not universal for all promoters. In some instances, E1A causes a decrease in transcription from cellular promoters that are linked to enhancer elements (Haley et al., 1984). It has been shown that exogenously added E1A gene can reduce the metastatic potential of ras-transformed rat embryo fibroblast cells by activating the cellular NM23 gene that is associated with a lower metastatic potential (Pozzatti et al., 1988; Wallich et al., 1985).

In the case of Adenovirus 5, the E1A gene products are referred to as the 13S and 12S products, in reference to the sedimentation value of two mRNAs produced by the gene. These two mRNAs arise through differential splicing of a common precursor, and code for related proteins of 289 and 243 amino acids, respectively. The proteins differ internally by 46 amino acids that are unique to the 13S protein. A number of E1A protein species can be resolved by PAGE analysis, and presumably arise as a result of extensive post-translational modification of the primary translation products (Harlow et al., 1985).

Another viral oncoprotein, the SV 40 large T antigen (LT) shares structural and functional homology to E1A and c-myc (Figge et al., 1988). LT, E1A and c-myc have transforming domains which share amino acid sequence homology and similar secondary structure (Figge et al., 1988). All three proteins complex with the tumor suppressor, retinoblastoma gene product (Rb) (Whyte et al., 1988, DeCaprio et al., 1988, Rustgi et al., 1991), and the Rb binding domains of LT and E1A coincide with their transforming domains. Based on this similarity, it has been thought that LT and E1A transform cells by binding cellular Rb and abrogating its tumor suppressor function. LT, E1A and c-myc are also grouped as immortalization oncogenes as determined by the oncogene cooperation assay using rat embryo fibroblasts (Weinberg, 1985).

In spite of the similarity between the Rb binding domains of LT and E1A, the two proteins differ substantially in other regards. In fact, there is apparently only a short equivalent stretch of acidic amino acids (Figge et al., 1988). This stretch lies between amino acids 106–114 in LT and amino acids 121–139 in E1A. The large T antigen is encoded by the simian virus 40, a member of the polyoma virus family. In contrast, E1A is encoded by adenovirus 5 virus, which is a member of the adenovirus family. LT is 708 amino acids long, while E1A is substantially shorter at 289 or 243 amino acids (for 13S and 12S respectively). LT has been observed to bind directly to certain DNA sequences; however, direct binding of E1A to DNA has not been observed and E1A may instead interact indirectly via a co-activator such as p300 (as discussed in Chen & Hung, 1997). LT binds with the tumor suppressors Rb and also with p53. E1A complexes with Rb but apparently not with p53. E1A has been shown to induce apoptosis in cells, but this has not been demonstrated for LT. Further, LT is an apparent anomaly in the scheme of oncogenic classification. Oncogenes are typically classified as being cytoplasmic or nuclear oncogenes. However, LT, through the actions of a single protein, is able to introduce "nuclear" characteristics such as immortalization as well as "cytoplasmic" characteristics such as anchorage independence in cells (Weinberg, 1985). LT antigen can be found in both the nucleus and at the plasma membrane, and mutations that inhibit the transport of LT into the nucleus appear to reduce its immortalizing ability while leaving intact its effect on anchorage independence and its ability to transform already immortalized cells. Consequently, this oncogene is considered to be a member of both the nuclear and cytoplasmic oncogenic classes, since it its gene product apparently affects these two distinct cellular sites (Weinberg, 1985); which again is unlike E1A.

Despite advances in identifying certain components which contribute to the development of malignancies, it is clear that the art still lacks effective means of suppressing carcinogenesis. Recently, however, M. C. Hung and collaborators have made great advances in the suppression of oncogenic transformation. Some of these advances are described in U.S. Pat. Nos. 5,651,964, 5,641,484, and 5,643, 567, the entire text of each being specifically incorporated by reference herein and briefly described below.

Suppression of Oncogenesis

Work by Hung and collaborators has established that the E1A gene can in fact suppress transformation, tumorigenicity and metastasis in a variety of cancers (see, e.g., Yu et al. 1991, 1992 and 1993; and the reviews by Hung et al., 1995, Yu and Hung, 1995, and Mymryk, 1996).

Without wishing to be bound by theory, it appears that there may be more than one pathway or means by which E1A can act to suppress oncogenic transformation. In particular, while Hung and collaborators initially established that E1A can suppress tumor formation in vitro and in vivo in cancers that appear to be associated with an over-expression of an oncogene variously referred to as c-erbB-2, HER-2 or neu (hereinafter the neu oncogene); it appears that E1A can also suppress the oncogenic phenotype in various other cancer cells that do not appear to be associated with an overexpression of neu. Indeed, Frisch et al. have reported that the tumor-suppressing effects of the E1A gene can also be used to convert three unrelated types of human cancer cells (which do not appear to be over-expressing neu) into a non-transformed state (see, e.g., Frisch, 1991, 1994 and 1995, and Mymryk, 1996). However, even these cells appear to express neu at some relatively lower levels. Whether the suppression of transformation in cells not over-expressing neu is nevertheless facilitated by a reduction in neu levels and/or is facilitated by other means, the outcome in either case is suppression of oncogenesis. In sum, therefore, it appears that E1A can effectively function as a tumor suppressor gene for a variety of different human cancer cells including both cancer cells that are overexpressing neu, and those that are not. E1A protein has also been reported to induce a cytotoxic response that resembles programmed cell death (i.e. apoptosis) (Rao et al., 1992), which may also contribute to the tumor-suppressing properties of E1A.

These results not only establish E1A as a tumor suppressor gene, but also suggest that E1A is a potential therapeutic reagent for the treatment of a variety of human cancers. Indeed, success with the use of E1A as a tumor suppressor gene in animal models of human cancer has merited the initiation of Phase I human clinical trials for multiple indications which are currently being sponsored by Targeted Genetics Corporation at the Virginia Mason Medical Center in Seattle, at the M.D. Anderson Cancer Center in Houston, and at Wayne State University in Detroit, at the Rush Presbyterian—St. Luke's Medical Center in Chicago. In addition, Targeted Genetics' European partner, Groupe Fournier, has now received approval by the Ministry of Health to begin corresponding clinical trials in France.

As noted above, one of the ways in which E1A may mediate suppression of the oncogenic phenotype is through an effect on the putative oncogene c-erbB-2/HER-2/neu, overexpression of which is associated with a variety of human cancers, including human breast and ovarian cancers among others. The c-erbB-2/HER-2/neu oncogene has been found to be similar to, but distinct from, the c-erbB gene, which is a member of the tyrosine-specific protein kinase family to which many proto-oncogenes belong. The c-erbB gene encodes the epidermal growth factor receptor (EGFr) and is highly homologous to the transforming gene of the avian erythroblastosis virus (Downward et al., 1984).

The neu oncogene, which encodes a p185 tumor antigen, was first identified in transfection studies in which NIH 3T3 cells were transfected with DNA from chemically induced rat neuroglioblastomas (Shih et al., 1981). The p185 protein has an extracellular, transmembrane, and intracellular domain, and therefore has a structure consistent with that of a growth factor receptor (Schechter et al., 1984). The human neu gene was first isolated due to its homology with v-erbB and EGF-r probes (Senba et al., 1985). Molecular cloning of the transforming neu oncogene and its normal cellular counterpart, the neu proto-oncogene, indicated that activation of the neu oncogene was due to a single point mutation resulting from one amino acid change in the transmembrane domain of the neu encoded p185 protein (Bargmann et al., 1986; Hung et al., 1989). The neu oncogene is of particular importance to medical science because its presence has been correlated with the incidence of cancers of the human breast and female genital tract among others. Moreover, amplification/overexpression of this gene has been directly correlated with relapse and survival in human breast cancer (Slamon et al., 1987). Therefore, it is an extremely important goal of medical science to evolve information regarding the neu oncogene, particularly information that could be applied to reversing or suppressing the oncogenic progression that seems to be elicited by the presence or activation of this gene. Unfortunately, little has been previously known about the manner in which one may proceed to suppress the oncogenic phenotype associated with the presence of oncogenes such as the neu oncogene.

The neu proto-oncogene is often notably amplified in patients with metastatic breast cancer. Hung et al. have shown that neu transcription can be repressed by E1A products in an established rat embryo fibroblast cell line, Rat-1. Furthermore, Hung et al. have found that in SK-BR-3 human breast cancer cells expression of the p185 protein, the human neu gene product, was reduced by introduction of E1A gene. The derepression effect observed in the co-transfection experiment with the Stu1-Xho1 fragment has demonstrated that this reduction of p185 proteins is likely due to the similar transcriptional repression mechanisms.

As noted above, Hung and collaborators, who have been studying various cancers that appear to be associated with over-expression of the neu oncogene, have successfully demonstrated that E1A gene products are able to suppress not only the tumorigenic and transformation events but are also able to suppress metastatic events associated with such cancers. See, e.g. Yu et al., 1992; Yu et al., 1991; Yu et al., 1993. As described by Yu et al., 1993, SKOV3.ip1 is a derivative cell line isolated from the ascites that developed in mice given injections of human ovarian carcinoma SKOV-3 cells. Compared with parental SKOV-3 cells, the SKOV3.ip1 cell line expresses higher levels of c-erbB-2/neu-encoded p185 protein and correspondingly exhibits more malignant phenotypes determined by in vitro and in vivo assays. This association between enhanced c-erbB-2/neu expression and more severe malignancy is very consistent with previous studies in which c-erbB-2/neu overexpression was shown to correlate with poor prognosis in ovarian cancer patients (Slamon et al, 1989). These studies provided actual evidence to support those clinical studies indicating that c-erbB-2/neu overexpression can be used as a prognostic factor for ovarian cancer patients and that c-erbB-2/neu overexpression may play an important role in the pathogenesis of certain human malignancies such as ovarian cancer. The identification and molecular cloning of the ligands for the c-erbB-2/neu-encoded p 185, which can increase the tyrosine phosphorylation of p 185, will enhance our understanding of the molecular mechanisms and the biological effects of c-erbB-2/neu overexpression in human cancer and cancer metastasis (Peles et al., 1992; Holmes et al., 1992; Lupu et al., 1990; Yarden & Peles, 1991; Huang & Huang, 1992; Dobashi et al., 1991).

The adenovirus E1A gene was originally defined as a transforming oncogene that can substitute for the myc oncogene and simian virus 40 large tumor antigen gene in the ras co-transformation assay of primary embryo fibroblasts (Land et al., 1983; Ruley, 1983; Weinberg, 1985).

As noted above, Hung et al. discovered that E1A gene products can act as transformation and metastasis suppressors in transformed mouse 3T3 cells. It was further demonstrated that the E1A gene products effectively repressed c-erbB-2/neu gene expression in SKOV3.ip1 ovarian carcinoma cells, suppressed transformation phenotypes in vitro, and reduced tumorigenicity and mortality rate in viva. Hence it was demonstrated that the adenovirus E1A gene can function as a tumor suppressor gene for human cancer cells as well as inhibit transformation induced by a mutation-activated neu oncogene in rodent cells. Without wishing to be bound by theory, it appears that the reduced p185 expression in the ip1.E1A cell lines may be due to transcriptional repression of the overexpressed c-erbB-2/neu gene, which may be one of the means by which E1A can suppress the tumorigenic potential of SKOV3.ip1 ovarian cancer cells. Interestingly, it has been shown that adenovirus E1A can also render hamster cell lines more susceptible to lysis by natural killer cells and macrophages (Cook & Lewis, 1984; Sawada et al., 1985); and it increased sensitivity to cytotoxicity by tumor necrosis factor in transfected NIH 3T3 cells (Cook et al., 1989). Therefore, it is conceivable that the tumor-suppressing function of E1A may be partly due to an increased susceptibility to cytolytic lymphoid cells and molecules.

It has been proposed that there are cellular "E1A-like" factors that may mimic the function of E1A in certain cell types (Nelson et al., 1990). Many common features between E1A and c-myc suggest that the c-myc gene product may be one of the cellular homologues of the E1A protein. These common features include the following: E1A and c-myc share a similar structural motif (Figge & Smith, 1988; Figge et al., 1988); both E1A and c-myc can transform primary embryo fibroblasts in cooperation the ras oncogene (Land et al., 1983; Ruley, 1983); both can bind specifically to the human Rb gene product, the Rb protein (Whyte et al., 1988; Rustgi et al., 1991); both can induce apoptosis in certain cell types (Rao et al., 1992; Frisch, 1991; Nelson et al., 1990; Figge & Smith, 1988; Figge et al., 1988; Whyte et al., 1988; Rustgi et al., 1991; Evan et al., 1992); and both have been shown to block transformation of certain transformed cell lines (Frisch, 1991; Nelson et al., 1990; Figge & Smith, 1988; Figge et al., 1988; Whyte et al., 1988; Rustgi et al., 1991; Evan et al., 1992; Suen & Hung, 1991). In addition, Hung et al. have found that, similar to the E1A proteins, the c-myc gene product can repress c-erbB-2/neu gene expression at the transcription level, resulting in reversal of the neu-induced transformed morphology in NIH 3T3 cells (Wang et al, 1991).

It appears that E1A can inactivate the Rb tumor suppressor gene by complexing with the Rb gene product, Rb protein, and by inducing Rb protein phosphorylation (Whyte et al., 1988; Rustgi et al., 1991; Evan et al., 1992; Suen & Hung, 1991; Wang et al., 1991). Therefore, Hung et al. have recently examined whether Rb might also regulate c-erbB-2/neu expression. Similar to E1A, Rb can also repress c-erbB-2/neu gene expression at the transcriptional level (Yu et al., 1992). The cis-acting elements responding to E1A and Rb are different but only a few base pairs away from each other. It may be that E1A and Rb might interact with each other to regulate c-erbB-2/neu transcription.

Without wishing to be bound by theory, one of the interesting issues regarding the correlation between c-erbB-2/neu overexpression and poor clinical outcome in human breast and ovarian cancers is whether c-erbB-2/neu overexpression is the result of an aggressive tumor or has a causative role for aggressive tumors. The data presented by Hung et al. (U.S. Pat. Nos. 5,651,964, 5,641,484, and 5,643,567) supported a role for c-erbB-2/neu overexpression in the pathogenesis of certain aggressive tumors. First, comparison of the SKOV-3 cell line and the derivative SKOV3.ip1 cell line revealed a correlation between increased c-erbB-2/neu expression level and enhanced malignant phenotype measured by in vitro and in vivo assays. Second, when c-erbB-2/neu expression in the E1A-expressing ip1.E1A cells was dramatically repressed, the malignant potential of these cells was diminished. Taken together, these observations suggest a close relationship between c-erbB-2/neu over-expression and the more malignant tumor pattern. Since tumorigenesis is likely to be a multi-step process, as noted above, it is also possible that the neu oncogene contributes to the development or progression of a tumorigenic phenotype in certain cancers even if it does not initiate the process. In that regard, neu can also serve as an indicator of the state of tumorigenesis. For example, c-erbB-2/neu-overexpressing ovarian tumors tend to be more malignant, and therefore more aggressive therapy might be beneficial to those ovarian cancer patients whose tumors overexpress c-erbB-2/neu-encoded p185. As noted above, one of the ways in which E1A might suppress tumorigenesis is via c-erbB-2/neu, which could involve indirect control at the transcriptional level. It has been proposed that E1A may form a complex with cellular transcription factor(s) and thereby modulate the specific binding of the transcription factor(s) to enhancer elements that are important for transcription (Mitchell et al., 1989). Identification of the defined DNA sequences responsible for the E1A-mediated inhibition of neu transcription would therefore allow the identification of the transcription factor(s) that may be involved in this process. Recent work by Chen and Hung provides evidence that p300 may act as such a co-activator in the transcriptional regulation of neu (Chen and Hung, 1997).

Regardless of the precise mechanism of action, the work of Hung and collaborators (using neu-overexpressing cancer cells), taken in conjunction with the work by Frisch et al. (using non-neu-overexpressing cancer cells), provide evidence that E1A can effectively function as a tumor suppressor gene for a variety of different human cancer cells including cancer cells that are overexpressing neu, and those which are not. E1A has also been shown to sensitize cancer cells to chemotherapeutic agents and thus can be used as a combination therapy in the treatment of cancer cells. This tumor sensitization effect of E1A also appears to be active in both neu-over-expressing cancer cells and non-neu-over-expressing cancer cells as shown by Hung and collaborators, and by Frisch et al. (see, e.g., PCT/US97/03830 and PCT/US95/11342).

While the role of E1A as a tumor suppressor gene has thus been established, it has not been clear which regions of E1A are required for this suppression. The present invention describes portions of E1A that are apparently necessary for the tumor suppressor activity and those regions that are apparently dispensable. Removal of various portions of E1A has resulted in the generation of various "mini-E1A" genes that can be used as alternative means for providing the E1A tumor suppressor activity. Such mini-E1A genes will be useful as potential therapeutic reagents for the treatment of various human cancers.

SUMMARY OF THE INVENTION

The present invention provides methods for the suppression of oncogenesis. The methods comprise introducing a mini-E1A gene or gene product into a cell in a manner effective to suppress oncogenesis. The cell may be a neu-overexpressing cell or a non-neu-overexpressing cell. Such cells may be found in a tumor.

In some embodiments, the mini-E1A gene product has at least a segment of the C-terminal region of the E1A protein as described below. For example, an "E1A-Cterm" product described and illustrated below apparently contains only about 80 amino acid residues of the C-terminal (corresponding to about amino acids 209–289 of 13S E1A). Nevertheless, this relatively small region of the C-terminus has been found to exhibit significant tumor suppression activity in vivo. Smaller fragments within the 209–289 portion of the 13S E1A gene product that retain the ability to suppress tumorigenicity can be readily identified by removing or altering residues within this domain.

In other embodiments, the mini-E1A gene product has at least a C-terminal domain, an N-terminal domain, and/or the CR1 domain of an E1A gene product. In one embodiment, the C-terminal domain may have an amino acid segment comprising between about 4 and about 80 amino acids. Similarly, the N-terminal domain may have an amino acid segment comprising between about amino acid 4 and about amino acid 25 of an E1A gene product. Likewise, the CR1 domain may comprise an amino acid segment having between about amino acid 40 and about amino acid 80 of an E1A gene product. The mini-E1A gene product may further comprise a spacer. Such a spacer may be placed at the C-terminal end of the CR1 domain of an E1A product, or in any other suitable location. In some embodiments, the spacer comprises an amino acid segment comprising between about amino acid 81 and about amino acid 101 of an E1A 13S gene product. The mini-E1A gene product may comprise a C-terminal domain of an E1A gene product. For example, the C-terminal domain may comprise an amino acid segment comprising between about amino acid 209 and amino acid 289 of an E1A 13S gene product (corresponding to amino acids 163–243 of an E1A 12S gene product) or a tumor-suppressing fragment thereof.

Thus, in some embodiments, the mini-E1A gene product is an E1A gene product from which at least 15 amino acids of the N-terminal region, preferably at least 25 amino acids from the N-terminal region have been removed. In some embodiments, the mini-E1A gene product is an E1A gene product from which both the CR1 region and the CR2 region have been ablated; and in some products, the entire amino terminal region (as well as CR3) has been ablated, leaving only about 80 amino acids or less from the C-terminal region of E1A. Illustrations of such constructs are provided below.

The mini-E1A gene products of the present invention may be introduced into a cell, tumor, organism, etc. by any number of methods. The gene product itself may be obtained and then introduced. In such a case, the gene product may be obtained via any method known in the art. Further, a mini-E1A gene product may be introduced through the introduction of a nucleic acid segment which encodes a mini-E1A gene product in a manner which results in expression of the mini-E1A gene product. In some preferred embodiments, the nucleic acid segment is DNA. The nucleic acid segment may comprise a mini-E1A gene operatively linked to a promoter. For introduction, the nucleic acid segment may be located on a vector, for example, a plasmid vector or a viral vector. The viral vector may be, for example, an adenoviral vector, a retroviral vector, an AAV vector, or other viral vector which can transfect mammalian cells. By way of illustration, the nucleic acid segment can be introduced via an adenovirus comprising an E1A mini-gene, and, in some preferred embodiments, the adenovirus is a replication-deficient adenovirus.

A mini-E1A gene product may be introduced into a cell by contacting the cell with a mini-E1A gene product-encoding DNA in a complex with a lipid. Such a mini-E1A gene product-encoding DNA/lipid complex may be in the form of a structured lipid-based gene delivery vehicle (such as a liposome or micelle) or in an unstructured complex such as a lipid dispersion. In some embodiments, the complex is a combination of a mini-E1A gene product-encoding DNA, a lipid and a polycation. Exemplary polycations include, e.g., protamines, polyarginines, polyornithines, polylysines, polybrenes, spermines, spermidines, histones, and cationic dendrimers. In some embodiments, the mini-E1A gene product-encoding DNA is complexed with one or more of DOTMA, DOPE, or DC-Chol. In some specific embodiments, the mini-E1A gene product-encoding DNA is complexed with DC-Chol. In more specific embodiments, the mini-E1A gene product-encoding DNA is complexed with DC-Chol and DOPE. DNA condensation agents (such as protamine sulfate) and/or DNA targeting agents (such as members of ligand-receptor pairs) may also be employed. Other non-viral gene delivery complexes can also be employed (See, e.g., PCT/US95/04738 by Targeted Genetics Corporation).

The mini-E1A gene products and nucleic acids of the present invention may be introduced in vivo using any suitable method. For example, injection, oral, and inhalation methods may be employed, with the skill artisan being able to determine an appropriate method of introduction for a given circumstance. In some preferred embodiments, injection will be used. This injection may be intravenous, intraperitoneal, intramuscular, subcutaneous, intratumoral, intrapleural, or of any other appropriate form.

The present invention contemplates methods of suppressing transformation of a cell comprising introducing a transformation suppressing amount of a mini-E1A gene product into a cell in a manner effective to suppress an oncogenic phenotype. In some preferred embodiments, the mini-E1A gene product is introduced into the cell through the introduction of a nucleic acid segment which encodes a mini-E1A gene product. In some cases, the cell may be a tumor cell, and the introduction may be in a situation where the growth of a tumor is to be suppressed. The transformation suppressing mini-E1A gene product may be any of the mini-E1A gene products discussed above. Administration of the mini-E1A gene product may be through any of the methods discussed above.

The invention contemplates a mini-E1A gene product comprising a C-terminal domain of the E1A gene product. Also contemplated is a mini-gene comprising an N-terminal domain and/or the CR1 domain of an E1A gene product, which may further comprise a spacer domain and/or a C-terminal domain of the E1A-gene product. Other preferred mini-E1A gene products are E1A gene products from which the CR2 and/or CR1 region has been ablated.

The invention also contemplates a nucleic acid encoding a mini-E1A gene product. The encoded mini-E1A gene product may be a mini-E1A gene product derived from either a 12S or 13S E1A gene product, including any of the mini-E1A gene products described above. In some preferred embodiments, the mini-E1A gene encodes at least the N-terminal, and the CR1 domain of an E1A gene product. For example, the N-terminal domain may comprise an amino acid segment having a segment stretching between about amino acid 4 and about amino acid 25 of an E1A-gene product. Further, the CR1 domain may comprise an amino acid segment having a segment stretching between about amino acid 40 and about amino acid 80 of an E1A gene product. The mini-E1A gene may further encode a spacer. Such a spacer may be positioned at the C-terminal end of the CR1 domain of an E1A 13S gene product, and/or may comprise an amino acid segment comprising between about amino acid 81 and about amino acid 101 of an E1A 13S gene product. In some preferred embodiments, the mini-E1A gene encodes at least a C-terminal domain of an E1A gene product. For example, the C-terminal domain may comprise an amino acid segment comprising between about amino acid 209–289 of an E1A 13S gene product (corresponding to amino acids 163–243 of an E1A 12S gene product) or a sub-fragment thereof exhibiting tumor-suppressing activity. In other preferred embodiments mini-E1A gene product is encoded by an E1A gene from which the CR2 and/or CR1 region has been ablated. In a number of these embodiments, the mini-E1A gene product lacks at least about 15 amino acids, more typically at least about 25 amino acids, of the N-terminal region.

The invention further contemplates methods of supplying mini-E1A activity to a cell by introducing a mini-E1A gene that is expressed in the cell. The mini-E1A gene products, mini-E1A genes, and methods of introduction can be any of those discussed herein.

The invention further contemplates methods to suppress the growth of a tumor in a mammal comprising contacting the tumor with a mini-E1A gene product and a chemotherapeutic agent. This combination therapy is expected to have great benefits. The mini-E1A gene product may be as described above. Any suitable chemotherapeutic agent may be employed, however, cisplatin, doxorubicin, VP16, taxol, and/or TNF are presently preferred. The invention includes within its scope methods of inhibiting tumorigenesis and/or metastasis comprising administering to an animal having or suspected of having cancer an effective combination of mini-E1A gene product and a chemotherapeutic drug in an effective amount to inhibit the cancer. Combinations of a mini-E1A gene product and an LT gene product are also contemplated. Preferably, the LT gene product is a nontransforming derivative of LT.

The invention also involves methods of inhibiting transformation of a cell comprising contacting the cell with a mini-E1A gene product and a tyrosine kinase inhibitor. In preferred embodiments, the emodin-like tyrosine kinase inhibitor is emodin.

Further, the invention contemplates a therapeutic kit comprising, in a suitable container, a pharmaceutical formulation of a mini-E1A gene product or a nucleic acid encoding a mini-E1A gene product, and optionally also comprising a pharmaceutical formulation of a chemotherapeutic drug.

In keeping with long-standing patent law convention, the words "a" and "an," when used in the present specification, including the claims, denote "one or more."

BRIEF DESCRIPTION OF THE DRAWINGS

(FIG. 5A). Decreased $^3$H-thymidine incorporation by the mini-E1A stable transfectants versus B104-1-1 parental cells. $^3$H-thymidine (1 μCi/well) was added to cells at the indicated time points to label those cells that were synthesizing DNA prior to harvest. Radioactivity of individual samples was counted by a scintillation counter; average cpm were calculated from ten replicate samples. Experiments were repeated two times for each cell line. (FIG. 5B). MTT assays were performed as described in Materials and Methods at the indicated days after plating. Average OD 590 nm values were calculated from ten replicate samples. Experiments were repeated two times for each cell line.

As shown in FIG. 9, the subclone appeared to be particularly aggressive in that all placebo-treated mice (Group I) had succumbed to tumorigenesis within less than 40 days. As also shown, while all nine control animals were dead by that time, none of the animals receiving full-length E1A or mini-E1ACterm had died. Mini-E1ACterm was equivalent to full-length E1A in tumor suppression.

DETAILED DESCRIPTION OF THE PREFERRED EMBODIMENTS

Figure 1A:
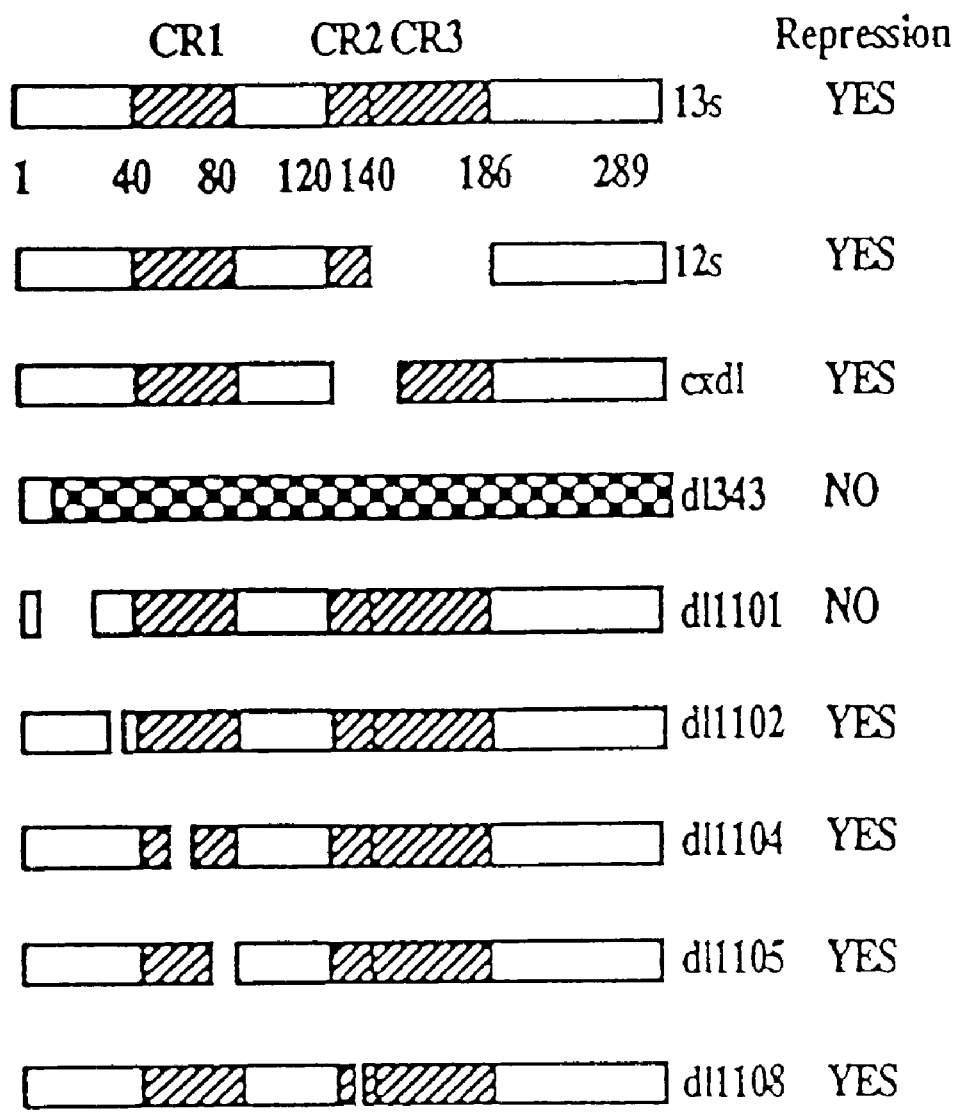
FIG. 1A, FIG. 1B, FIG. 1C and FIG. 1D. Mapping of E1A functional domains involved for transcriptional repression of neu oncogene. E1A plasmid, E1A frameshift plasmid (dl343), or E1A mutants (20 μg) were cotransfected into NIH 3T3 cells along with pNeu-StuI-CAT (4 μg) and pRSVb-gal (4 μg). The pNeu-StuI-CAT contains the CAT gene driven by neu promoter. The pRSVβ-gal, which contains the LacZ gene driven by the RSV promoter, was used as an internal control for normalization of transfection efficiency. The schematic structures of E1A and its mutants were shown in FIG. 1A. The hatched areas represent the conserved regions of E1A. The discontinuous regions represent the deletion regions. The representative sets of data are shown in FIG. 1B and FIG. 1C. The repressed CAT activities are further diagrammed in FIG. 1D. The standard deviations are shown by error bars.

The present invention provides mini-E1A gene products that can be used in the suppression of oncogenesis. The invention provides methods for treating various cancers using mini-E1A gene products, which can also be used in combination with other anti-cancer agents and/or emodin-like tyrosine kinase inhibitors to treat cancer cells.

A. Definitions and Techniques Affecting Gene Products and Genes.

Mini-E1A and E1A Gene Products and Genes

"E1A gene product" and "E1A" refer to proteins having amino acid sequences which are substantially identical to the native E1A amino acid sequence and which are biologically active in that they are capable of binding to Rb, suppressing transformation (e.g. neu oncogene-mediated transformation), immortalizing cells, or cross-reacting with anti-E1A antibody raised against E1A. Such sequences are disclosed, for example, in Berk et al., 1978. The term "E1A gene product" also includes analogs of E1A molecules which exhibit at least some biological activity in common with native E1A. Furthermore, those skilled in the art of mutagenesis will appreciate that other analogs, as yet undisclosed or undiscovered, may be used to construct E1A analogs. Such analogs may be generated in the manners described for the generation of LT mutants in Kalderon et al. (1984). In the context of this patent, the terms "mini-E1A gene product" and "mini-E1A" refer to proteins having amino acid sequences which are substantially identical to the native E1A amino acid sequence except that they lack at least part of the N-terminal portion of E1A (defined as amino acids 1–119 encoded in exon 1 of E1A) and which are biologically active in that they are capable of suppressing transformation (and/or cross-reacting with anti-E1A antibody raised against E1A). Presently, preferred mini-E1A gene products comprise at least a C-terminal portion of E1A (defined as amino acids 186–289 in exon 2 of E1A).

The E1A gene generally produces two major spliced products, the 12S and 13S mRNAs, that encode proteins 243 and 289 amino acids long, respectively (Moran et al., 1987). To determine which E1A gene product was responsible for the observed repression, the same studies were performed with recombinant plasmids expressing either 12S or 13S E1A gene product (pE1A-12S and pE1A-13S). Hung et al. have previously shown that both the 12S and 13S products were effective at repressing neu transcription in a concentration-dependent manner. These E1A gene products contain at least two of three highly conserved regions referred to as CR1, CR2, and CR3 (Moran et al., 1987; Van Dam et al., 1989). In particular, while CR1 and CR2 exist in both the 12S and 13S, CR3 is unique to the 13S product. Since 12S itself can itself repress oncogenesis, Hung et al. reasoned that the CR3 is dispensable for suppression. However, the present inventors have discovered that other portions of E1A, which are found in both the 12S and 13S wild-type gene products, are nevertheless dispensable for tumor suppression and that various mini-E1A genes as described herein can effectively suppress tumorigenesis and enhance long-term survival in vivo.

The term "E1A gene" refers to any DNA sequence that is substantially identical to a DNA sequence encoding an E1A gene product as defined above. The term also refers to RNA, or antisense sequences compatible with such DNA sequences. An "E1A gene" may also comprise any combination of associated control sequences. Likewise a "mini-E1A gene" refers to any DNA sequence that is substantially identical to a DNA sequence encoding a mini-E1A gene product where the mini-E1A gene product is missing at least a part of the N-terminal domain. In some cases the entire CR2 region is ablated in which case it is possible to have a 13S-derived mini-E1A gene product comprising the CR1 portion operatively linked to the N-terminal region, the spacer region between CR1 and CR2, the CR3 region, and the C-terminal, or any variable combination of portions thereof. Analogously, in 12S-derived mini-E1A gene products it is possible to have mini-E1A gene products comprising the CR1 portion operatively linked to the N-terminal region, the spacer region between CR1 and CR2, the C-terminal or any variable combination of portions thereof. In some preferred embodiments, the mini-E1A gene encodes at least a portion of the C-terminal domain of an E1A gene product. For example, the C-terminal domain may comprise an amino acid segment comprising between about amino acid 209–289 of an E1A 13S gene product (corresponding to amino acids 163–243 of an E1A 12S gene product). Smaller fragments within the 209–289 portion of the 13S E1A gene product that retain some ability to suppress tumorigenicity can be readily identified by removing additional residues from this domain.

The term "substantially identical", when used to define either a mini-E1A or E1A amino acid sequence or mini-E1A or E1A gene nucleic acid sequence, means that a particular subject sequence, for example, a mutant sequence, varies from the sequence of natural E1A by one or more substitutions, deletions, or additions, the net effect of which is to retain at least some biological activity of the E1A protein. Alternatively, DNA analog sequences are "substantially identical" to specific DNA sequences disclosed herein if: (a) the DNA analog sequence is derived from coding regions of the natural E1A gene; or (b) the DNA analog sequence is capable of hybridization of DNA sequences of (a) under moderately stringent conditions and which encode biologically active mini-E1A or E1A; or (c) DNA sequences which are degenerative as a result of the genetic code to the DNA analog sequences defined in (a) or (b). Substantially identical analog proteins will generally be greater than about 80% similar to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequence.

LT Gene Products and Genes

As used herein, the terms "LT gene product" and "LT" refers to proteins having amino acid sequences which are substantially identical to the native LT amino acid sequence and which are biologically active in that they are capable of binding to Rb, repressing the neu oncogene (and/or suppressing neu oncogene-mediated transformation), immortalizing cells, inducing anchorage independence, or cross-reacting with anti-LT antibody raised against LT. The sequences of LT are disclosed, for example, in Tooze—Molecular Biology of the Tumor Viruses, Fiers et al., 1978, and Reddy et al. 1978. The term "LT gene product" also includes analogs of LT molecules which exhibit at least some biological activity in common with native LT. Examples of such LT analogs are K1 and K7, which are defective for transformation of cells (Kalderon et al., 1984). Many other exemplary LT analogs are disclosed in Kalderon et al. 1984, particularly in Table 2. Furthermore, those skilled in the art of mutagenesis will appreciate that other analogs, as yet undisclosed or undiscovered, may be used to construct LT analogs. There is no need for an "LT gene product" or "LT" to comprise all, or substantially all of the amino acid sequence of the native LT gene. Shorter or longer sequences are anticipated to be of use for tumor suppression.

The term "LT gene" refers to any DNA sequence that is substantially identical to a DNA sequence encoding an LT gene product as defined above. The term also refers to RNA, or antisense sequences compatible with such DNA sequences. An "LT gene" may also comprise any combination of associated control sequences. The term "substantially identical", when used to define either an LT amino acid sequence or an LT nucleic acid sequence, means that a particular subject sequence, for example, a mutant sequence, varies from the sequence of natural LT by one or more substitutions, deletions, or additions, the net effect of which is to retain at least some biological activity of the LT protein as noted above. Alternatively, DNA analog sequences are "substantially identical" to specific DNA sequences disclosed herein if: (a) the DNA analog sequence is derived from coding regions of the natural LT gene; or (b) the DNA analog sequence is capable of hybridization of DNA sequences of (a) under moderately stringent conditions and which encode biologically active LT; or (c) DNA sequences which are degenerative as a result of the genetic code to the DNA analog sequences defined in (a) or (b). Substantially identical analog proteins will generally be greater than about 80% similar to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequence.

Percent Similarity

Percent similarity may be determined, for example, by comparing sequence information using the GAP computer program, available from the University of Wisconsin Geneticist Computer Group or an analogous procedure as known in the art. The GAP program utilizes the alignment method of Needleman et al., 1970, as revised by Smith et al., 1981. Briefly, the GAP program defines similarity as the number of aligned symbols (i.e. nucleotides or amino acids) which are similar, divided by the total number of symbols in the shorter of the two sequences. The preferred default parameters for the GAP program include (1) a unitary comparison matrix (containing a value of 1 for identities and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap; and (3) no penalty for end gaps.

Nucleic Acid Sequences

In certain embodiments, the invention concerns the use of tumor-suppressing genes and gene products, such as the mini-E1A, E1A gene product, the LT antigen gene product or both, that include within their respective sequences a sequence which is essentially that of the known LT antigen gene or E1A gene (or tumor-suppressing portion thereof), or the corresponding proteins. The term "a sequence essentially as that of LT antigen or E1A" means that the sequence substantially corresponds to a portion of the LT antigen or E1A gene and has relatively few bases or amino acids (whether DNA or protein) which are not identical to those of LT or E1A (or a biologically functional equivalent thereof, when referring to proteins). The term "biologically functional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of mini-E1A, LT antigen or E1A will be sequences which are "essentially the same".

Mini-E1A, LT antigen and E1A genes which have functionally equivalent codons are also covered by the invention. The term "functionally equivalent codon" is used herein to refer to codons that encode the same amino acid, such as the six codons for arginine or serine, and also refers to codons that encode biologically equivalent amino acids (Table 1).

TABLE 1

FUNCTIONALLY EQUIVALENT CODONS.

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic Acid | Asp | D | GAC | GAU | | | | |
| Glutamic Acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCU | | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

The present invention also encompasses the use of DNA segments which are complementary, or essentially complementary, to the sequences set forth in the specification. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment in question under relatively stringent conditions such as those described herein.

Biologically Functional Equivalents

As mentioned above, modification and changes may be made in the structure of mini-E1A, E1A or LT and still obtain a molecule having like or otherwise desirable characteristics. For example, certain amino acids may be substituted for other amino acids in a protein structure without appreciable loss of tumor suppressing activity which can be assayed functionally and also by interactive binding capacity with structures such as, for example, the neu-gene or other biological target. Since it is the interactive capacity and nature of a protein that generally defines that protein's biological functional activity, certain amino acid sequence substitutions can typically be made in a protein sequence (or, of course, its underlying DNA coding sequence) and nevertheless obtain a protein with like or even countervailing properties (e.g., antagonistic v. agonistic). By way of illustration, relatively conservative changes (e.g., substitution with an amino acid that is similar in size and shape) and/or changes outside of the functional domain can often be made without substantially disrupting the biological activity of a protein (as described in more detail below). The generation, testing and use of the mini-E1A genes described herein is in fact exemplary of the process by which such variants can be obtained and employed. It is thus contemplated by the inventors that various changes may be made in the sequence of the mini-E1A, E1A or LT proteins or peptides (or underlying DNA) without appreciable loss of their biological utility or activity.

As a general matter, it is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention. It is also well understood that where certain residues are shown to be particularly important to the biological or structural properties of a protein or peptide, e.g., residues in active sites, such residues may not generally be exchanged. This is the case in the present invention, where any changes in the functional region of mini-E1A, E1A or LT that render the peptide incapable of suppressing oncogenesis would result in a loss of utility of the resulting peptide for cancer therapy although it may nevertheless be useful in applications that are dependent essentially on structural identities (such as diagnostic applications).

Amino acid substitutions, such as those which might be employed in modifying mini-E1A, E1A or LT are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents. In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. For example, U.S. Pat. No. 4,554,101, incorporated herein by reference, indicates that the greatest local average hydrophilicity of a protein, as governed by the hydrophilicity of its adjacent amino acids, tends to correlate with its immunogenicity and antigenicity. It is understood that an amino acid can be substituted for another having a similar hydrophilicity value and still obtain a biologically equivalent protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred.

Analogously, replacement of hydrophobic amino acids with other hydrophobic amino acids can often be made without substantially disrupting the structure or activity of a polypeptide. While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Sequence Modification Techniques

Modifications to the mini-E1A, E1A and LT peptides may be carried out using techniques such as site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered. In general, the technique of site-specific mutagenesis is well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double-stranded plasmids are also routinely employed in site directed mutagenesis which eliminates the step of transferring the gene of interest from a plasmid to a phage. In general, site-directed mutagenesis in accordance herewith is performed by first obtaining a single-stranded vector or melting apart the two strands of a double stranded vector which includes within its sequence a DNA sequence which encodes the mini-E1A gene, the E1A gene or the LT gene. An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

Kalderon et al. (1984) report several mutagenic methods which have proved useful in mutating the native LT gene. Specifically, Kalderon et al. teach deletion mutations by displacement-loop mutagenesis and by the random insertion of EcoRI linkers into the LT gene. Further, point mutation by deletion-loop mutagenesis is taught. The reference also teaches screening procedures for determining the success of such mutations. The teachings of Kalderon et al. (1984) are incorporated by reference in this application.

The preparation of sequence variants of the selected gene using site-directed mutagenesis is provided as a means of producing potentially useful mini-E1A, E1A, LT, or other oncogenesis-suppressing species and is not meant to be limiting as there are other ways in which sequence variants of these peptides may be obtained. For example, recombinant vectors encoding the desired genes may be treated with mutagenic agents to obtain sequence variants (see, e.g., a method described by Eichenlaub, 1979 for the mutagenesis of plasmid DNA using hydroxylamine).

Other Structural Equivalents

In addition to the mini-E1A, E1A and LT peptidyl compounds described herein, the inventors also contemplate that other sterically similar compounds may be formulated to mimic the key portions of the peptide structure. Such compounds may be used in the same manner as the peptides of the invention and hence are also functional equivalents. The generation of a structural functional equivalent may be achieved by the techniques of modeling and chemical design known to those of skill in the art. It will be understood that such sterically similar constructs fall within the scope of the present invention.

B. Chemosensitization Of Cancer Cells To Chemotherapeutics By Adenovirus E1A

Previous studies by Hung et al. have shown that adenoviral E1A can also chemosensitize cancer cells to chemotherapeutic agents (see, e.g., PCT/US97/03830). In those studies, neu overexpression was related to chemoresistance. In exemplary studies examining the effects of taxol (as a chemotherapeutic agent) on cell growth, rat fibroblasts with various neu and E1A expression constructs were grown in varying concentrations of taxol 0.01–100 $\mu$M. The highest inhibition of cell growth was seen in BE1A1.Hy with neu down-regulated by E1A in a taxol concentration of 0.1–10 $\mu$M.

In addition, Frisch et al., studying cancer cells that do not overexpress HER-2/neu, have reported that E1A can also act to sensitize such cells to chemotherapeutic agents (see, e.g., WO96/07322).

Collectively, these studies suggest that E1A genes and gene products are of use in the sensitization of a variety of cancer cells to chemotherapeutic agents. The various mini-E1A genes of the present invention can thus be employed in conjunction with chemotherapeutic agents as a combination therapy for suppressing tumorigenesis and/or metastasis.

C. Chemosensitization Of Cancer Cells To Chemotherapeutics By Emodin-Like Tyrosine Kinase Inhibitors Emodin, which was first isolated from *Polygonum cuspidatum*, has also been shown to be an inhibitor of the protein tyrosine kinase $p56^{lck}$ (Jayasuriya et al.; 1992). Hung et al. have show that emodin is able to inhibit neu tyrosine kinase activity and to preferentially repress the transformation ability and growth rate of breast cancer cells which are also over-expressing neu. Emodin also can inhibit the growth of cancer cells, including lymphocytic leukemia (Kupchan et al., 1976), HL-60 human leukemia cells (Yeh el al., 1988), and ras-transformed human bronchial epithelial cells (Chan et al., 1993), by an unknown mechanism.

Hung et al. have demonstrated that emodin and emodin-like compounds suppress the tyrosine kinase activity of human breast cancer cells, suppress their transforming ability, and induce their differentiation. Further, Hung et al. have found that emodin also suppresses tyrosine phosphorylation of neu in lung cancer cells and preferentially inhibits growth of these cells. Further, it appears that emodin is able to sensitize lung cancer cells that overexpress neu to the chemotherapeutic agents cisplatin, doxorubicin, and VP16 (See, e.g., PCT/US97/01686). Without wishing to be bound by one theory, it may be that the tyrosine kinase activity of $p185^{neu}$ is required for the chemoresistant phenotype of neu overexpressing cancer cells. Regardless of the precise mechanism, it appears that adding emodin to chemotherapeutic regimens can greatly improve their efficacy. The present invention thus contemplates the use of mini-E1A in gene therapy in combination with emodin-like tyrosine kinase inhibitors in order to suppress tumor growth.

The delivery of emodin-like tyrosine kinase inhibitors to cancer cells is well within the skill of those in the art and are described for example, by Hung et al., in PCT/US97/01686. Treatment and delivery protocols are discussed elsewhere in the specification.

D. In vivo Delivery and Treatment Protocols

Where a gene itself is employed to introduce gene products, a convenient method of introduction will be through the use of a recombinant vector which incorporates the desired gene, generally together with associated control sequences that promote and/or regulate expression of the gene. The preparation of such recombinant vectors as well as the use of various control sequences is well known to those of skill in the art and described in many references, such as, for example, Sambrook et al. (1989), specifically incorporated herein by reference.

In vectors, it is understood that the DNA coding sequences to be expressed (in this case those encoding the oncogenesis-suppressing gene products) are generally positioned adjacent to and under the control of a promoter. It is understood in the art that to bring a coding sequence under the control of such a promoter, one generally positions the 5' end of the transcription initiation site of the transcriptional reading frame of the gene product to be expressed "downstream" of (i.e., 3' of) the chosen promoter. As is also known in the art, altering the spacing between a promoter and a nearby transcriptional start site can often be used to influence the level of expression of the transcript. Where a heterologous promoter is to be used to drive expression of a gene (i.e., a non-E1A promoter in the case of an E1A gene), one can initially employ a spacing that is similar to that between the heterologous promoter and the gene it normally controls (typically less than 100 to several hundred base pairs). However, optimization of expression can involve moving the promoter closer or further from the transcriptional start site. One may also desire to incorporate into the transcriptional unit of the vector an appropriate polyadenylation site (e.g., 5'-AATAAA-3'), if one was not contained within the original inserted DNA. Typically, these poly A addition sites are placed about 30 to 2000 nucleotides "downstream" of the coding sequence at a position prior to transcription termination.

While the control sequences of the specific gene (i.e., the E1A promoter for mini-E1A, E1A and the LT promoter for LT) can be employed, other control sequences that function in the cell can also be used. A variety of such promoters, including both constitutive promoters and inducible promoters have been described in the art and are generally available from numerous sources including, e.g., ATCC and commercial sources. Thus, one may mention other useful promoters by way of example, including, e.g., an SV40 early promoter, a CMV promoter, a long terminal repeat promoter from retrovirus, an actin promoter, a heat shock promoter, a met allothionein promoter, and the like.

For introduction of the mini-E1A, E1A or LT gene, one will generally desire to employ a vector construct that will also facilitate delivery of the desired gene to the affected cells which may require that the construct be delivered to the targeted tumor cells (e.g., breast, genital, lung or other tumor cells) in a patient. One way of facilitating delivery is by the use of a viral vector to carry the mini-E1A, E1A or LT sequences to efficiently infect a tumor, or pre-tumorous tissue. Exemplary viral vectors include adenoviral, retroviral, vaccinia viral, and adeno-associated viral vectors. These and/or other viral vectors have been successfully used to deliver desired sequences to cells with high infection efficiency.

Commonly used viral promoters for expression vectors are derived from polyoma, cytomegalovirus, Adenovirus, and Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism.

An exemplary vector, that might be used as a starting point for construction, is the E1A containing retroviral vector, termed pSVXE1A-G, described by Robert et al., 1985. This vector comprises the E1A gene which has been brought under the control of the SV-40 early promoter. For LT expression, the pZ189 (driven by the SV-40 promoter) and the pVU-O vectors both contain LT. LT mutants are contained in, for example, pK1 and pK7 as well as other vectors described by Kalderon et al. 1984. The inventors propose that these constructs could either be used directly in the practice of the invention, or could be used as a starting point for the introduction of other more desirable promoters such as those discussed above.

(i) Adenovirus

One method for in vivo delivery of tumor-suppressing gene of the present invention involves the use of an adenovirus vector. An "adenovirus expression vector" is meant to include those constructs containing adenovirus sequences sufficient to (a) support packaging of the construct and (b) to express a polynucleotide that has been cloned therein. Adenoviral transfer of mini-E1A or E1A is especially convenient, because E1A is itself an adenoviral gene. Therefore, there need be no non-viral genetic sequences inserted into an adenoviral vector to accomplish adenoviral delivery of mini-E1A or E1A. Of course, LT-encoding DNA, or other neu-suppressing gene product encoding sequences may be introduced via adenoviral vectors as well.

An exemplary expression vector comprises a genetically engineered form of adenovirus. Knowledge of the genetic organization of adenovirus, a 36 kb, linear double-stranded DNA virus, allows substitution of large pieces of adenoviral DNA with foreign sequences up to 7 kb (Grunhaus and Horwitz, 1992). In contrast to retrovirus, the infection of adenoviral DNA in host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells and can infect a number of other cells as well.

Adenovirus is a particularly suitable gene transfer vector because of its midsized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and some cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, located at 16.8 m$\mu$ is particularly efficient during the late phase of infection, and all the mRNAs issued from this promoter possess a 5'-tripartite leader (TL) sequence which makes them preferred mRNAs for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system is an alternative approach for the production of recombinant adenovirus.

A preferred method of introducing the mini-E1A gene or E1A to an animal is to introduce a replication-deficient adenovirus containing the mini-E1A gene or E1A gene. An example of such an adenovirus is Ad.E1A(+). Since adenovirus is a common virus infecting humans in nature and the mini-E1A gene is part of a gene that is present in native adenovirus, the use of a replication deficient mini-E1A virus to introduce the gene can effect efficient delivery and expression of mini-E1A gene products in target cells.

The replication-deficient mini-E1A virus made by E1B and E3 deletion also avoids the viral reproduction inside the cell and transfer to other cells and infection of other people, which means the viral infection activity is effectively limited to the first infected target cell. The mini-E1A gene is still expressed inside such cells. Also, unlike retrovirus, which can only infect proliferating cells, adenovirus is able to transfer the mini-E1A gene or the E1A gene into both proliferating and non-proliferating cells possibly by stimulating non-proliferating cells. Further, the extrachromosomal location of adenovirus in the infected cells decreases the chance of cellular oncogene activation within the treated animal.

While the replication-competent adenovirus may thus be used directly to transfer the mini-E1A gene or the E1A gene into cancer cells, replication-competent virus can produce large amounts of adenovirus in the human body and therefore might cause potential side effects due to the replication-competent nature of the wild type adenovirus. It is therefore an advantage to use the replication-deficient adenovirus such as E1B and E3 deletion mutant Ad.E1A(+) to prevent such side effects. In fact, many modifications in the native adenovirus will result in a modified virus that will be useful for the purpose of the invention. Further modification of adenovirus such as E2A deletion may improve the mini-E1A expression efficiency and reduce the side effects. The only requirement of a native or modified adenovirus is that it should be able to deliver a mini-E1A gene that can be expressed in a target cell in order to have the utility of the invention.

Adenovirus can also be used for introducing an LT gene product into such a cell. The LT gene product can be an LT mutant, especially a nontransforming mutant such as K1. Such introduction can typically involve the introduction of an LT gene. In some preferred methods, the LT gene can be introduced by the use of an adenovirus that contains both the mini-E1A gene and the LT gene. In this case, adenovirus is preferably a replication-deficient adenovirus such as the Ad.E1A(+) adenovirus. However, the introduction of the LT gene can be by any manner described in this specification or known to those of skill in the art such as viral, plasmid, retroviral vectors or liposomes. Introduction of adenovirus containing the tumor-suppressing gene (e.g. a mini-E1A gene) into a suitable host is typically done by injecting the virus contained in a buffer. As discussed above, it is advantageous if the adenovirus vector is replication defective, or at least conditionally defective. The adenovirus may be of any of the 42 different known serotypes or subgroups A–F. Adenovirus type 5 of subgroup C is presently preferred starting material for obtaining conditional replication-defective adenovirus vector for use in the present invention. This is because Adenovirus type 5 is a human adenovirus about which the most biochemical and genetic information is known, and it has historically been used for most constructions employing adenovirus as a vector.

Where a mini-E1A gene is used in an adenovirus vector, it can occupy the position normally occupied by the full-length E1A gene, or it can be placed at another position in an adenovirus construct. For example, the polynucleotide encoding an E1A mini-gene can be inserted in lieu of a deleted E3 region in E3 replacement vectors as described by Karlsson et al., (1986) or in the E4 region where a helper cell line or helper virus complements the E4 defect, at the E1B or E2 locus or at another location.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. No side effects have been reported in studies of vaccination with wild-type adenovirus (Couch et al., 1963; Top et al., 1971), demonstrating their general safety and therapeutic potential as in vivo gene transfer vectors.

Adenoviruses have been used in eukaryotic gene expression (Levrero et al., 1991; Gomez-Foix et al., 1992) and vaccine development (Grunhaus and Horwitz, 1992; Graham and Prevec, 1992). Animal studies have suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

(ii) Retroviruses

The retroviruses are a group of single-stranded RNA viruses characterized by an ability to convert their RNA to double-stranded DNA to infected cells by a process of reverse-transcription (Coffin, 1990). The resulting DNA can stably integrate into cellular chromosomes as a provirus and direct synthesis of viral proteins. The integration results in the retention of the viral gene sequences in the recipient cell and its descendants. The retroviral genome contains three genes, gag, pol, and env, that code for capsid proteins, polymerase enzyme, and envelope components, respectively. A sequence found upstream from the gag gene, termed ψ components is constructed (Mann et al., 1983). When a recombinant plasmid containing a human cDNA, together with the retroviral LTR and ψ sequences is introduced into this cell line (by calcium phosphate precipitation for example), the ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vector particles are able to infect a broad variety of cell types. However, integration and stable expression require the division of host cells (Paskind et al., 1975).

A novel approach designed to allow specific targeting of retrovirus vectors was developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989). There are certain potential limitations to the use of retrovirus vectors. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact ψ sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990). One limitation to the use of retrovirus vectors in vivo is the limited ability to produce retroviral vector titers greater than $10^6$ infections U/mL. Titers 10- to 1,000-fold higher are necessary for many in vivo applications.

More recent approaches to the use of retroviral vectors for directing the delivery of genes to particular target cells, such as cancer cells, which would avoid many of these limitations have been described by Paul and Overell (Targeted Genetics Corporation) in U.S. patent application Ser. No. 08/244,469, now proceeding to issuance.

(iii) Other Viral Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and hepadnaviruses may be employed. They offer several attractive features for various mammalian cells (Friedmann, 1989; Ridgeway, 1988; Baichwal and Sugden, 1986; Coupar et al., 1988; Howrich et al., 1990).

A variety of advantages associated with the use of AAV vectors for gene delivery, and methods and compositions for the preparation of such vectors, have been described by Targeted Genetics Corporation and collaborators; see, e.g., Allen et al., WO96/17947; Trempe et al., Ser. No. 08/362, 608, now proceeding to issuance; and Flotte et al., U.S. Pat. No. 5,658,776. Additional references describing AAV vectors which could be used in the methods of the present invention include the following: Carter, B., Handbook of Parvoviruses, vol. 1, pp. 169–228, 1990; Berns, Virology, pp. 1743–1764 (Raven Press 1990); Carter, B., Curr. Opin. Biotechnol., 3: 533–539, 1992; Muzyczka, N., Current Topics in Microbiology and Immunology, 158: 92–129, 1992; Flotte, T. R., et al., Am. J. Respir. Cell Mol. Biol. 7:349–356, 1992; Chatterjee et al., Ann. NY Acad. Sci., 770: 79–90, 1995; Kotin, R., Human Gene Therapy, 5: 793–801, 1994; Flotte, T. R., et al., Gene Therapy 2:357–362, 1995; and Du et al., Gene Therapy 3: 254261, 1996.

With the recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. introduced the 10 chloramphenicol acetyltransferase (CAT) gene into duck hepatitis B virus genome in the place of the polymerase, surface, and pre-surface coding sequences. It was cotransfected with wild-type virus into an avian hepatoma cell line. Cultures media containing high titers of the recombinant virus were used to infect primary duckling hepatocytes. Stable CAT gene expression was detected for at least 24 days after transfection (Chang et al., 1991).

(iv) Lipid-based Gene Delivery

In a further embodiment of the invention, the expression construct may be associated with one or more lipids. As is known in the art of lipid-based gene delivery, such nucleic acid-lipid complexes can be in a variety of different forms depending generally on the nature of the lipid employed, the ratio of nucleic acid to lipid and/or other possible components, and the method by which the complex is formed. Exemplary types of complexes include structured complexes such as liposomes and micelles, as well as relatively unstructured complexes such as lipid dispersions. By way of illustration, liposomes are vesicular structures generally characterized by a bilayer membrane, such a phospholipid bilayer, enclosing an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes. The present invention thus also provides particularly useful methods for introducing mini-E1A gene products into cells. One method of in vivo gene transfer which can lead to expression of genes transfected into cells involves the use of liposomes. Liposomes can be used for both in vitro and in vivo transfection.

Liposome-mediated gene transfer seems to have great potential for certain in vivo applications in animals (Nicolau et al., 1987). Studies have shown that intravenously injected liposomes are taken up essentially in the liver and the spleen, by the macrophages of the reticuloendothelial system. The specific cellular sites of uptake of injected liposomes appears to be mainly spleen macrophages and liver Kupffer cells. Intravenous injection of liposome/DNA complexes can lead to the uptake of DNA by these cellular sites, and result in the expression of a gene product encoded in the DNA (Nicolau, 1983). The inventors contemplate that mini-E1A gene products can be introduced into cells using liposome-mediated gene transfer. It is proposed that such constructs can be coupled with liposomes and directly introduced via a catheter, as described by Nabel et al. (1990). By employing these methods, the tumor-suppressing gene products of the present invention can be expressed efficiently at a specific site in vivo, not just the liver and spleen cells which are accessible via intravenous injection. Therefore, this invention also encompasses compositions of DNA constructs encoding mini-E1A gene product formulated as a DNA/liposome complex and methods of using such constructs.

Liposomes, micelles, and lipid dispersions can be prepared using any of a variety of lipid components (and potentially other components) that can be complexed with nucleic acid or which can entrap e.g., an aqueous compartment comprising a nucleic acid. Illustrative molecules that can be employed include phosphatidylcholine (PC), phosphatidylserine (PS), cholesterol (Chol), N-[1-(2,3-dioleyloxy)propyl]-N,N-trimethylammonium chloride (DOTMA), dioleoylphosphatidylethanolamine (DOPE), and/or 3β[N-(N'N'-dimethylamino-ethane)-carbarmoyl cholesterol (DC-Chol), as well as other lipids known to those of skill in the art. Those of skill in the art will recognize that there are a variety of lipid-based transfection techniques which will be useful in the present invention. Among these techniques are those described in Nicolau et al., 1987, Nabel et al., 1990, and Gao et al., 1991. The inventors have had particular success with lipid/DNA complexes comprising DC-Chol. More particularly, the inventors have had success with lipid/DNA complexes comprising DC-Chol and DOPE which have been prepared following the teachings of L. Huang and collaborators (see, e.g., Gao et al., 1991; Epand et al., PCT/US92/07290, and U.S. Pat. No. 5,283,185). Lipid complexes comprising DOTMA, such as those which are available commercially under the trademark Lipofectin™, from Vical, Inc., San Diego, Calif., may also be used. A variety of improved techniques for lipid-based gene delivery that can be employed to deliver genes such as those disclosed herein have been described by L. Huang and collaborators (see, e.g., Gao et al., U.S. patent application Ser. No. 08/376,701, now proceeding to issuance; Deshmukh et al., PCT/US97/06066; Liu et al., PCT/US96/15388, and Huang et al., PCT/US97/12544).

Lipid/nucleic acid complexes can be introduced into contact with cells to be transfected by a variety of methods. In cell culture, the complexes can simply be dispersed in the cell culture solution. For application in vivo, the complexes are typically injected. Intravenous injection allows lipid-mediated transfer of complexed DNA to, for example, the liver and the spleen. In order to allow transfection of DNA into cells which are not accessible through intravenous injection, it is possible to directly inject the lipid-DNA complexes into a specific location in an animal's body. For example, Nabel et al. teach injection of liposomes via a catheter into the arterial wall. In another example, the present inventors have used intraperitoneal injection of lipid/DNA complexes to allow for gene transfer into mice.

The present invention also contemplates compositions comprising a lipid complex. This lipid complex will generally comprise a lipid component and a DNA segment encoding a tumor-suppressing gene. The tumor-suppressing gene employed in the lipid complex can be, for example, -10 mini-E1A gene, an LT gene or an E1A gene. Lipid complexes comprising LT mutants may have certain advantages. These advantages may be particularly distinct when the LT gene encodes non-transforming LT mutant, such as K1. A mini-E1A gene may be similarly complexed with a lipid to form a lipid/DNA complex for gene delivery.

The lipid employed to make the lipid complex can be any of the above-discussed lipids. In particular, DOTMA, DOPE, and/or DC-Chol may form all or part of the lipid complex. The inventors have had particular success with complexes comprising DC-Chol. In a preferred embodiment, the lipid complex comprises DC-Chol and DOPE. While many ratios of DC-Chol to DOPE can have utility, it is anticipated that those comprising a ratio of DC-Chol:DOPE between 1:20 and 20:1 will be particularly advantageous. The inventors have found that lipid complexes prepared from a ratio of DC-Chol:DOPE of about 1:10 to about 1:5 have been particularly useful from the standpoint of stability as well as efficacy.

The E1A, mini-E1A and LT gene products are capable of suppressing oncogenesis and it is proposed that one may employ any product, or two or more together, in the practice of the invention. In addition, it is contemplated that certain regions of either the mini-E1A, E1A or the LT gene may be employed exclusively without employing the entire mini-E1A, E1A or LT gene respectively.

It is proposed that it will ultimately be preferable to employ the smallest region needed for tumor suppression so that one is not introducing unnecessary DNA into cells which receive a mini-E1A, E1A or LT gene construct. This may especially be true with regard to the rather large, 708 amino acid, LT protein. In conjunction with the teachings and detailed illustrations of the present invention, techniques well known to those of skill in the art, such as the use of restriction enzymes and mutagenesis techniques, can be used for the generation of small regions of mini-E1A, E1A and LT. The ability of these regions to inhibit tumorigenesis can easily be determined using assays analogous to those reported in the Examples.

In certain embodiments of the invention, the lipid may also be complexed with a hemagglutinating virus (HVJ). This has been shown to facilitate fusion with the cell membrane and to promote cell entry of liposome-encapsulated DNA (Kaneda et al., 1989). In other embodiments, the lipid may be complexed or employed in conjunction with nuclear non-histone chromosomal proteins (HMG-1) (Kato et al., 1991). In yet further embodiments, the lipid may be complexed or employed in conjunction with both HVJ and HMG-1. Work by Huang and collaborators has also provided a number of lipid-based gene delivery compositions, some comprising nucleic acid condensing agents and other components; and has further described detailed techniques that can be used for the production of such gene delivery complexes (see, e.g., Targeted Genetics Corporation PCT/US97/12544 and U.S. patent application Ser. No. 08/376,701, proceeding to issuance; as well as other references by Huang et al. above).

In that such expression constructs have been successfully employed in transfer and expression of nucleic acid in vitro and in vivo, then they are applicable for the present invention. As is known in the art, one can also include other components within the gene delivery complex, including proteins and/or other molecules that facilitate targeting to particular cells, binding and uptake by targeted cells, localization within particular subcellular compartments (e.g., the nucleus or cytosol), as well as integration and/or expression of the DNA delivered. A variety of such individual components, and combinations thereof, have been described by Targeted Genetics Corporation in PCT/US95/04738.

(v) Other Non-viral vectors

In order to effect expression of sense or antisense gene constructs, the expression construct must generally be delivered into a cell. This delivery may be accomplished in vitro, as in laboratory procedures for transforming cells lines, or in vivo or ex vivo (see below), as in the treatment of certain disease states. As described above, delivery may be via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al, 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al, 1990), and receptor-mediated transfection (Wu and Wu, 1987; Wu and Wu, 1988). Some of these techniques may be successfully adapted for in vivo or ex vivo use.

Improved approaches to non-viral gene delivery using gene delivery fusion proteins (GDFPs) have been described by Overell and Weisser (Targeted Genetics Corporation) in PCT/US95/04738.

Once the expression construct has been delivered into the cell the nucleic acid encoding the gene of interest may be positioned and expressed at different sites. In certain embodiments, the nucleic acid encoding the gene may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of $CaPO_4$ precipitates into liver and spleen of adult and newborn mice demonstrating active viral replication and acute infection. Benvenisty et al., (1986) also demonstrated that direct intraperitoneal injection of $CaPO_4$ precipitated plasmids results in expression of the transfected genes. It is envisioned that DNA encoding a gene of interest (e.g., a mini-E1A gene) may also be transferred in a similar manner in vivo and express the gene product Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force. The microprojectiles used have consisted of biologically inert substances such as tungsten or gold beads.

Selected organs including the liver, skin, and muscle tissue of rats and mice have been bombarded in vivo (Zelenin et al., 1991). This may require surgical exposure of the tissue or cells, to eliminate any intervening tissue between the gun and the target organ, ie., ex vivo treatment. Again, DNA encoding a particular gene may be delivered via this method and still be incorporated by the present invention.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. By virtue of cell type-specific distribution of various receptors, the delivery can be made highly specific (Wu and Wu, 1987; 1988; Overell and Weisser (Targeted Genetics Corporation) in PCT/US95/04738).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). A synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a lipid complex. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without lipids. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells, in vitro, and then the return of the modified cells back into an animal. This may involve the surgical removal of tissue/organs from an animal or the primary culture of cells and tissues. See, e.g., Anderson et al., U.S. Pat. No. 5,399,346.

E. Chemotherapeutic Agents

A wide variety of chemotherapeutic agents may be used in combination with the therapeutic genes of the present invention. These can be, for example, agents that directly cross-link DNA, agents that intercalate into DNA, and agents that lead to chromosomal and mitotic aberrations by affecting nucleic acid synthesis.

Agents that directly cross-link nucleic acids, specifically DNA, are envisaged and are shown herein, to eventuate DNA damage leading to a synergistic antineoplastic combination. Agents such as cisplatin, and other DNA alkylating agents may be used.

Agents that damage DNA also include compounds that interfere with DNA replication, mitosis, and chromosomal segregation. Examples of these compounds include adriamycin (also known as doxorubicin), VP-16 (also known as etoposide), verapamil, podophyllotoxin, and the like. Widely used in clinical setting for the treatment of neoplasms these compounds are administered through bolus injections intravenously at doses ranging from 25–75 mg/m$^2$ at 21 day intervals for adriamycin, to 35–100 mg/m$^2$ for etoposide intravenously or orally.

It is contemplated that antibiotics such as Doxorubicin, Daunorubicin, Mitomycin Actinomycin D, Bleomycin, plant alkaloids (such as Taxol), Vincristine, Vinblastine, alkylating agents such as Carmustine, Melphalan, Chlorambucil, Busulfan, Lomustine and miscellaneous agents such as Cisplatin, VP16 (etoposide), and inhibitory or cytotoxic peptides such as Tumor Necrosis Factor will be useful in conjunction with the present invention. These are examples of some routinely used chemotherapeutic agents, but these are only exemplary and the list is by no means exhaustive. The skilled artisan is further referred to "Remington's Pharmaceutical Sciences" 15th Edition, chapter 61 regarding further information about these and other chemotherapeutic agents. The person responsible for administration of chemotherapeutic agent will, as a matter of course, determine the appropriate doses for the individual subject.

F. Pharmaceutical Compositions and Routes of Administration

Compositions of the present invention will have an effective amount of a gene for therapeutic administration, optionally in combination with an effective amount of a second agent that is a chemotherapeutic agent as exemplified above. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, rinses, inhalants and the like.

The expression vectors and delivery vehicles of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by, e.g., orthotopic, intradermal, subcutaneous, intramuscular, intraperitoneal or intravenous injection. Such compositions would normally be administered as pharmaceutically acceptable compositions, described supra.

The vectors of the present invention are advantageously administered in the form of injectable compositions either as liquid solutions or suspensions. Solid forms suitable for solution in, or suspension in, liquid prior to injection also may be prepared. These preparations also may be emulsified. A typical composition for such purposes comprises 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as theyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions can take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

All the essential materials and reagents required for inhibiting tumor cell proliferation may be assembled together in a kit. When the components of the kit are provided in one or more liquid solutions, the liquid solution preferably is an aqueous solution, with a sterile aqueous solution being particularly preferred.

For in vivo use, a chemotherapeutic agent may be formulated into a single or separate pharmaceutically acceptable syringeable composition. In this case, the container means may itself be an inhalant, syringe, pipette, eye dropper, or other such like apparatus, from which the formulation may be applied to an infected area of the body, such as the lungs, injected into an animal, or even applied to and mixed with the other components of the kit.

The components of the kit may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining administration of the gene therapy and/or the chemotherapeutic drug.

The kits of the present invention also will typically include a means for containing the vials in close confinement for commercial sale such as, e.g., injection or blow-molded plastic containers into which the desired vials are retained. Irrespective of the number or type of containers, the kits of the invention also may comprise, or be packaged with, an instrument for assisting with the injection/administration or placement of the ultimate complex composition within the body of an animal. Such an instrument may be an inhalant, syringe, pipette, forceps, measured spoon, eye dropper or any such medically approved delivery vehicle.

Parenteral Administration

The active compounds of the present invention will often be formulated for parenteral administration, e.g., formulated for injection via the intravenous, intramuscular, subcutaneous, or even intraperitoneal routes. The preparation of an aqueous composition that optionally contains a second agent(s) as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form.

Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. In certain cases, the therapeutic formulations of the invention could also be prepared in forms suitable for topical administration, such as in cremes and lotions. These forms may be used for treating skin-associated diseases, such as various sarcomas.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in I mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

Targeting of cancerous tissues may be accomplished in any one of a variety of ways. Plasmid vectors and retroviral vectors, adenovirus vectors, and other viral and non-viral vectors all present means by which to target human cancers. The inventors anticipate particular success for the use of lipid-based complexes to target mini-E1A, E1A and LT genes to cancer cells. In one of the first series of clinical phases to be performed, DNA encoding E1A genes or mutants of LT such as K1 will be complexed with lipids in the manner described herein, and this DNA/lipid complex will be injected into patients with certain forms of cancer, such as breast. Intravenous injection can be used to direct genes to cells, including transformed cells. Directly injecting the complex into the proximity of a cancer can also provide for targeting of the complex with some forms of cancer. For example, cancers of the ovary can be targeted by injecting the lipid mixture directly into the peritoneal cavity of patients with ovarian cancer. Of course, lipid complexes that are selectively taken up by a population of cancerous cells can also be used as described for preferentially targeting the tumor suppressing gene(s) to particular target cells.

Those of skill in the art will recognize that the optimal treatment regimens for using E1A, mini-E1A or LT to suppress cancers can be straightforwardly determined. This is not a question of experimentation, but rather one of optimization, which is routinely conducted in the medical arts. The in vivo studies in animal models as described herein provide a starting point from which to begin to optimize the dosage and delivery regimes. The frequency of injection will initially be once a week, as was done in the mice studies. However, this frequency might be optimally adjusted from one day to every two weeks to monthly, depending upon the results obtained from the initial clinical trials and the needs of a particular patient. Human dosage amounts can initially be determined by extrapolating from the amount of E1A, mini-E1A or LT used in mice, approximately 15 $\mu$g of plasmid DNA per 50 g body weight. Based on this, a 50 kg woman might require treatment a dose in the range of about 15 mg of DNA per dose. Of course, this dosage amount may be adjusted upward or downward, as is routinely done in such treatment protocols, depending on the results of the initial clinical trials and the needs of a particular patient.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute presently preferred modes for its practice. However, those of skill in the art will, in light of the present disclosure, appreciate that many changes can be made in the specific embodiments which are disclosed and still obtain a like or similar result without departing from the spirit and scope of the invention.

EXAMPLE I

LOCALIZATION OF E1A DOMAINS INVOLVED IN SUPPRESSION OF TRANSFORMATION

The present invention has localized various E1A functional domains and identified subfragments of E1A that are capable of suppressing transformation, thereby providing various mini-E1A genes that can be employed as tumor suppressing agents. Based on work with an initial construct comprising only a portion of the N- and C-terminal domains, it appears that amino acid residues 81 to 188 are dispensable.

This first mini-E1A construct, termed E1A-N80, provides a new reagent for treatment of cancer. In addition, since the region between amino acid residues 81 to 188 is known to be associated with transformation by inactivation of tumor suppressor gene Rb (Moran et al., 1987) or transactivation of several virus gene such as E1B (Moran et al., 1987), deletion of this region can be used to obviate any potential secondary effects that could be associated with the deleted region, while still maintaining suppressing activity, thereby providing an alternative therapeutic reagent.

Materials And Methods

Cell Lines and Culture.

The B104-1-1 and NIH 3T3 cell lines were grown in DMEM/F12 medium (GIBCO, Grand Island, N.Y.) supplemented with 10% FBS. The stable transfectants were grown under the same conditions except that G418 (800 μg/ml) was added to the culture medium.

Plasmids and Construction of Mutants.

The deletion mutant cxdl and the 12S and 13S constructs were generously provided by Dr. Elizabeth Moran (The Fels Institute for Cancer Research and Molecular Biology, Temple University School of Medicine, Philadelphia, Pa.). The deletion mutants dl1101, dl102, dl1104, dl1105, and dl1108 have been described previously (Jelsma et al., 1988; Jelsma et al., 1989). The E1A gene fragments encoding the amino acid residues 1 to 40 (E1A N-terminal nonconserved domain), 1 to 80 (E1A N-terminal nonconserved domain and the CR1 domain), and 186 to 289 (E1A nuclear localization domain) were created by PCR using pE1A plasmid (Yu et al., 1990) as the template. The E1AN40 and E1AN80 mutants were generated by subcloning the 1 to 40 or 1 to 80 PCR fragments together with the nuclear localization domain (186 to 289) into the vector pCDNAI (Invitrogen, Calif.), respectively. The pCMVneo plasmid was constructed by cloning the neo gene into pCDNAI vector. The following plasmids, which have been previously described, were used in this study: the neu promoter deletion-CAT constructs (Suen and Hung, 1990), plasmid encoding point mutation-activated genomic neu, cNeu-104(2), pRSV-bgal (Edlund et al., 1985), and pSV2neo (Yu et al., 1993).

Transient Transfections and CATAssay.

NIH 3T3 cells were transfected using a modified calcium-phosphate precipitation procedure (Chen and Okayama, 1988). Four micrograms of plasmid pNeu-StuI-CAT containing 312-bp rat neu promoter and the CAT reporter gene were cotransfected with 4 μg RSVβ-gal and 20 μg of plasmids encoding E1A or deletion mutants. The cells were harvested 48 h after transfection, and cell extracts were obtained by freeze-thawing of the harvested cells between 37° C. and −70° C. The b-gal assay (Norton and Coffin, 1985) was carried out on a portion of each extract, which served as the internal transfection efficiency control for normalization of the CAT assay (Gorman et al., 1982). The CAT assay monitors acetylation of $^{14}$C-chloramphenicol in cell extracts that have been separated by TLC and visualized by autoradiography. The spots on the TLC plates were scanned and analyzed by a Betascope 603 blot analyzer (Betagen, Waltham, Mass.) Transfection experiments were repeated several times. Representative data are shown.

Focus-forming Assay.

The focus-forming assay was carried out as described previously (Yu et al., 1992b). The 1 μg cosmid clone cNeu-104 (Hung et al., 1986) containing 30 kb of activated genomic rat neu, including 2.2 kb of the neu promoter, was cotransfected into NIH 3T3 cells with 0.1 μg of the drug-selection plasmid pSV2neo and 10 μg of plasmids encoding E1A deletion mutants, E1A wild type protein, or E1A frameshift protein respectively. Cells were trypsinized and split into four plates 48 h after transfection. Two plates were maintained in regular medium, whereas the other two plates were maintained in medium supplemented with G418 (800 μg/ml). For cells kept in regular medium, foci of the transformed cells appeared on a background monolayer of non-transformed cells about 3 to 4 weeks after transfection. For cells kept in G-418 medium, G418-resistant colonies appeared at about the same time. Foci or the G-418-resistant colonies were stained with 1% crystal violet and counted. To normalize transfection efficiency, the number of foci formed for each transfection was divided by the number of G-418 colonies obtained from the same transfection. The results are shown as percentage of the normalized number of foci in each transfection versus that in control transfection, which is performed by transfection of a E1A frameshift mutant dl343 along with the cNeu-104.

Stable Transfection.

B104-1-1 cells, a point mutation-activated rat neu transformed NIH 3T3 cells, were transfected with 10 μg of E1AN80 plasmid DNA along with 1 μg of pCMV-neo plasmid DNA carrying the neomycin-resistance marker gene. The cells were trypsinized and then split at a 1:10 ratio 48 h after transfection. The cells were then grown for 4 to 6 weeks in selection medium containing 800 μg/ml of G418, after which individual G418-resistant colonies were cloned or pooled using cloning rings and expanded to mass culture.

Immunoblotting.

Immunoblot analyses were performed as previously described (Yu et al., 1990). The primary monoclonal antibodies used were M73 against the E1A proteins (a generous gift of Dr. Ed Harlow, Massachusetts General Hospital, Mass.), c-neu-Ab-3 against the neu-encoded p185 protein (purchased from Oncogene Science, Inc., Manhasset, N.Y.), and anti-β actin (purchased from Amersham, UK). The blots were then incubated with horseradish peroxidase-conjugated goat anti-mouse immunoglobulin (Bio-Rad Laboratories, Richmond, Calif.) and detected with ECL chemiluminescence western-blotting detection reagents (Amersham).

$^3$H-Thymidine Incorporation Assay.

Ten replicated cell samples were plated into 96-well plates at a density of 8×10$^3$ cells per well in culture medium. A total of three plates were used. $^3$H-thymidine (1 μCi) was added to each well at 24 h, 48 h, and 72 h, with continuous incubation after each addition for 12 h at 37° C. Cells were harvested, and cellular DNA was bound to fiber glass filters. Radioactivity of each filter was counted by a 'scintillation counter (Beckman, Fullerton, Calif.).

MTT Assay.

Approximately 10$^3$ cells/well were plated per well into 96-well culture plates in 0.1 ml of culture medium. A total of five plates (10 wells per cell line per plate) were used. One of the plates was analyzed every 24 h. After the addition of a 50 μl MTT (Sigma Chemical Co., St Louis, Mo.) stock solution (1.25 mg MTT/ml of PBS) to each well on the plate, cells were incubated continuously for 4 h at 37° C. The medium was aspirated, and the cells were lysed in 100 μl of dimethylsulfoxide. Conversion of MTT to formazan by metabolically viable cells was monitored by a Dynatech MR 5000 fluorescence microplate reader at 590 nm wavelength.

Colony Formation in Soft Agarose.

The ability of different cells to grow in soft agarose was determined as previously described (Yu et al., 1992b). Cells (10$^3$ cells/well, four wells for each cell line) were plated into 24-well plates in culture medium containing 0.35% agarose (BRL, Gaithersburg, Md.) overlying a 0.7% agarose layer. The cells were then incubated at 37° C. for 5 weeks, after which the plates were stained with p-iodonitrotetrazolium violet (I mg/ml) for 48 h at 37° C. Colonies greater than 100 microns were counted for each dish and cell line.

Animals and Tumorigenicity Assay.

Four- to six-week-old athymic female homozygous nu/nu mice were purchased from Harlan-Sprague Dawley, Inc. (Indianapolis, Ind.). The care and use of the animals were in accordance with institutional guidelines. The cells in log-phase growth were trypsinized, washed twice with PBS, and centrifuged at 250×g. The viable cells were counted, and 3×10$^6$ cells in 0.1 ml of PBS were injected s.c. into both the right and left flanks of female mice under aseptic conditions. Tumor volumes were estimated as the product of three-dimensional caliper measurements (longest surface length and width; tumor thickness). The growth of tumors was monitored every other day for 2 to 3 weeks.

Results

Amino Acids 81–188 of E1A are Not Required for Suppression. Expression and Suppression of Foci Formation Induced by Mutation-Activated neu.

Figures 1B, 1C:
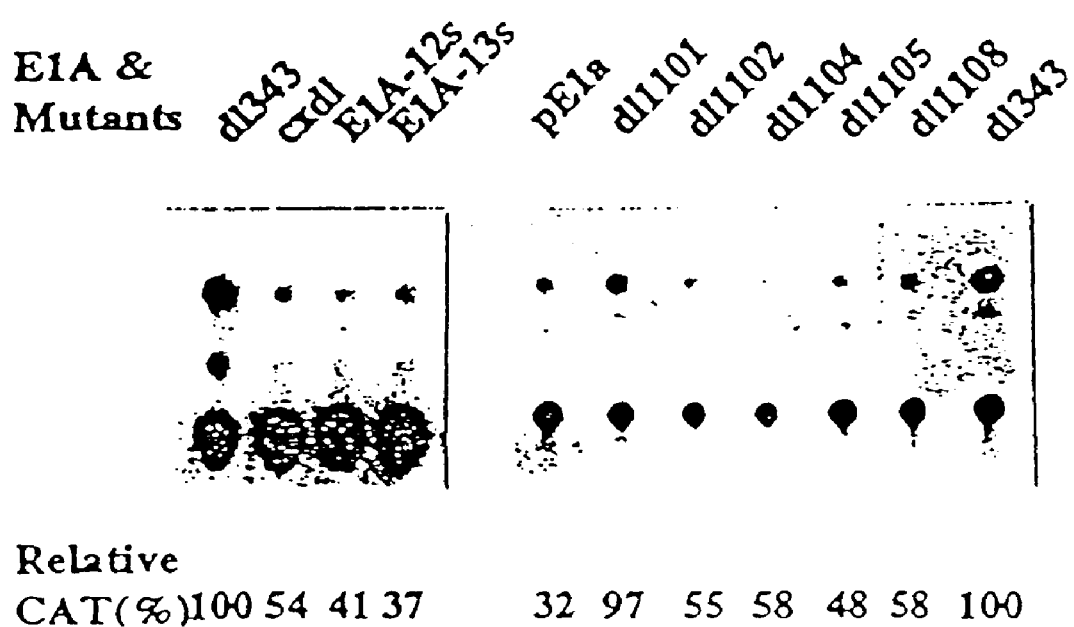
Figure 1D:
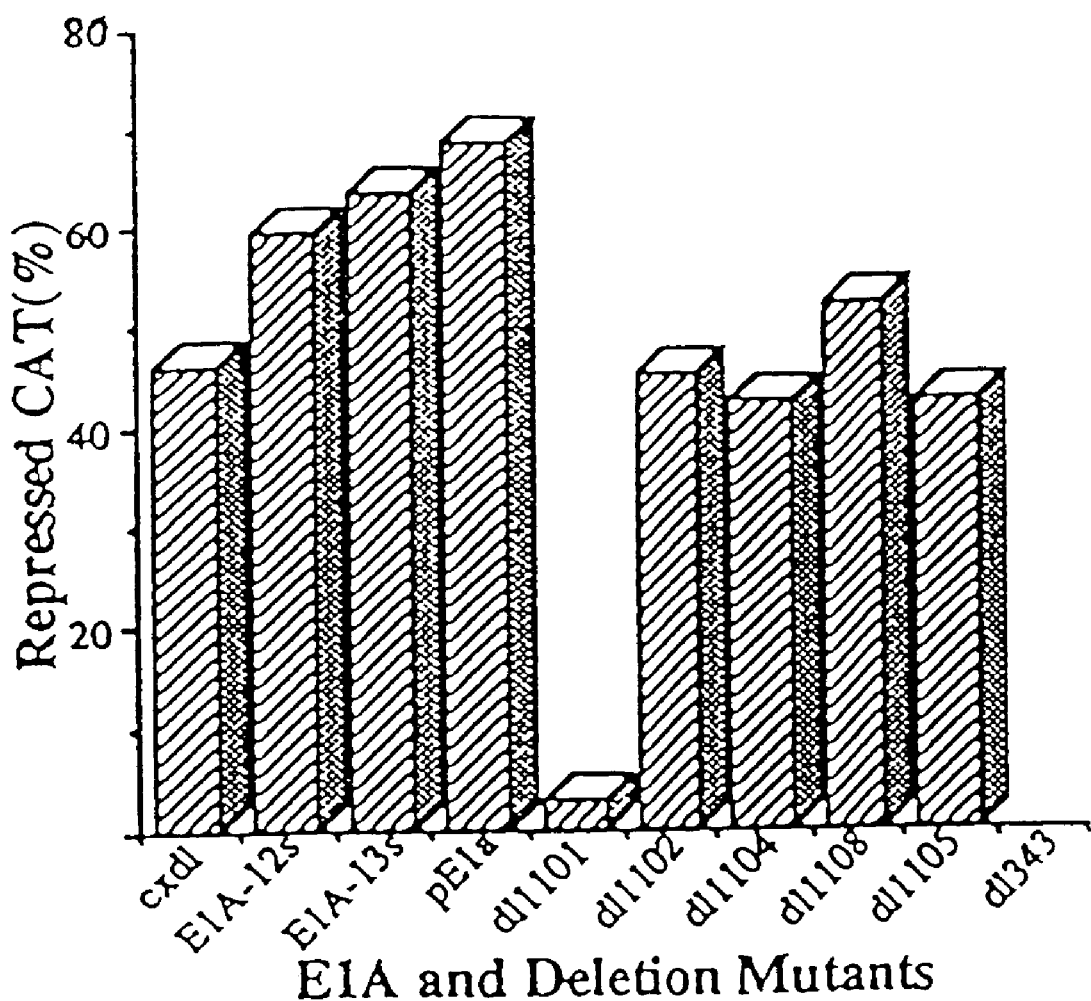

To map which region of the E1A protein may be required for repression of neu expression, a series of E1A mutants were examined for their ability to repress promoter activity by co-transfection with a neu promoter-CAT plasmid in NIH 3T3 cells. As shown in FIG. 1A, FIG. 1B, and FIG. 1D, the large deletion mutants, cxdl, in which the entire CR2 region is deleted, effectively repressed neu promoter activity compared with 12S (CR3 deletion) and 13S E1A that had previously been shown to inhibit neu promoter activity (Yu et al., 1990). A frameshift deletion mutant, dl343, unable to repress the neu promoter, was used as a negative control. This result indicated that CR2 and CR3 domains are not required for repression of neu expression.

To further map whether the N-terminal and CR1 domains is required for the repression of neu promoter activity, we co-transfected another set of small deletion mutants (FIG. 1A, FIG. 1C, and FIG. 1D) in the N-terminal nonconserved domain and the CR1 domain with a neu promoter-CAT construct: dl1101 and dl1102 (in which amino acid residues 4 to 25 or 26 to 35 in N-terminal nonconserved domain were deleted, respectively), and dl1104 and dl1105 (in which amino acid residues 48 to 60 or 70 to 80 in CR1 domain were deleted, respectively). Another mutant, dl1108, which deleted the amino acid residues 123 (Thr) in CR2 domain, and cannot bind to the Rb protein, was also tested to confirm that Rb-binding is not required for neu repression. All these E1A mutants were driven by the same adenovirus 5 E1A promoter (Jelsma et a., 1988; Jelsma et al., 1989).

When these mutants were transiently transfected into the NIH 3T3 cells, all of them expressed the protein products at the level comparable with that of the wild type E1A, as verified by western blot analysis. The dl1101 mutant appeared to exhibit a decreased ability to repress neu, whereas other mutant proteins still significantly repressed the promoter activity.

The results suggest that while a small piece of the adenovirus 5 E1A N-terminal (amino acid residues 4 to 25) might affect repression of neu expression, other parts of the CR1 and the entire CR2 are dispensable, and confirmed that the Rb-binding function in CR2 domain is not required.

Figure 2A:
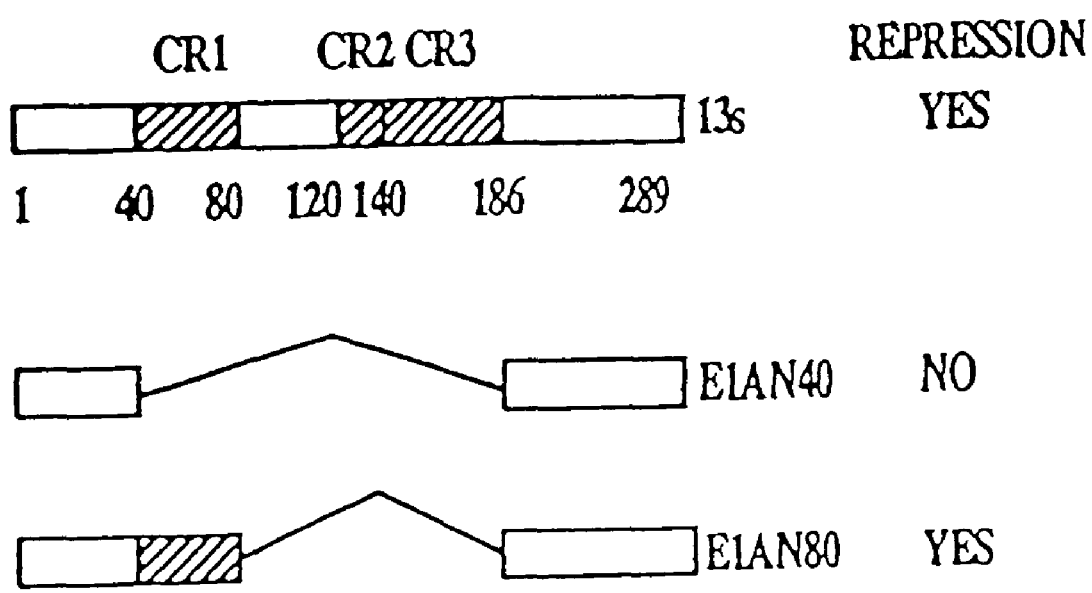
FIG. 2A, FIG. 2B, and FIG. 2C. E1A N-terminal non-conserved domain and CR1 domain. The schematic structures of E1A and the mutants are shown in FIG. 2A. The repression of neu promoter activity by mutant E1AN80 and the E1A proteins expressed by E1A and deletion mutants are shown in FIG. 2B and FIG. 2C. Results of one of three experiments is shown.
Figure 2B:
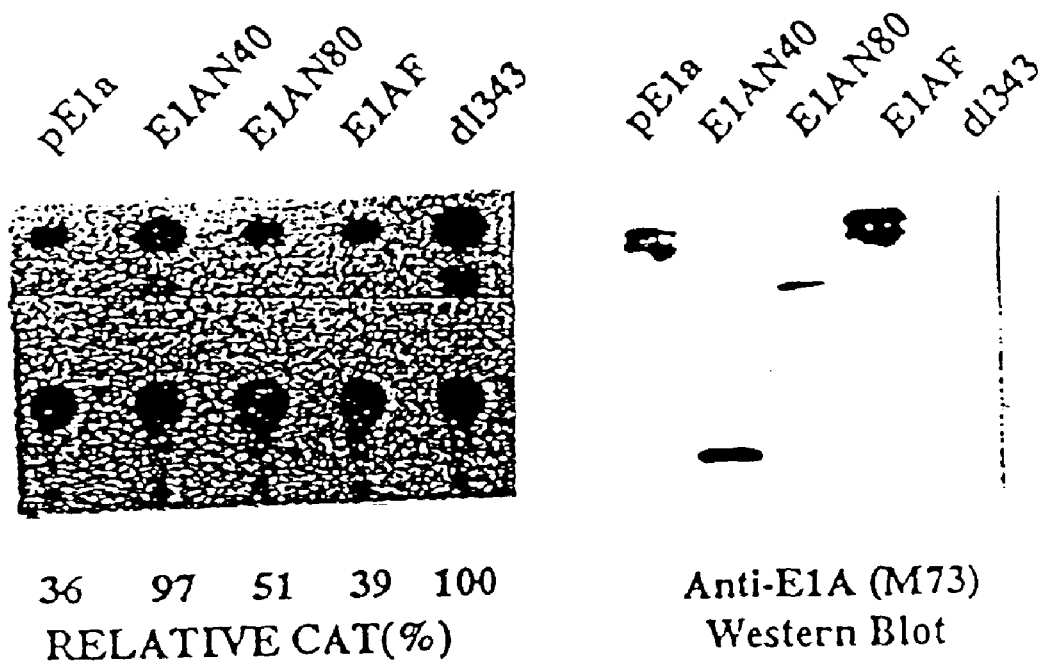
Figure 2C:
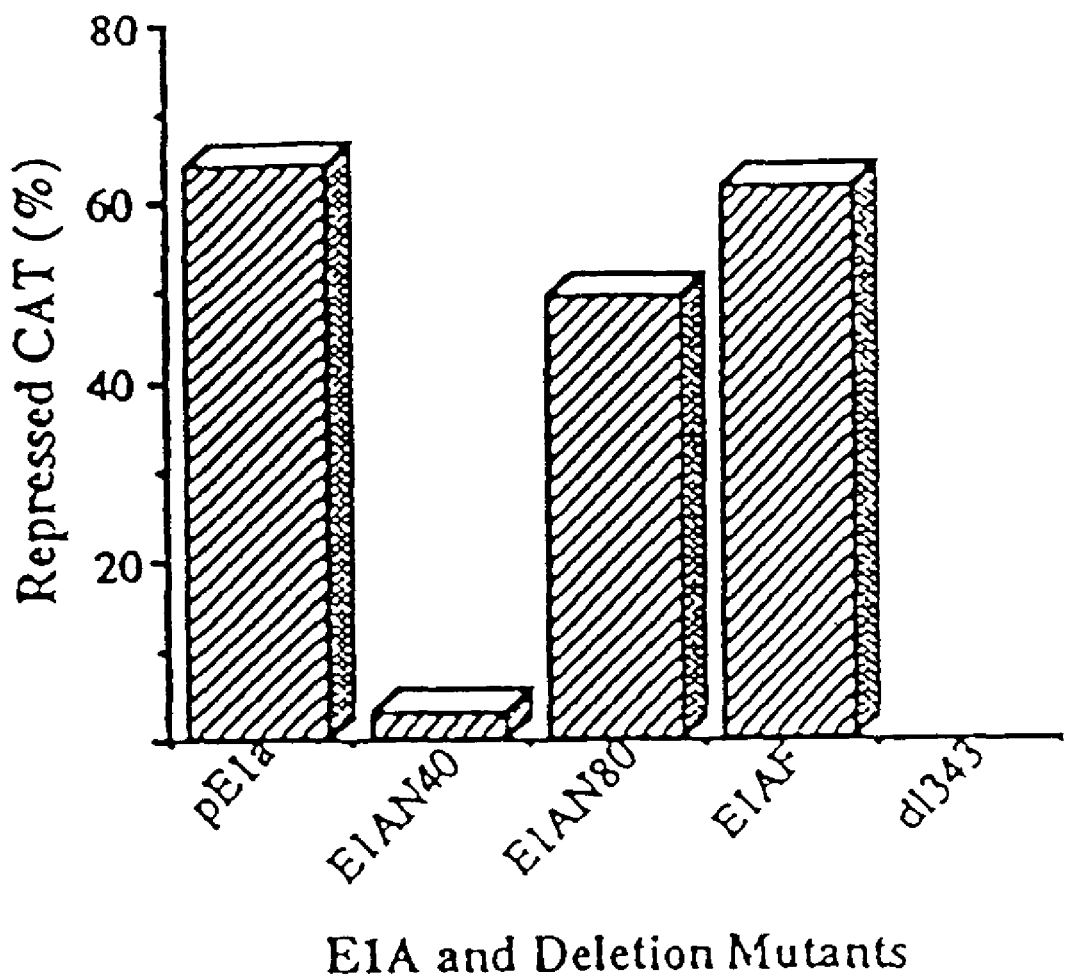

Next, the inventors constructed a mini-E1A mutant, termed E1AN80, in which the entire region from position 81–186 was ablated (removing amino acids 81–210, as well as the entire CR2 and CR3 domains). As shown in FIG. 2A, the E1AN80 mutant, which contained the entire CR1 domain still efficiently repressed neu promoter activity, compared with the plasmid DNA expressing wild type E1A proteins, pE1A or E1AF. Except for the pE1A containing a genomic E1A DNA driven by the E1A promoter (Chang et al, 1989), all the other constructs, i.e., E1AN80 and E1AF, were cloned into the same expression vector, pCDNAI (Invitrogen), and were confirmed by DNA sequencing. They expressed the proteins at a comparable level when they were transfected into NIH 3T3 cells (FIG. 2C).

The results indicated that some regions in CR1 (amino acid residues 48 to 60 or 70 to 80) are not required for repression of neu promoter activity. It is also clear that the E1AN80 construct represents a mini-E1A mutant that still represses neu expression yet does not contain the domains binding to the Rb protein (CR2) and transactivating other promoters (CR3) (Chen et al, 1997).

Figure 3:
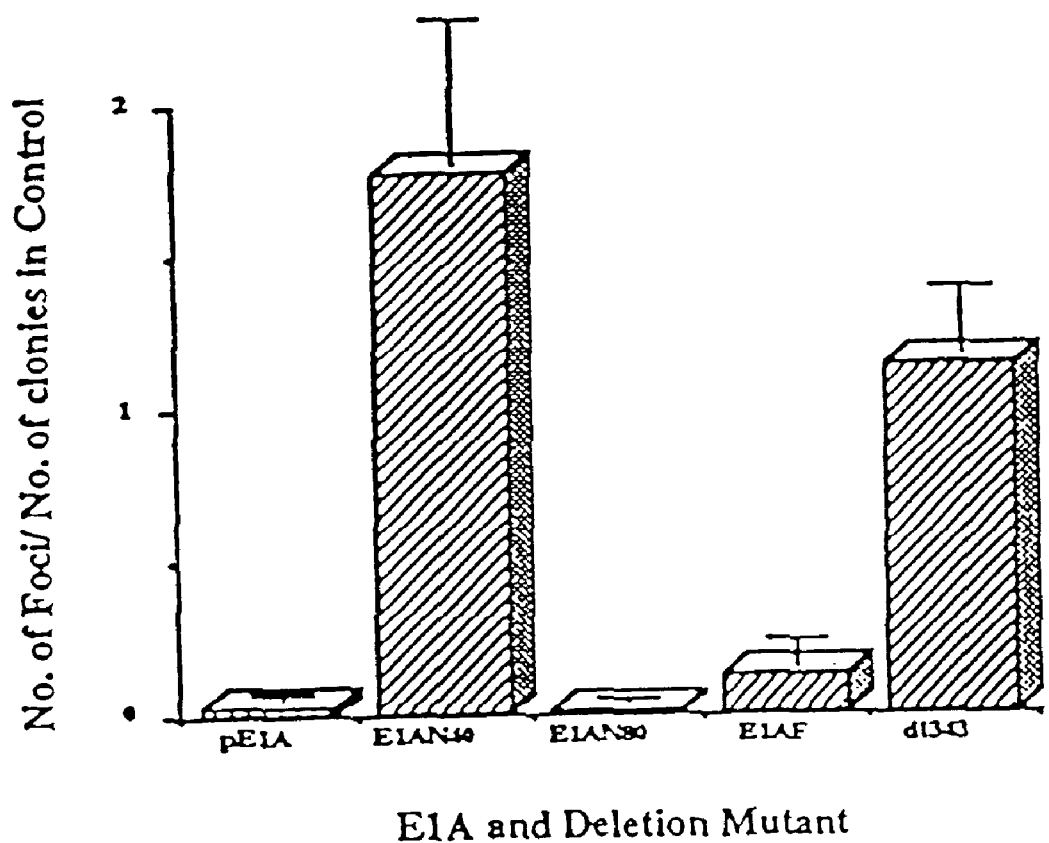
FIG. 3. Suppression of activated rat neu-mediated foci formation by mini-E1A. The cNeu-104 (1 μg) was cotransfected into NIH 3T3 cells along with 0.1 μg of the drug selection plasmid pSV2neo and 10 μg of the plasmids encoding E1A or deletion mutants. The number of foci formed for each transfection was normalized by dividing the foci number with G-418 colony number obtained from the same transfection. The results are shown as percentage of the normalized number of foci in each transfection versus that in control transfection (dl343). Data are the average from three independent experiments, and standard deviations are shown by error bars.

To further examine whether these mini-E1A mutants are able to suppress the transformation phenotype, we performed focus-forming assays by co-transfection of mini-E1A mutants and mutation-activated genomic rat neu (cNeu-104) into NIH 3T3 cells. The transfected DNA mixture also contained the pSV2neo plasmid for normalization of the transfection efficiency among each individual transfection. As shown in FIG. 3, the E1AN80 construct, like the wild type E1A, dramatically reduced foci formation in these transformed cells.

Reduction of neu-encoded p185 Level in the E1AN80 Stable Transfectants.

To test the mini-E1A mutant for its ability to down-regulate the neu-encoded p185 level and characterize its effects on transformation phenotypes, we also established stable transfectants of the mini-E1A mutant using B104-1-1 cells as recipients (which are NIH 3T3 cells transformed by a genomic rat mutation-activated neu oncogene). To this end, the inventors cotransfected the B104-1-1 cells with the E1AN80 construct and the pCMV-neo plasmid carrying the neomycin-resistance marker gene driven by the cytomegalovirus promoter.

Figure 4A:
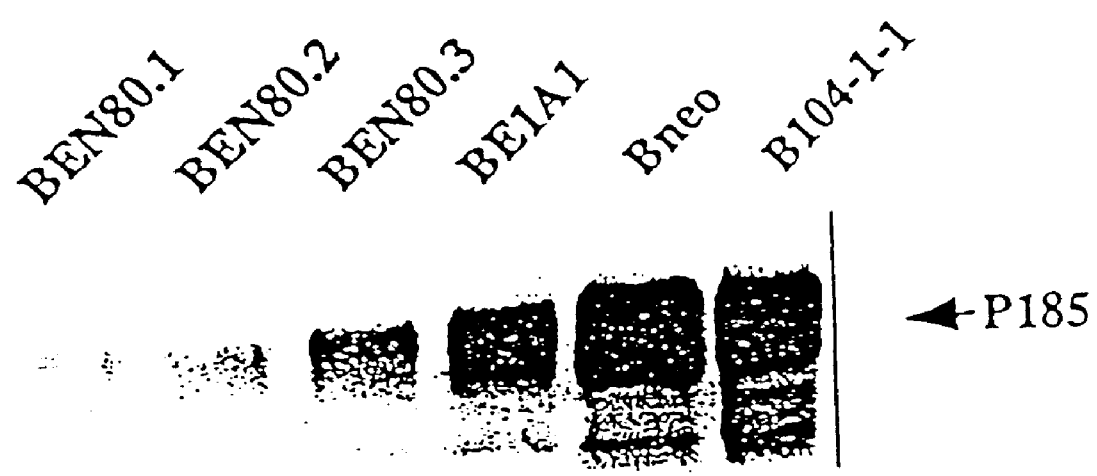
FIG. 4A, FIG. 4B and FIG. 4C. Reduction of the neu-encoded p185 level in mini-E1A stable transfectants. One hundred micrograms of protein was subjected to electrophoresis on 6% (FIG. 4A) or 8% (FIG. 4B and FIG. 4C) SDS-PAGE prior to transfer to nitrocellulose filters. Filters were incubated with the primary antibodies c-neu-Ab-3 against p185 (FIG. 4A), M73 against adenovirus E1A (FIG. 4B), and antibody against β-actin (FIG. 4C). BEN80 represented B104-1-1 cells transfected by E1AN80 mutants. BE1A1 was a previously established B104-1-1 transfected by the wild type E1A gene.
Figure 4B:
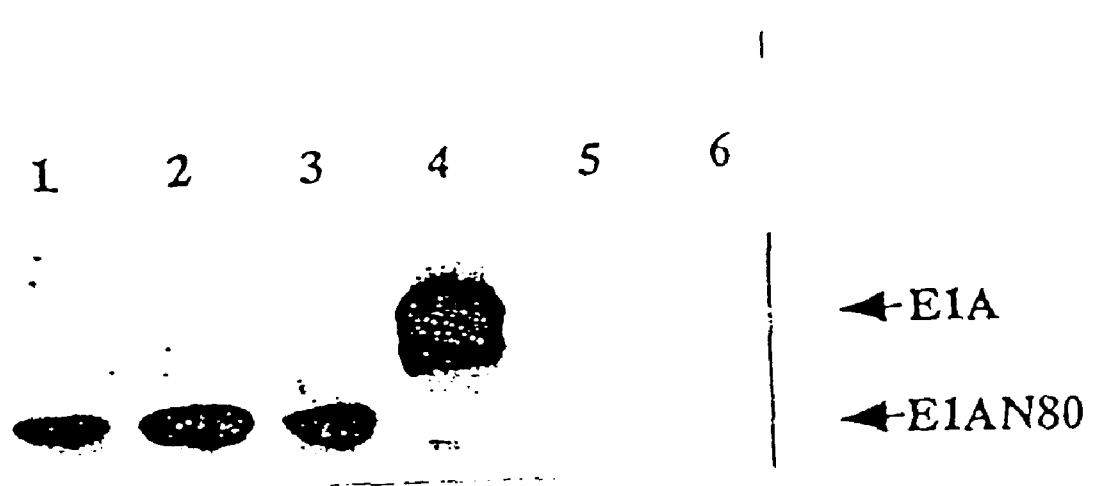

The G418-resistant clones were screened for E1A mutant protein expression and expanded into cell lines, which were designated BEN80 cell lines. To rule out the possibility that the changes in any of the biological behavior of the transfectants were due to artificial cell manipulation, two E1AN80 expressing transfectants (BEN80.1 and BEN80.2) selected from individual clones, and one transfectant (BEN80.3) pooled from a single plate containing more than 20 individual clones, were used in the following experiments. A transfectant with the vector backbone containing the neomycin-resistant gene but without E1AN80 was also selected as a negative control, and designated βneo. The expression of the E1AN80 mutants in these individual transfectants is shown in FIG. 4B. BE1A1 is a previously established B104-1-1 transfectant expressing wild type E1A proteins and down-regulated p185 proteins.

Figure 4C:
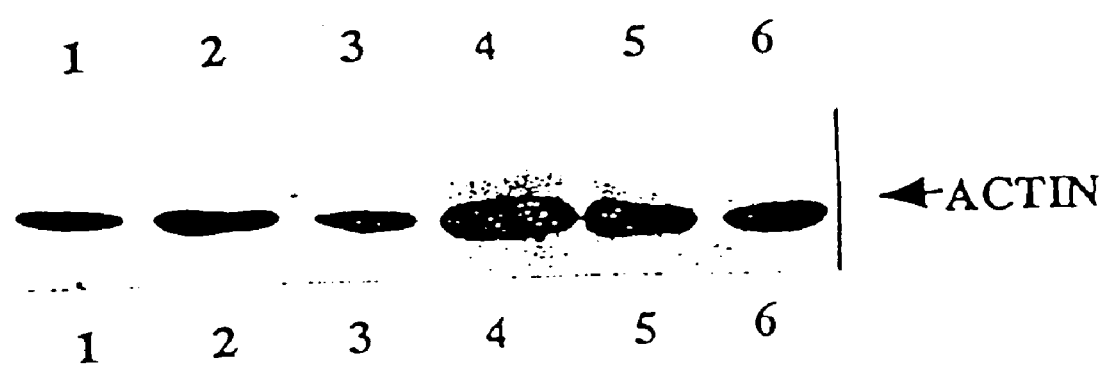

To determine whether expression of E1AN80 in BEN80 transfectants affected the neu-encoded p185 expression, immunoblot analysis of neu-encoded p185 protein using monoclonal antibodies against neu-(c-neu-Ab3) was performed. The p185 protein levels in all the mini-E1A transfectants were dramatically reduced compared to those of the control βneo cell line and the parental B104-1-1 cell line (FIG. 4A). The amount of protein loading is comparable as shown in FIG. 4C by western blot analysis using monoclonal antibodies against a β-actin protein. These results indicated that the E1AN80 mutant is able to repress p185 expression, consistent with the fact that it inhibits the neu promoter activity.

Reversion of Transformation Phenotypes in E1AN80 Transfectants.

Figure 5A:
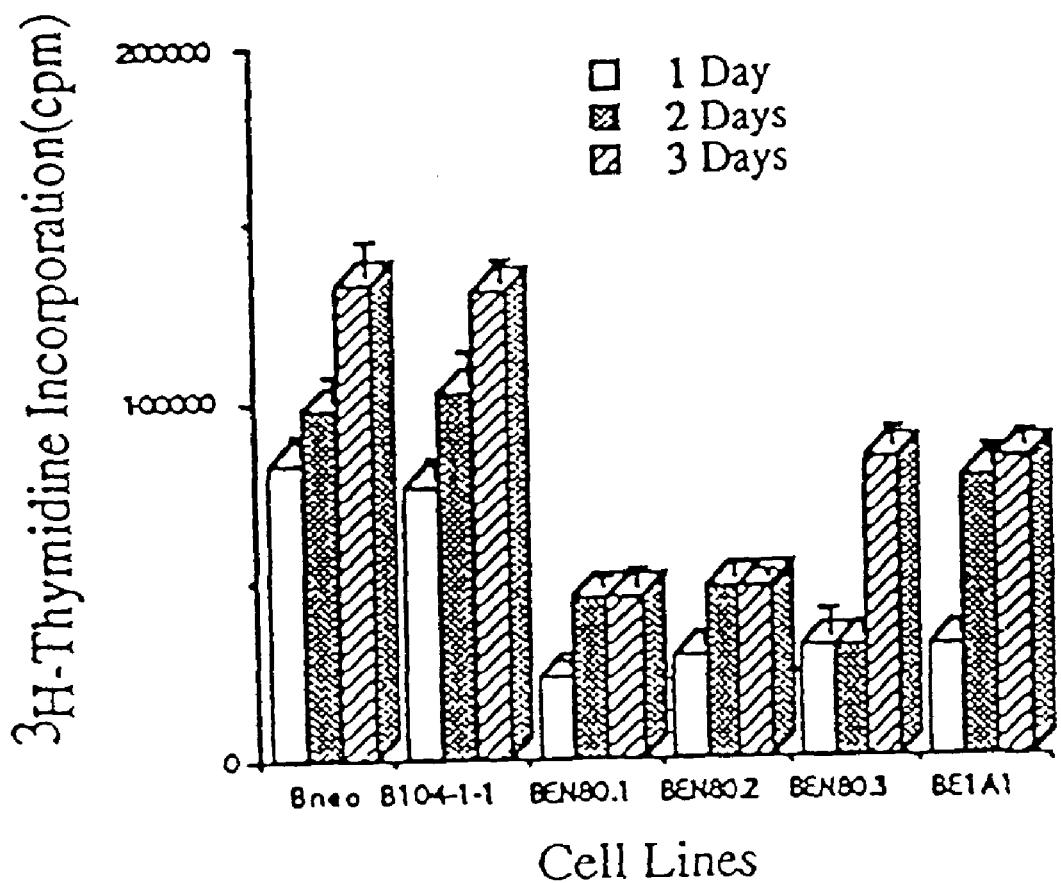
FIG. 5A, and FIG. 5B. Reduced cell growth rate of mini-E1A stable transfectants.
Figure 5B:
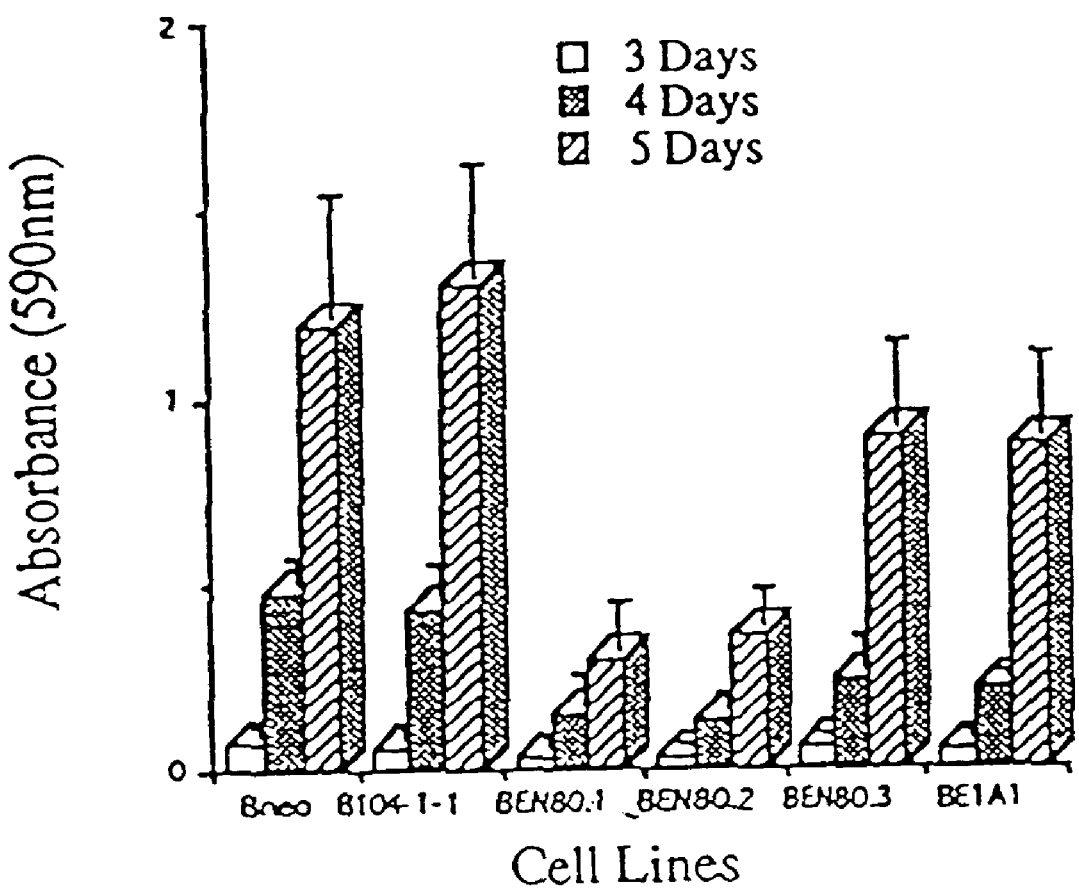
Figure 6:
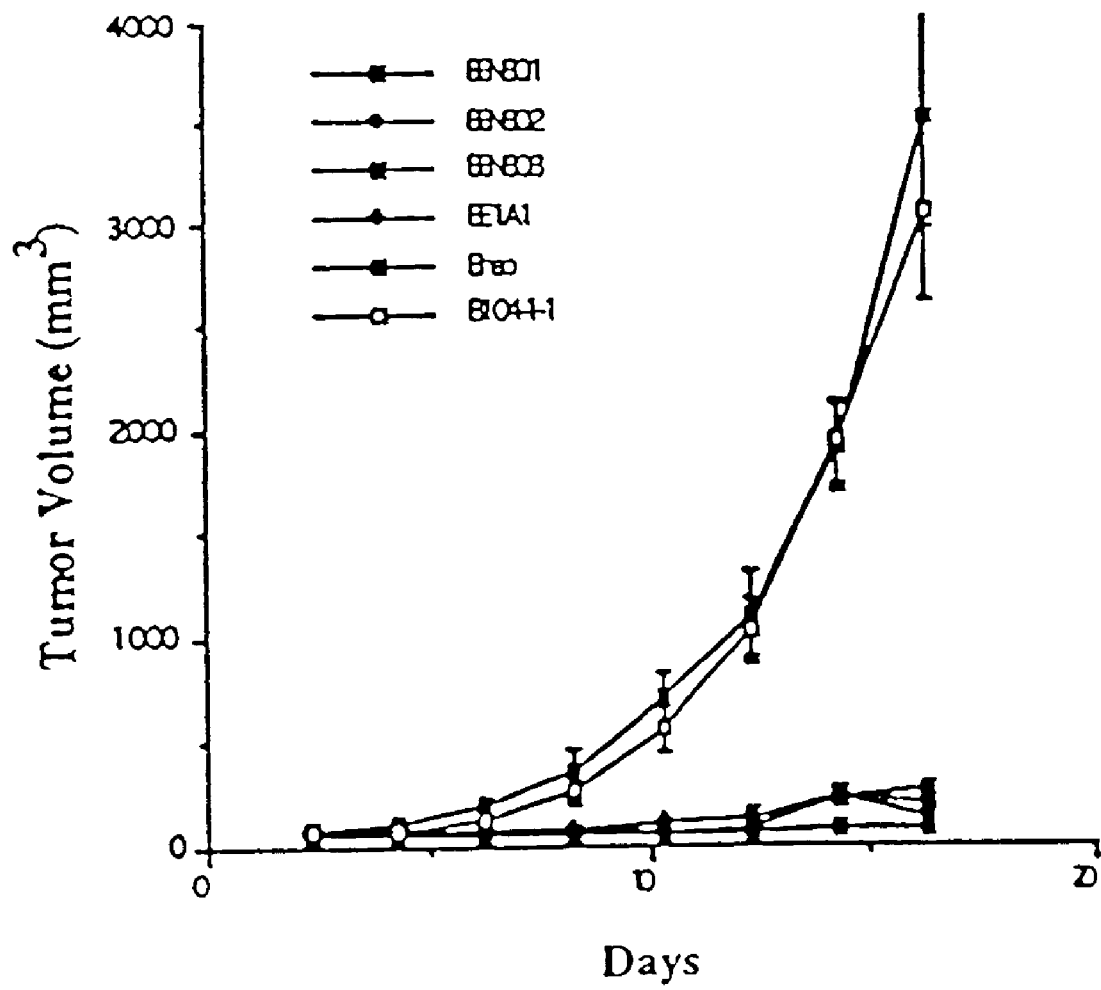
FIG. 6. Suppression of tumor formation by a mini-E1A gene product. Viable cells ($3 \times 10^6$) were injected into right and left flanks of female homozygous nu/nu mice. Five mice were injected for each cell line. Tumor formation was scored at indicated days, and tumor volumes were estimated as the product of three-dimensional caliper measurements. Tumor volumes from mice injected with the indicated cell lines at the indicated days are shown with standard deviation.

To initially analyze if there were any biological changes in the BEN80 cells, the inventors characterized the transformation phenotype using in vitro assays. First, the cell growth rates were measured by $^3$H-thymidine incorporation assay and MTT assay. The growth rates of the BEN80 transfectants were lower than those of the control Pneo and parental cell B 104-1-1 (FIG. 5A and FIG. 5B). The anchorage-independent growth abilities (measured by soft agar colonization assay) of these transfectants were also measured. Both the neu- transformed B104-1-1 cells and the control Bneo cells exhibited high efficiency formation of soft agar colonies, whereas the colony-forming efficiencies of the three BEN80 transfectants were strikingly reduced. These data show that E1AN80 proteins can suppress the transformation-associated property of anchorage-independent growth. Taken together, these data indicated that the in vitro transforming phenotype of the B104-1-1 cells was largely reversed by transfection of the E1AN80 mutant.

Figure 7:
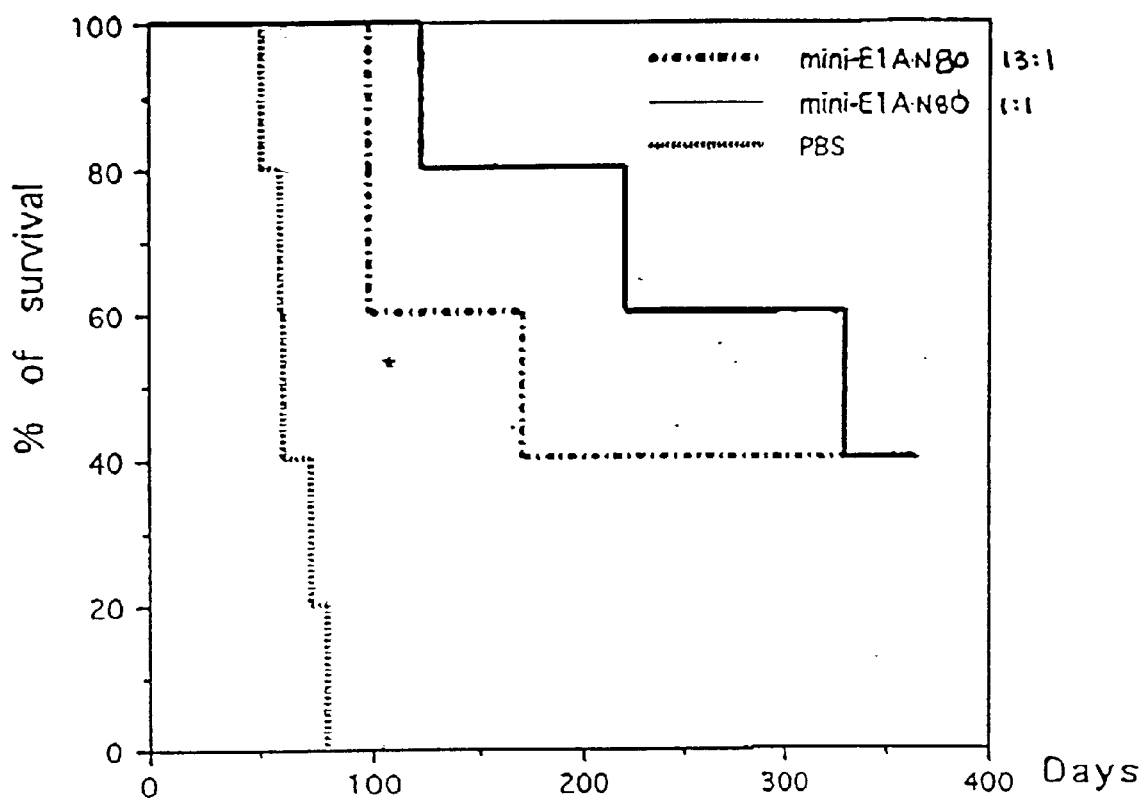
FIG. 7. Tumor suppression activity of mini-E1AN80. Mice were injected intraperitonealy with SKOV-3.ip1 cells five days before treatment. Mice were divided into groups of 5 and each group received one of the following treatment regimens: A)15 µg mini-E1AN80 DNA complexed with 200 nmoles of liposome, B) 15 µg mini-E1AN80 DNA complexed with 15 nmoles of liposome, or C) PBS. Injections of treatment formulations were performed 3 times the first week and once a week thereafter. The responses were followed for one year. The asterisk (*) marks the last treatment injection.

Confirmation that the E1AN80 mini-gene could suppress the transformation phenotype was obtained by analyzing tumor formation in vivo. The tumorigenicity assays were conducted in nu/nu mice that were injected s.c. with $3 \times 10^6$ cells from BEN80 transfectants, the control E1A wild type transfectant, Bneo cell line, and B104-1-1 cell, respectively (FIG. 7). Like mice injected with the parental B104-1-1 cells, mice injected with the control Bneo cells generally formed tumors 2 days after injection and had huge tumor burdens of 4000 mm$^3$ by 2 weeks post-injection. However, mice injected with the same number of BEN80 transfectants did not form tumors in nude mice until 1 week after injection, and the tumor size was much smaller than the tumors formed from B104-1-1 and Bneo cells. These results clearly indicated that the E1AN80 mini-gene also can suppress the tumorigenic potential of transformed cells in vivo.

Discussion

As noted above, a mini-E1A gene (E1AN80), which deleted the E1A CR2 and CR3 domain, as well as an additional portion of the N-terminal domain, was sufficient for transcriptional repression of the neu gene as well as a reduction of the transformation phenotypes.

In that regard, wild-type E1A can apparently bind to multiple cellular regulators and mediate multiple cellular events. The E1A CR2 domain is known to be able to bind to Rb family proteins, which led to immortalization of the cells and further transformation of primary culture cells via cooperation with ras or E1B oncogenes (Corbeil and Branton, 1994; Whyte et al., 1989). Deletion of the CR2 domain or even a small mutation to knock out the Rb-binding site on E1A, such as mutant dl1108, which deleted the Thr123 and lost the binding ability to Rb, is apparently sufficient to abolish E1A's immortalization function (Jelsma et al., 1989; Whyte et al., 1989; Zerler et al., 1986; Zerler et al., 1987; Schneider et al., 1987; Lillie et al., 1986; Moran et al., 1986; Kuppuswamy and Chinnadurai, 1987; Smith and Ziff, 1988). The E1A CR3 domain binds to ATF-2 (Liu and Green, 1994) or p53-associated protein such as TBP proteins (Horikoshi et al., 1995). The binding of the CR3 domain with TBP disrupted the association between the carboxy-terminal domain of p53 with TFIID, relieving transcriptional repression mediated by p53 tumor suppressor protein. This may be a key mechanism of transcriptional activation in adenovirus-infected cells (Horikoshi et al., 1995). The CR3 domain was also known to transactivate some viral oncogenes such as the E1B gene and certain cellular genes such as heat shock genes, which are essential for productive infection (Flint and Shenk, 1989).

The present invention shows that the E1AN80 mutant deleting both CR2 and CR3 domains, as well as an additional portion of the N-terminal domain, is sufficient for suppression the transformation phenotype. This result demonstrated that domains of E1A associated with immortalization and transcription activation are apparently not required for repression of the neu gene or suppression of tumorigenesis. We have previously shown that the E1A mutant dl346, which deleted the nucleotides 859–907, was unable to repress neu, suggesting that this region may be required for neu repression. This region (the nucleotides 859–907), which was mistakenly interpreted as the CR2 domain in previous reports, actually encoded the spacer region between CR1 and CR2 (Yu et al., 1990). These data show that this region is not absolutely required for repression of neu, as the E1AN80 mutant does not contain this region and still represses neu. Hence this region may sometimes be of help to provide a correct conformation for the E1A gene product, but itself may not be directly involved in the function of neu repression.

As described in further detail below, we have also tested a smaller construct called "E1A-Cterm", which has only a C-terminal portion of the E1A sequence that is present in E1AN80, but which appears to be sufficient for providing a substantial tumor suppression effect as assayed in a mouse cancer model.

EXAMPLE II

DELIVERY OF DNA INTO ONCOGENIC CELLS VIA LIPID-BASED COMPLEXES

One particularly useful way to use mini-E1A, E1A and/or LT to repress neu-mediated phenotypes is via the use of lipid-based complexes for carrying the suppressor's DNA into the oncogenic cells.

Preparation of Lipid-based Complexes

Lipid-based complexes, such as cationic lipid complexes, which are efficient transfection reagents for the mini-E1A, E1A and LT genes for animal cells can be prepared using the methods of Gao et al. (1991) and of Huang and collaborators (cited above). Gao et al. describes a novel cationic cholesterol derivative that can be used for gene delivery. Complexes made of this lipid are reportedly more efficient in transfection and less toxic to treated cells than those made with other reagents such as Lipofectin. Exemplary lipids are a mixture of DC-Chol ("3β(N-(N'N'-dimethylaminoethane)-carbamoyl cholesterol") and DOPE ("dioleoylphosphatidylethanolamine"). The steps in producing these complexes are as follows.

As described by Huang and collaborators, DC-Chol can be synthesized by a simple reaction from cholesteryl chloroformate and N,N-dimethylethylenediamine. A solution of cholesteryl chloroformate (2.25 g, 5 mmol in 5 ml dry chloroform) is added dropwise to a solution of excess N,N-dimethylethylenediamine (2 ml, 18.2 mmol in 3 ml dry chloroform) at 0° C. Following removal of the solvent by evaporation, the residue is purified by recrystallization in absolute ethanol at 4° C. and dried in vacuo. The yield is a white powder of DC-Chol. Cationic lipid complexes can be prepared by mixing 1.2 μmol of DC-Chol and 8.0 μmol of DOPE in chloroform. This mixture is then dried, vacuum desiccated, and resuspended in 1 ml sterol 20 mM HEPES buffer (pH 7.8) in a tube. After 24 hours of hydration at 4° C., the dispersion is sonicated for 5–10 minutes in a sonicator form complexes with an average diameter of 150–200 nm.

To prepare a lipid/DNA complex, the inventors use the following steps. The DNA to be transfected is placed in DMEM/F12 medium in a ratio of 15 μg DNA to 50 μl DMEM/F12. DMEM/F12 is then used to dilute the DC-ChoUDOPE lipid mixture to a ratio of 50 μl DMEM/F12 to 100 μl lipid. The DNA dilution and the lipid dilution are then gently mixed, and incubated at 37° C. for 10 minutes. Following incubation, the DNA/lipid complex is ready for injection.

In Vivo Treatment of Cancer Using Lipid-based Gene Delivery

Hung et al. have shown that lipid-mediated direct gene transfer techniques can be employed to obtain E1A suppression of human cancer cells in living host (Yu et al., 1995). Here we show that mini-E1A genes can be used as well. The protocol for such a study was as follows.

Female nude mice (5–6 weeks old) were given intraperitoneal injections of SKOV-3 cells ($2 \times 10^6$/100 μl). SKOV-3 cells are human ovarian cancer cells that have been shown to grow within the peritoneal cavity of nude mice. After five days, the mice were given intraperitoneal injections of various compounds. One group of mice was injected with E1A DNA alone, a second group was injected with lipid/E1A DNA complex prepared in the manner described above, and a third group was injected with lipid/Efs DNA complex (Efs refers to an E1A rendered non-functional by a frameshift mutation). 200 μl of a given compound was injected into a given mouse. After the initial injections, injections were repeated every seven days throughout the life of the mouse.

In one such study, as reported by Yu et al., 1995, seven mice in a first group were injected with E1A DNA alone; 12 mice in a second group were injected with lipid/Efs DNA complex; and 12 mice in a third group were injected with lipid/E1A DNA complex. By day 200, 70% of the mice in Group 3 (lipid/E1A) were still alive, but all other mice developed severe tumor symptoms and had died or were sacrificed when their tumor burden rendered them moribund. Upon further observation of the E1A-treated mice that survived to day 200, all were still alive at day 365.

These observations indicate that lipid-mediated E1A gene transfer can inhibit human ovarian cancer cell growth. Therefore, it is expected that lipid-mediated E1A or LT gene therapy may serve as a powerful therapeutic agent for human ovarian cancers.

Lipid-based Transfection With Mini-E1A, E1A and/or LT to Treat Humans

Based on the results of the in vivo animal studies described above, those of skill in the art will understand and predict the enormous potential for human treatment of cancers with mini-E1A, E1A and/or LT DNA complexed to lipids. Indeed, as noted above, success in the animal models has merited the approval and initiation of Phase I human clinical trials which are now ongoing at a number of centers. It is expected that these clinical trials will confirm the use of mini-E1A, LT, E1A, and other tumor-suppressing gene products for the treatment of cancers in humans. Dosage and frequency regimes will initially be based on the data obtained from in vivo animal studies, as was described above.

The treatment of human cancers is possible by the introduction of the mini-E1A, E1A or LT gene. This may be achieved most preferably by introduction of the desired gene through the use of a viral or non-viral vector to carry either the mini-E1A, E1A or LT sequences to efficiently infect the tumor, or pre-tumorous tissue. Viral vectors will preferably be an adenoviral, a retroviral, a vaccinia viral vector or adeno-associated virus (Muro-cacho et al, 1992). These vectors are preferred because they have been successfully used to deliver desired sequences to cells and tend to have a high infection efficiency. Hung et al. have conducted studies showing that native adenovirus can be employed to transfer the E1A gene in accordance with the invention. However, a particularly preferred type of adenovirus is the group of replication-deficient adenoviruses.

As noted above, the HER-2/neu oncogene encodes a MW 185,000 epidermal growth factor receptor-related transmembrane protein (p185) with intrinsic tyrosine kinase activity. Overexpression of the normal human HER-2/neu proto-oncogene, which can also lead to higher overall tyrosine kinase activity, is a frequent event in many types of human cancers, including cancers of the breast, ovarian, lung, uterine cervix, stomach and colon cancer, for example. Correlation between the overexpression of HER-2/neu and the number of lymph node metastases in breast cancer patients and decreased survival in both breast and ovarian cancer patients has been reported. Hung et al. have shown that adenovirus 5 E1A gene product can repress HER-2/neu oncogene expression and suppress the tumorigenic and metastatic potential of activated rat neu oncogene-transformed mouse 3T3 cells. Introduction of the E1A gene into the human ovarian cancer cell line SKOV-3(i.p.), which has enhanced expression of HER-2/neu, resulted in reduced malignant phenotypes in vitro and in vivo. Those data indicated that the E1A gene can be considered as a tumor suppressor gene for human cancer cells.

As also noted above, studies by Frisch et al. have indicated that E1A can also bring about tumor suppression in cells that do not appear to be over-expressing the neu oncogene, suggesting that E1A can mediate tumor suppression via multiple pathways. Regardless of the precise mechanism of action, it is apparent that E1A brings about tumor suppression in a variety of different cancer cell types, and that the mini-E1A products of the present invention are therefore expected to be useful in a variety of different cancer cells.

Replication-deficient adenovirus represents a gene delivery system that should be able to efficiently transfer an exogenous gene directly to tumor cells in vivo. Unlike vectors that require target cell replication for gene transfer, such as retrovirus which can only infect proliferating cells, adenovirus can transfer genes into both proliferating and non-proliferating cells. The extrachromosomal location of adenovirus in the cells (non-integration) decreases the chance of activating cellular oncogenes. A high titer of adenovirus is easily produced and purified. Replication-deficient adenovirus containing E1A was constructed by E3 and E1B deletion mutant (E1B and E3 is required for adenovirus replication), control virus was constructed by additional E1A deletion mutant.

Hung et al. have shown that tumor suppressor gene E1A is efficiently transduced into human ovarian cancer cell SKOV-3(i.p.) cells by Ad.E1A(+) in vitro and in vivo (Zhang et al., 1995). Up to 100% of the cells can be infected at either the virus/tumor ratio>50/1 or at lower ratios with multiple infections. Tumor growth in vitro and colony formation ability in soft agarose were greatly inhibited by Ad.E1A(+).

SKOV-3(i.p.) ($10^6$/mouse) was transplanted into the peritoneal cavity of nu/nu mice. Five days later they received an intraperitoneal injection of viral solution (titer: $2 \times 10^9$ PFU/ml) from either Ad.E1A(+), Ad.E1A(−), or Just PBS for 3 days, followed by once/week for 4.5 months. Clinical observation and survival rates showed that Ad.E1A(+) significantly prolonged the survival time of the mice and some mice were kept tumor free. Immunohistochemical analysis indicated that Ad.E1A protein was expressed in tumor tissue after gene delivery in vivo and expression of HER-2/neu P185 protein was greatly suppressed.

An orthotopic human lung cancer model in nu/nu mice has also been used to study the effect of Ad.E1A(+) on tumor growth of human lung cancer cell line NCI-H820. Mouse tumor cells ($5 \times 10^6$), were inoculated intratracheally. Five days later, mice were treated by intratracheal instillation of viral solution (titer: $2 \times 10^9$ PFU/ml) of Ad.E1A(+), Ad.E1A(−), or PBS, followed by once/week i.v. injection treatment for 2.5 months. At autopsy, more than 80% of control mice but only 20% of treated mice had tumors.

Human non-small cell lung cancer line NCI-H820 was injected intratracheally into nu/nu mice ($5 \times 10^6$/mouse) via a tracheotomy incision. Five days later, the mice were treated once with intratracheal injection (0.1 ml) of either PBS, or Ad.E1A(−), Ad.E1A(+) (Viral titer: $2 \times 10^9$ PFU/ml), followed by weekly i.v. injection treatment for 2.5 months. Then, mediastinal blocks were removed and tumor volume was calculated. The results indicate that Ad.E1A(+) can prevent the growth of human lung cancer cells implanted orthotopically in nu/nu mice.

From the above observations, it is clear that lipid-based, as well as adenoviral, gene delivery systems are effective and that E1A has a therapeutic effect on human ovarian and lung cancer tumor cells.

EXAMPLE III

IN VIVO USE OF MINI-E1A GENE PRODUCTS

In an initial round of in vivo trials, inventors have used a mouse model of human cancer with the histologic features and metastatic potential resembling tumors seen in humans (Katsumata et al., 1995) and treated these animals with mini-E1A to examine the suppression of tumor development.

These studies are based on the discovery that mini-E1A has tumor suppressor activity, as noted above. The Examples above further show that E1A inhibits the growth of cancer cells and furthermore sensitizes cancer cells to chemotherapeutic drugs. The current example uses mini-E1A, either alone or in combination with chemotherapeutic drugs and/or emodin-like tyrosine kinase inhibitors, to provide a useful preventive and therapeutic regimen for patients with cancers.

Two groups of mice of a suitable cancer model are treated with doses of mini-E1A in combination with anti-cancer drugs and/or emodin like tyrosine kinase inhibitors starting at 6 weeks of age. Several combinations and concentrations of mini-E1A and anti-cancer drugs are tested. Control mice are treated with buffer only.

The effect of mini-E1A, in combination with an anticancer drug and/or emodin like tyrosine kinase inhibitors, on the development of breast tumors is then compared with the control group by examination of tumor size, p185 tyrosine kinase activity (using IP-western blot analysis) and histopathologic examination (breast tissue will be cut and stained with hematoxylin and eosin) of breast tissue. With the chemopreventive potential of mini-E1A, it is predicted that, unlike the control group of mice that develop tumors, the testing group of mice will be resistant to tumor development.

Breast Cancer Model

In order to obtain mice having human breast cancer, nu/nu mice may be given intraperitoneal injections of, for example, $2 \times 10^6$ viable breast cancer cells from cell line MDA-MB-361 are injected in the mammary fat pad in nude mice. Palpable solid tumors are detected 1.5 months later.

These mice may then be given an appropriate dosage of mini-E1A using methods of delivery described above; in combination with an anti-cancer drug and/or emodin-like tryosine kinase inhibitor for 3 consecutive days, then once a week for six months.

Ovarian Cancer Model

In order to obtain mice having human ovarian cancer, nu/nu mice may be given intraperitoneal injections of, for example, $2 \times 10^6$ viable SKOV-3 human ovarian cancer cells. Mice sacrificed 5 days post treatment exhibit tumors resulting from such treatment.

Five days after treatment with the cancer cells, mice may be separated into control and experimental groups. One group of mice will be left untreated. Other groups will be treated. Active compounds may be supplied to a treated group in phosphate buffer saline. One treated group will be treated with the buffered saline only. Another treated group may receive treatment with an appropriate dosage of mini-E1A. A third treated group may be treated with an appropriate dosage of an anti-cancer drug alone. A final group may be treated with an appropriate dosage of mini-E1A in combination with an anti-cancer drug. Any of the previous groups may also include a suitable composition of an emodin-like tyrosine kinase inhibitor. Treatments may be given using any of the methods described above.

Mice may be examined for tumor signs and symptoms, and killed when they appear moribund. Mice treated with the E1A or LT plus the anti-cancer drug and/or emodin like tyrosine kinase inhibitors will be expected to have a longer survival time.

Small Cell Lung Cancer Model

In order to obtain mice with the human lung cell cancer, nu/nu mice may be given as intratracheal injections of, for example, $2 \times 10^6$ viable cancer cells from cell line H82. Five days after inoculation, following tumor formation, mice may be separated into groups to begin treatment. One group may be treated with an appropriate dosage of E1A or LT alone, another with an appropriate dosage of an anti-cancer drug alone. A third group may be treated with an appropriate dosage of E1A or LT in combination with an anticancer drug for 3 consecutive days, then once a week for two months. Of course any of these treatment groups may include an emodin-like tyrosine kinase inhibitor as part of the treatment regimen.

EXAMPLE IV

USE OF A MINI-E1A GENE (E1AN80) TO SUPPRESS TUMORIGENESIS IN A LONG-TERM SURVIVAL STUDY

Long-term survival studies to assess the tumor suppressor activity of mini-E1AN80 have now confirmed the ability of mini-E1AN80 to suppress tumor formation in mice as described in Example 1 (see FIG. 7). Results from both of these studies thus indicate that mini-E1AN80 appears to be useful, as is E1A, for tumor suppression in vivo.

As described in Example 1, the mini-E1AN80 construct contains a portion of the N-terminus, the CR1 domain and the C-terminus of the full-length E1A polypeptide (FIG. 2A). Mini-E1AN80 lacks the central portion of E1A from amino acids 81 to 185 which includes the CR2 and CR3 domains.

The protocol for tumor engraftment and lipid-DNA complex formation for the long-term survival studies were performed as described above. Five mice were used in each group. In these studies, the ovarian carcinoma cell line SKOV-3.ip1 was used to induce tumors in the mice. SKOV-3.ip1 is derived from the SKOV-3 cell line and correlates with more rapid progression of peritoneal carcinomatosis and a higher degree of malignancy than SKOV-3 cells.

After 5 days of tumor cell growth, injection of treatment compounds began with three injections the first week and subsequent injections were given every 7 days. Mini-E1AN80 was administered in two lipid:DNA formulations, namely, 13 nmole lipid:1 μg DNA and 1 nmole lipid:1 μg DNA. In each formulation, each injection contained 15 μg of DNA. Data from this experiment is presented as survival curves in FIG. 7.

Figure 8:
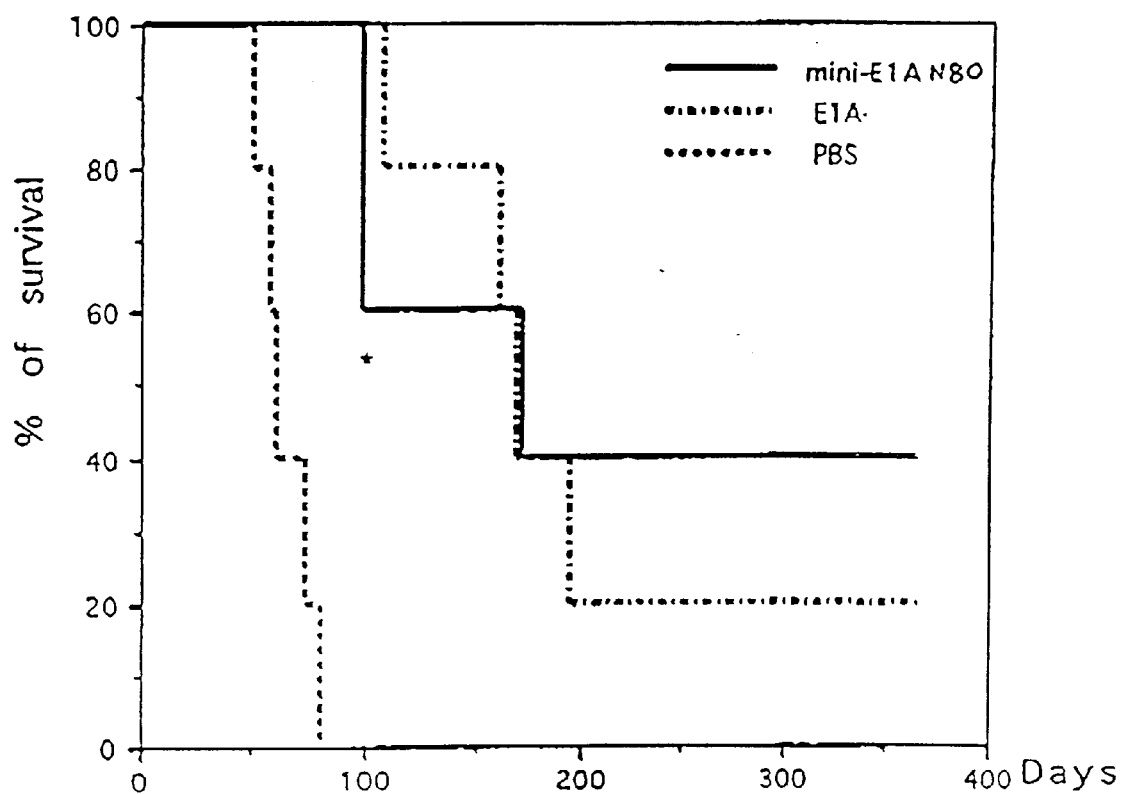
FIG. 8. Comparison of tumor suppressor activity of full-length E1A and mini-E1AN80. The mini-E1AN80 13:1 formulation data from FIG. 7 is here presented relative to full-length E1A (13:1) data. As shown, mini-E1AN80 is as potent in tumor suppression as full-length E1A.

As can be seen in FIG. 8, injections with mini-E1AN80 significantly prolonged mouse survival in both 13:1 and 1:1 formulations (mini-E1AN80–13 vs. PBS, $P<0.025$). The day on which the last surviving animal from the control group died was also the last day of treatment injections, indicated by an asterisk (*) in FIG. 7. At this time point, 8/10 animals that had received mini-E1AN80 injections were still alive, as compared to 0/5 of those that had received PBS injections. Even though treatment injections were discontinued after approximately 110 days, 4 out of 10 animals that received mini-E1AN80 injections were still alive after one year, long after all of the control animals had died.

In another long-term study, tumor suppressor activity of mini-E1AN80 was compared to that of full-length E1A in mice bearing SKOV-3 tumors. The full-length E1A constructs were mixed with cationic lipids at a 13:1 ratio and the experiment was performed as described above. The resultant survival curves, shown in FIG. 8, reflect the same mini-E1AN80 data discussed above (FIG. 7) along with the full-length E1A data. These results indicate that mini-E1AN80 appeared to be about as potent in tumor suppression as full-length E1A.

As shown in these studies, the therapeutic efficacy of mini-E1AN80 in which both CR2 and CR3 domains are deleted, is comparable to that of full-length E1A in a gene therapy setting in vivo. As described above, E1A is a multifunctional protein with distinct activities assigned to different 10 domains of the polypeptide. For example, as noted above, the CR2 domain is apparently involved in E1A interaction with Rb protein and the CR3 domain is involved in transcriptional activation. Deletion of these domains from E1A thus help eliminate effects associated with these domains. Since mini-E1AN80 is comparable to full-length E1A in tumor suppression, and yet lacks other domains of full-length E1A, mini-E1AN80 may serve as a particularly beneficial therapeutic agent for treatment of cancer cells.

EXAMPLE V

USE OF A SECOND MINI-E1A GENE (E1A-CTERM) TO SUPPRESS TUMORIGENESIS IN A LONG-TERM SURVIVAL STUDY

Long term survival studies using an additional mini-E1A construct provided additional information supporting the utility of mini-E1A formulations in the treatment of cancers.

The mini-E1ACterm construct of this example is partly similar to the E1AN80 construct described in Example 1, but contains only the C-terminus of E1A. In particular, mini-E1ACterm contains DNA which could encode only amino acids 186–289 of E1A in the context of the plasmid vector pcDNA1.1. However, the actual polypeptide expressed from the mini-E1ACterm construct is expected to be even smaller than the 186–289 C-terminus. Specifically, as cloned in the vector, the first methionine codon (and thus the likely translation initiation site) is amino acid 209 (in reference to the amino acid number of full-length E1A 13S). It is likely, therefore, that the mini-E1ACterm construct produces a mini-E1A polypeptide roughly 23 amino acids less than what is described as the C-terminus in Example I and FIG. 2A. The predicted amino acid sequence, as shown below in SEQ ID NO. 1, is thus only about 80 amino acids in length.

```
SEQ ID NO:1:

CCTGTGTCTG AACCTGAGCC TGAGCCCGAG CCAGAACCGG AGCCTGCAAG ACCTACCCGC 60

CGTCCTAAA ATG GCG CCT GCT ATC CTG AGA CGC CCG ACA TCA CCT GTG TCT 111
           Met Ala Pro Ala Ile Leu Arg Arg Pro Thr Ser Pro Val Ser
           1               5                   10

AGA GAA TGC AAT AGT AGT ACG GAT AGC TGT GAC TCC GGT CCT TCT AAC  159
Arg Glu Cys Asn Ser Ser Thr Asp Ser Cys Asp Ser Gly Pro Ser Asn
15                  20                  25                  30
```

-continued

```
ACA CCT CCT GAG ATA CAC CCG GTG GTC CCG CTG TGC CCC ATT AAA CCA    207
Thr Pro Pro Glu Ile His Pro Val Val Pro Leu Cys Pro Ile Lys Pro
             35              40                  45

GTT GCC GTG AGA GTT GGT GGG CGT CGC CAG GCT GTG GAA TGT ATC GAG    255
Val Ala Val Arg Val Gly Gly Arg Arg Gln Ala Val Glu Cys Ile Glu
             50              55                  60

GAC TTG CTT AAC GAG CCT GGG CAA CCT TTG GAC TTG AGC TGT AAA CGC    303
Asp Leu Leu Asn Glu Pro Gly Gln Pro Leu Asp Leu Ser Cys Lys Arg
             65              70                  75

CCC AGG CCA TAA                                                    315
Pro Arg Pro
 80
```

Long-term survival studies were performed using the E1A-Cterm mini-gene in a tumor engraftment model and DNA-lipid formulations as described above. In this study, it appears that the subclone of SKOV-3.ip1 used may have been even more aggressive in tumor formation than the SKOV-3.ip1 parent used to induce tumors in the nude mice since no control mice survived for more than about 35 days. The protocol was otherwise as in the long-term study above except that: (i) 10 mice were used in each group receiving E1A formulations and 9 mice were used in the control group; (ii) 5% dextrose was used for control injections; and (iii) a lipid:DNA ratio of 10:1 w as used for the treatment formulations however, as above, each injection contained 15 µg of DNA. Survival curves from this experiment are shown in FIG. 9.

Figure 9:
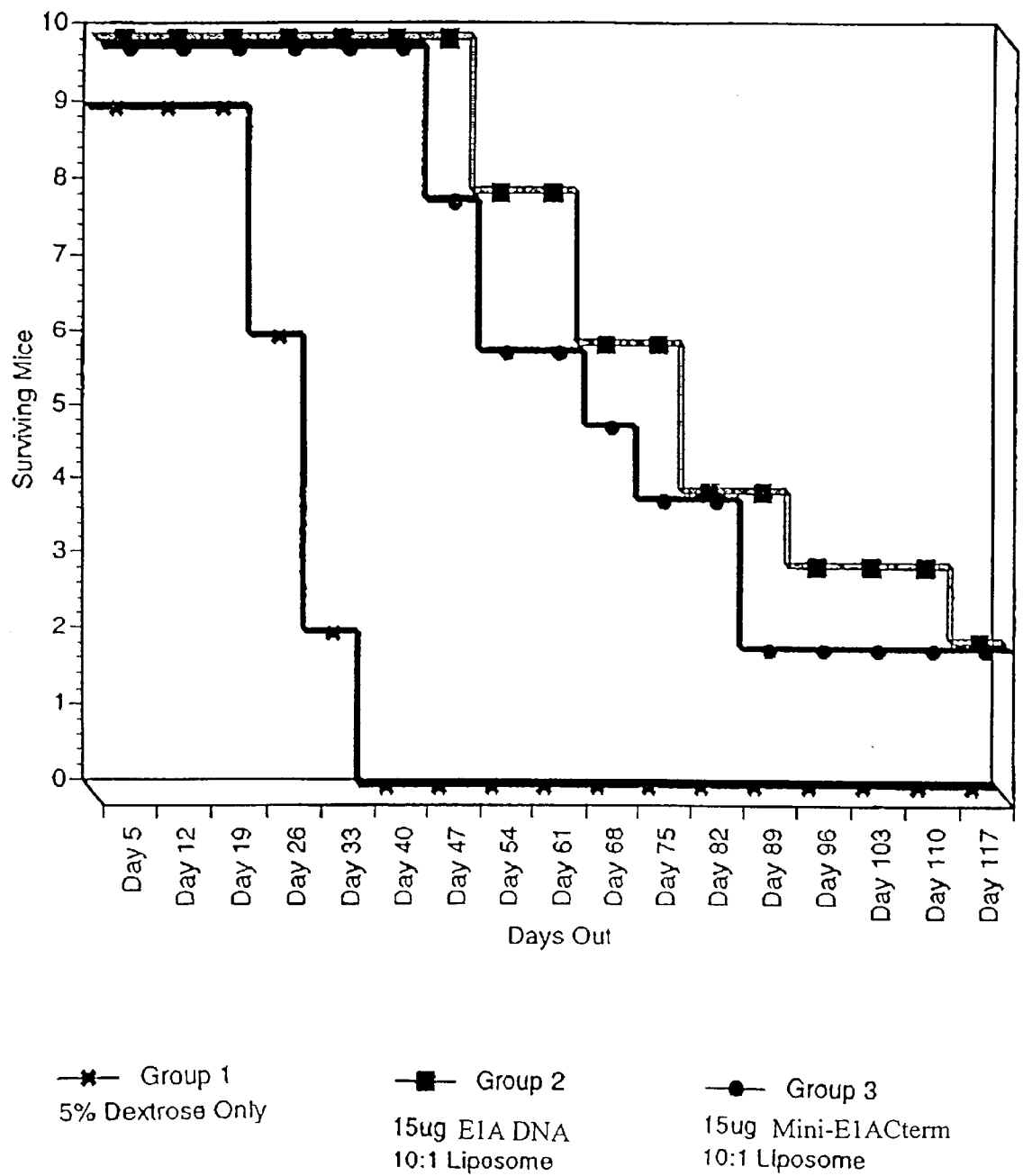
FIG. 9. Comparison of tumor suppressor activity of full-length E1A and mini-E1ACterm. Mice bearing tumors from an aggressive subclone of the SKOV-3.ip1 cell line were injected with the treatment compounds indicated.

The results, as shown in FIG. 9, revealed that mini-E1ACterm provides substantial tumor suppression and long-term survival to an extent similar to that of full-length E1A. Indeed, at the time when the last surviving mice that received dextrose injections died, 100% of the animals receiving mini-E1ACterm and full-length E1A were still alive. In addition, it should be noted that tumor cells in this experiment were very aggressive in that all 9 of the control mice had died by about day 35. At the time of death, the mice exhibited large tumor masses, clearly observable upon visual inspection. After 21 weeks, the 4 surviving mice that received either mini-E1ACterm or full-length E1A exhibited no signs of such tumor masses.

In this in vivo model, the portion of E1A provided by the mini-E1ACterm construct appears to be sufficient to provide substantial tumor suppression activity of E1A. Since the C-terminal segment that appears to contain tumor suppressing activity in this construct is only about 80 amino acids in length, it will be quite straightforward to delete and/or alter amino acids within this small segment in order to generate additional smaller E1A mini-genes containing the tumor suppressing domain.

EXAMPLE VI

HUMAN TREATMENT WITH TUMOR SUPPRESSING GENE PRODUCTS IN COMBINATION WITH ANTI-CANCER DRUGS OR ALONE

This example describes a protocol to facilitate the treatment of cancer using mini-E1A in combination with anti-cancer drugs and/or emodin like tyrosine kinase inhibitors. A patient presenting a cancer may be treated using the following protocol. Patients may, but need not, have received previous chemo- radio- or gene therapeutic treatments. Optimally the patient will exhibit adequate bone marrow function (defined as peripheral absolute granulocyte count of >2,000/mm3 and platelet count of 100,000/mm3, adequate liver function (bilirubin 1.5mg/dl) and adequate renal function (creatinine 1.5 mg/dl).

Monitoring neu Expression in Tumors

For tumors over-expressing neu, the levels of neu expression can be monitored before, during, and after the therapy. The following assay may be used to monitor neu expression. Sections of 3- to 4 mm thickness of the primary tumors and of the cell block preparations are cut, deparaffinized in xylene, and rehydrated in descending grades (100–70%) of ethanol. Endogenous peroxidase activity is blocked with 3% hydrogen peroxide in methanol. After several washes in distilled water and phosphate-buffered saline, the sections are incubated with a 1:10 dilution of normal horse serum to minimize background staining. This is followed by incubation for 1 hr at room temperature with the primary antibody (Ab-3 monoclonal antibody, Oncogene Sciences, Uniondale, N.Y.; 1:100). The peroxidase staining procedure utilizes ABC Elite Kits (Vector Laboratories, Burlingame, Calif.). The immunostaining reactions are visualized using 3-amino-9-ethylcarbazole as the chromogen. The sections and/or cytospin preparations are stained with toluidine blue and mounted in permount. Positive and negative control immunostains are also prepared.

The sections are reviewed by the pathologist. Two features of the immunoreaction will be recorded using a semi quantitative scale: the relative number of positive cells (0%, <10%, 10–50%, and >50%) and the intensity of the reaction (0–3). The pattern of immunostaining (membranous, cytoplasmic) is recorded separately. A tumor is considered neu positive if any neoplastic cells show cell membrane reactivity. Cytoplasmic staining is considered non-specific. A breast carcinoma known for its strong positive membrane staining will be used as a positive control. The quantitative measurement of neu immunostaining can be performed using computerized image analysis with the SAMBA 4000 Cell Image Analysis System (Image Products International, Inc., Chantilly, Va.) integrated with a Windows based software. A strong staining tumor tissue section will be used as positive control. The primary antibody will be replaced by an isotype-matched irrelevant antibody to set the negative control threshold, averaging the results from ten fields.

Prolocol for the Treatment of Cancer Using E1A Gene Products

A composition of the present invention is typically administered orally or parenterally in dosage unit formulations containing standard, well known non-toxic physiologically acceptable carriers, adjuvants, and vehicles as desired. The term parenteral as used herein includes subcutaneous injections, intravenous, intramuscular, intra-arterial injection, or infusion techniques. The mini-E1A and/or other tumor suppressing gene products may be delivered to the patient before, after or concurrently with the other anti-cancer agents. A typical treatment course may comprise about six doses delivered over a 7 to 21 day period. Upon election by the clinician the regimen may be continued six doses every three weeks or on a less frequent (monthly, bimonthly, quarterly etc.) basis. Of course, these are only exemplary times for treatment, and the skilled practitioner will readily recognize that many other time-courses are possible.

A major challenge in clinical oncology is that many tumor cells are resistant to chemotherapeutic treatment One goat of the inventors' efforts has been to find ways to improve the efficacy of chemotherapy. In the context of the present invention, mini-E1A can be combined with any of a number of conventional chemotherapeutic regimens.

To kill cancer cells using the methods and compositions described in the present invention, one will generally contact a target cell with mini-E1A and at least one chemotherapeutic agent (second agent), examples of which are described above. These compositions will be provided in a combined amount effective to kill or inhibit the proliferation of the cell. This process may involve contacting the cell with mini-E1A and the second agent at the same time. Alternatively, this process may involve contacting the cell with a single composition or pharmacological formulation that includes both agents or by contacting the cell with two distinct compositions or formulations at the same time, wherein one composition includes the mini-E1A and the other includes the second agent.

Alternatively, the mini-E1A administration may precede or follow the delivery of the second agent by intervals ranging from minutes to weeks. In embodiments where the mini-E1A and the second compound are applied separately, one would ensure that a significant period of time did not expire between the time of each delivery, such that the second agent and the mini-E1A would still be able to exert an advantageously combined effect on the cancer. In such instances, it is contemplated that one would contact the cell with both agents within about 6 hours to one week of each other and more preferably , within 24–72 hours of each other. In some situations however, it may be desirable to extend the time period for treatment significantly where several days (2, 3, 4, 5, 6, 7 or more) to several weeks (1, 2, 3, 4, 5, 6 , 7 or more) lapse between respective administrations.

Regional delivery of mini-E1A will be an efficient method for delivering a therapeutically effective dose to counteract the clinical disease. Likewise, the chemotherapy may be directed to a particular effected region. Alternatively systemic delivery of either, or both, agent may be appropriate. The therapeutic composition of the present invention is administered to the patient directly at the site of the tumor. This is in essence a topical treatment of the surface of the cancer. The volume of the composition should usually be sufficient to ensure that the entire surface of the tumor is contacted by the mini-E1A and second agent. In one embodiment, administration simply entails injection of the therapeutic composition into the tumor. In another embodiment, a catheter is inserted into the site of the tumor and the cavity may be continuously perfused for a desired period of time.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least 1 month with no tumor sites showing enlargement. Similarly, a mixed response may be defined by a reduction of the product of perpendicular diameters of all measurable lesions by 50% or greater with progression in one or more sites.

Of course, the above-described treatment regimes may be altered in accordance with the knowledge gained from clinical trials such as those described herein. Those of skill in the art will be able to take the information disclosed in this specification and optimize treatment regimes based on the clinical trials described in the specification.

EXAMPLE VII

CLINICAL TRIALS OF THE USE OF MINI-E1A IN COMBINATION WITH ANTI-CANCER DRUGS IN TREATING CANCER

This example is concerned with the development of human treatment protocols using the E1A and LT in combination with anti-cancer drugs. Mini-E1A and anti-cancer drug treatment will be of use in the clinical treatment of various cancers in which transformed or cancerous cells play a role. Such treatment will be particularly useful tools in anti-tumor therapy, for example, in treating patients with ovarian, breast and lung cancers that are resistant to conventional chemotherapeutic regimens.

The various elements of conducting a clinical trial, including patient treatment and, monitoring, will be known to those of skill in the art in light of the present disclosure. The following information is being presented as a general guideline for use in establishing mini-E1A in combinations with anti-cancer drugs and/or emodin-like tryosine kinase inhibitor in clinical trials.

Patients with advanced, metastatic breast, epithelial ovarian carcinoma or other cancers chosen for clinical study will typically have failed to respond to at least one course of conventional therapy. In an exemplary clinical protocol, patients may undergo placement of a Tenckhoff catheter, or other suitable device, in the pleural or peritoneal cavity and undergo serial sampling of pleural/peritoneal effusion. Typically, one will wish to determine the absence of known loculation of the pleural or peritoneal cavity, creatinine levels that are below 2 mg/dl, and bilirubin levels that are below 2 mg/dl. The patient should exhibit a normal coagulation profile.

In regard to the mini-E1A and other anti-cancer drug administration, a Tenckhoff catheter, or alternative device may be placed in the pleural cavity or in the peritoneal cavity, unless such a device is already in place from prior surgery. A sample of pleural or peritoneal fluid can be obtained, so that baseline cellularity, cytology, LDH, and appropriate markers in the fluid (CEA, CA15–3, CA 125, p185) and in the cells (E1A, p185) may be assessed and recorded.

In the same procedure, mini-E1A may be administered alone or in combination with the anti-cancer drug and/or emodin-like tyrosine kinase inhibitor. The administration may be in the pleural/peritoneal cavity, directly into the tumor, or in a systemic manner. The starting dose may be 0.5 mg/kg body weight. Three patients may be treated at each dose level in the absence of grade>3 toxicity. Dose escalation may be done by 100% increments (0.5 mg, 1 mg, 2 mg, 4 mg) until drug related grade 2 toxicity is detected. Thereafter dose escalation may proceed by 25% increments. The administered dose may be fractionated equally into two infusions, separated by six hours if the combined endotoxin levels determined for the lot of mini-E1A and the lot of anti-cancer drug exceed 5 EU/kg for any given patient.

The mini-E1A and anti-cancer drug and/or emodin-like tyrosine kinase inhibitor combination may be administered over a short infusion time or at a steady rate of infusion over a 7 to 21 day period. The mini-E1A infusion may be administered alone or in combination with the anti-cancer drug and/or emodin like tyrosine kinase inhibitor. The infusion given at any dose level will be dependent upon the toxicity achieved after each. Hence, if Grade II toxicity was reached after any single infusion, or at a particular period of time for a steady rate infusion, further doses should be withheld or the steady rate infusion stopped unless toxicity improved. Increasing doses of mini-E1A in combination with an anti-cancer drug will be administered to groups of patients until approximately 60% of patients show unacceptable Grade III or IV toxicity in any category. Doses that are 2/3 of this value could be defined as the safe dose.

Physical examination, tumor measurements, and laboratory tests should, of course, be performed before treatment and at intervals of about 3–4 weeks later. Laboratory studies should include CBC, differential and platelet count, urinalysis, SMA-12–100 (liver and renal function tests), coagulation profile, and any other appropriate chemistry studies to determine the extent of disease, or determine the cause of existing symptoms. Also appropriate biological markers in serum should be monitored e.g. CEA, CA 15–3, p185 for breast cancer, and CA 125, p185 for ovarian cancer.

To monitor disease course and evaluate the anti-tumor responses, it is contemplated that the patients should be examined for appropriate tumor markers every 4 weeks, if initially abnormal, with twice weekly CBC, differential and platelet count for the 4 weeks; then, if no myelosuppression has been observed, weekly. If any patient has prolonged myelosuppression, a bone marrow examination is advised to rule out the possibility of tumor invasion of the marrow as the cause of pancytopenia. Coagulation profile shall be obtained every 4 weeks. An SMA-12–100 shall be performed weekly. Pleural/peritoneal effusion may be sampled 72 hours after the first dose, weekly thereafter for the first two courses, then every 4 weeks until progression or off study. Cellularity, cytology, LDH, and appropriate markers in the fluid (CEA, CA15–3, CA 125, p185) and in the cells (p185) may be assessed. For an example of an evaluation profile, see Table 4. When measurable disease is present, tumor measurements are to be recorded every 4 weeks. Appropriate radiological studies should be repeated every 8 weeks to evaluate tumor response. Spirometry and DLCO may be repeated 4 and 8 weeks after initiation of therapy and at the time study participation ends. An urinalysis may be performed every 4 weeks.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least I month with no tumor sites showing enlargement. Similarly, a mixed response may be defined by a reduction of the product of perpendicular diameters of all measurable lesions by 50% or greater with progression in one or more sites.

TABLE 2

EVALUATIONS BEFORE AND DURING THERAPY

| EVALUATIONS | PRE-STUDY | TWICE WEEKLY | WEEK-LY | EVERY 4 WEEKS | EVERY 8 WEEKS |
|---|---|---|---|---|---|
| History | X | | | X | |
| Physical | X | | | X | |
| Tumor Measurements | X | | | X | |
| CBC | X | $X^1$ | X | | |
| Differential | X | $X^1$ | X | | |
| Platelet Count | X | $X^1$ | X | | |
| SMA12-100 (SGPT, Alkaline Phosphatase, Bilirubin, Alb/ Total Protein) | X | | X | | |
| Coagulation Profile | X | | | X | |
| Serum Tumor markers (CEA, CA15-3, CA-125, Her-2/neu) | X | | | $X^3$ | |
| Urinalysis | X | | | X | |
| X-rays: | | | | | |
| chest | X | | $X^4$ | | |
| others | X | | | | X |
| Pleural/Peritoneal Fluids: (cellularity, cytology, LDH, tumor markers, E1A, HER-2/neu) | X | | $X^5$ | X | |
| Spirometry and DLCO | X | | | $X^6$ | $X^6$ |

[1]For the first 4 weeks, then weekly, if no myelosuppression is observed.
[2]As indicated by the patient's condition.
[3]Repeated every 4 weeks if initially abnormal.
[4]For patients with pleural effusion, chest X-rays may be performed at 72 hours after first dose, then prior to each treatment administration.
[5]Fluids may be assessed 72 hours after the first dose, weekly for the first two courses and then every 4 weeks thereafter.
[6]Four and eight weeks after initiation of therapy.

While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the invention. More specifically, it will be apparent that certain agents which are both chemically and physically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adelman et al. (1983)DNA2:183
Alberts et al, *Clin. Pharmacol. Ther.*, 86:737–745, 1979.
Alley et al. (1988) *Cancer Res.*, 48:589.
Ayash, et al., *J Clin Oncol*, 12:37–44, 1994.
Baichwal and Sugden, In: Kucherlapati R, ed. *Gene Transfer*. New York: Plenum Press, pp. 117–148, 1986.
Bargmann, C. I., et al., *Nature* (Lond.), 319: 226–230, 1986a.

Bargmann, C. I., et al., *Cell*, 45: 649–657, 1986b.
Benvenisty et al., (1986), *Proc Natl Acad Sci USA* 83:9551–9555.
Berk et al, (1978), *Cell*, 14:695.
Berchuck, A., et al., *Cancer Res*, 50: 4087–4091, 1990.
Berns, Virology, pp. 1743–1764 (Raven Press 1990)
Campisi et al. (1983), *Cell*, 33:357.
Carter, B., Handbook of Parvoviruses, vol. 1, pp. 169–228, 1990.
Carter, B., Curr. Opin. Biotechnol., 3: 533–539, 1992.
Chan et al., *Biochem. Biophys. Res. Commun.*, 193:1152–1158, 1993.
Chang, L. S., et al, *J. Virol.*, 63: 3479–3488, 1989.
Chatterjee et al., *Ann. NY Acad. Sci.*, 770: 79–90, 1995.
Chen and Okayama, *Mol. Cell Biol.*, 7:2745–2752, 1987.
Chen, C. A., and Okayama, H. *BioTechniques*, 6: 632–638, 1988.
Chen, H. et al, *Oncogene*, 14:1965–1971, 1997.
Chen, H. and M.-C. Hung, *J. Biol. Chem.*, 272: 6101–6104, 1997.
Cherington et al. (1988), *Mol. Cell. Biol.*, 8:1380–1384.
Chinnadurai, G. *Oncogene* 7: 1255–1258, 1992.
Coffin, In: Virology, Fields et al (eds.), New York: Raven Press, pp. 1437–1500, 1990.
Cook et al (1989), *J. Immunol*, 142:4527–4534.
Cook & Lewis (1984), *Science*, 224:612–615.
Corbeil, H. B., and Branton, P. E. *J. Virol.*, 68: 6697–6709, 1994.
Couch et al, *Am. Rev. Resp. Dis.*, 88:394–403, 1963.
Coupar et al., *Gene*, 68:1–10, 1988.
Crea et al. (1978), *Proc. Natl. Acad. Sci. U.S.A* 75:5765
D'Emilia, et al *Oncogene*, 4: 1233–1239, 1989.
DeCaprio et al. (1988), 54:275–283.
Dobashi et al. (1991), *Proc. Natl. Acad. Sci. USA*, 88:8582–8586.
Dougall, et al, *Oncogene*, 9: 2109–2123, 1994.
Downward et al. (1984), *Nature* (London), 307:521.
Du et al., *Gene Therapy* 3: 254261, 1996.
Dubensky et al.,*Proc. Nat'l Acad. Sci. USA*, 81:7529–7533, 1984.
Dynlacht et al. (1991), *Cell*, 66:563–576.
Edlund, T., et al,. *Science* (Washington D.C.), 230: 912–916, 1985.
Eichenlaub, R. (1979), *J. Bacteriol* 138:559–566
Evan et al (1992), *Cell*, 69:119–128.
Fechheimer et al., *Proc. Nat'l Acad. Sci. USA*, 84:8463–8467, 1987.
Ferkol et al., *FASEB J.*, 7:1081–1091, 1993.
Fiers et al. (1978), *Nature* 273:113.
Figge et al. (1988), *J. Virol*, 62:1814–1818.
Flint, J., and Shenk, T. *Annu. Rev. Genet.*, 23: 141–161, 1989.
Flotte, T. R., et al., *Am. J. Respir. Cell Mol. Biol.* 7:349–356, 1992.
Flotte, T. R., et al., *Gene Therapy* 2:357–362, 1995.
Fraley et al., *Proc. Nat't Acad. Sci. USA*, 76:3348–3352, 1979.
Friedmann, "Progress toward human gene therapy," *Science*, 244:1275–1281, 1989.

Frisch, S. M., *Proc. Natl. Acad. Sci. USA*, 88:9077–9081, 1991.
Frisch, S. M. and H. Francis, *J. Cell. Biol.*, 124: 619–626, 1994.
Frisch, S.M., *J. Cell. Biol.*, 127: 1085–1096, 1994.
Frisch, S.M., et al., Cancer Res., 55:5551–5555, 1995.
Gao et al., (1991), *Biochemical and Biophysical Research Communications*, 179(1):280–285.
Ghalie, et al., *J Clin Oncol*, 12:342–6, 1994.
Ghosh and Bachhawat, In: Wu G. and C. Wu eds. *Liver diseases, targeted diagnosis and therapy using specific receptors and ligands*. New York: Marcel Dekker, pp. 87–104, 1991.
Gomez-Foix et al., *J. Biol. Chem.*, 267:25129–25134, 1992.
Gopal, *Mol. Cell. Biol.*, 5:1188–1190, 1985.
Gorman, C., et al., *Mol. Cell. Biol.*, 2: 1044–1051, 1982.
Graham and Prevec, *Biotechnology*, 20:363–390, 1992.
Graham and van der Eb, *Virology*, 52:456–467, 1973.
Gribskov et al. (1986), *Nucl. Acids Res.*, 14:6745.
Grunhaus and Horwitz, Seminar in Virology, 3:237–252, 1992.
Gusterson, et al., *J Clin Oncol*, 10: 1049–56, 1992.
Haley et al. (1984), *Proc. Natl. Acad. Sci. USA*, 81:5734.
Harland and Weintraub, *J. Cell Biol.*, 101:1094–1099, 1985.
Harlow et al. (1985), *J. Virol.*, 55:533.
Hearing et al. (1985), *Mol. Cell. Biol.*, 5:3214.
Hen et al. (1985), *Science*, 230:1391.
Hermonat and Muzycska, *Proc. Nat'l Acad. Sci. USA*, 81:6466–6470,1984.
Hersdorffer et al., *DNA Cell Biol.*, 9:713–723, 1990.
Herz and Gerard, *Proc. Nat'l Acad. Sci. USA* 90:2812–2816, 1993.
Holmes et al. (1992), *Science*, 256:1205–1210.
Horikoshi, N., et al., *Mol. Cell. Biol.*, 15: 227–234, 1995.
Horwich et al., *J. Virol.*, 64:642–650, 1990.
Houweling et al. (1980), *Virology*, 105:537.
Huang & Huang, (1992), *J. Biol. Chem.*, 267:11508–11512.
Hung, M. C., et al., *Proc. Natl. Acad. Sci. USA*, 86:2545–2548, 1989.
Hung, M. C., et al., *Gene*, 159:65–71, 1995.
Hung, M. C., et al., *Cancer Lett.*, 61: 95–103, 1992.
Hung, M. C., et al.,*Proc Natl Acad Sci USA*, 83: 261–264, 1986.
Hung, M. C., et al, *Proc Natl Acad Sci USA*, 86: 2545–2548, 1989.
Jayasuriya et al., *J. Nat. Prod.*, 55:696–698, 1992.
Jelsma, T. N., et al., *Virology*, 163: 494–502, 1988.
Jelsma, T. N., et al., *Virology*, 171: 120–130, 1989.
Johnson et al. (1988), *J. Biol. Chem.*, 263:5693–5699.
Kalderon etal.,. (1984), *Virology*, 139:109–137.
Kaneda et al., *Science*, 243:375–378, 1989.
Karlsson et al., *EMBO J.*, 5:2377–2385, 1986.
Kato et al., *J. Biol. Chem.*, 266:3361–3364, 1991.
Katsumata et al., *Nature Med.*, 1: 644–648. 1995
Klein et al., *Nature*, 327:70–73, 1987.
Kotin, R., Human Gene Therapy, 5: 793–801, 1994.

Kraus et al. (1987), *EMBO J.*, 6:605.
Kuppuswamy, M., and Chinnadurai, G. *Virology*, 159: 31–38, 1987.
Kyte & Doolittle, *J. Mol. Biol.*, 157:105–132, 1982.
Land et al., (1983), *Science*, 222:771.
Le Gal La Salle et al., *Science*, 259:988–990, 1993.
Levrero et al., *Gene*, 10 1: 195–202, 199 1.
Lillie, J. W., et al., *Cell*, 46: 1043–1051, 1986.
Liu, F., and Green, M. R. *Nature* (Lond.), 368: 520–525, 1994.
Livingston et al. (1987), *Mol. Biol. Med.*, 4:63–80.
Lupu et al., (1990), *Science*, 249:1552.
Mann et al., *Cell*, 33:153–159, 1983.
Markowitz et al., *J. Virol.*, 62:1120–1124, 1988.
Matin et al. (1989), *Oncogene*, 5:111.
McCann, et al., *Cancer Res*, 51:3296–303, 1991.
Messing et al., (1981) *Third Cleveland Symposium on Macromolecules and Recombinant DNA*, Editor A. Walton, Elsevier, Amsterdam
Mitchell et al. (1989), *Science*, 245:371.
Moran et al. (1987), *Cell*, 48:177.
Moran, E., et al., *J. Virol.*, 57: 765–775, 1986.
Muller et al. (1982), *Nature* (London), 299:640.
Muller, W. J., et al., *Cell*, 54: 105–115, 1988.
Muro-cacho, C. A., et al., (1992), *J. of Immunotherapy*, 11:231–237.
Muss, et al., *N. Engl J Med*, 330:1260–6, 1994.
Muzyczka, N., Current Topics in Microbiology and Immunology, 158: 92–129, 1992.
Mymryk, (1996), *Oncogene* 13:1–9.
Nabel et al. (1990), *Science*, 249:1285–1288.
Needleman et al. (1970), *J. Mol. Biol.*, 48:443.
Nelson et al. (1990), *Proc. Natl. Acad. Sci. USA*, 87:8041–8045.
Nicolas & Rubenstein, In: *Vectors: A survey of molecular cloning vectors and their uses*, Rodriguez & Denhardt (eds.), Stoneham: Butterworth, pp. 493–513, 1988.
Nicolau and Sene, *Biochem. Biophys. Acta*, 721:185–190, 1982.
Nicolau et al. (1987), *Methods in Enzymology*, 149:157–176.
Norton, P. A., and Coffin, J. M. *Mol. Cell. Biol.*, 5: 281–290, 1985.
Padhy, L. C., et al., *Cell*, 28: 865–871, 1982.
Park, J. B., et al., *Cancer Res.*, 49: 6605–6609, 1989.
Paskind et al., *Virology*, 67:242–248, 1975.
Peles et al. (1992), *Cell*, 69:205–216.
Perales et al., *Proc. Natl. Acad. Sci. USA*, 91:4086–4090, 1994.
Peters, et al., *J Clin Oncol*, 11:1132–43, 1993.
Potter et at, "*Proc. Nat'l Acad. Sci. USA*, 81:7161–7165, 1984.
Pozzatti et al. (1988), *Mol. Cell. Biol.*, 8:2984.
Ragot et al., *Nature*, 361:647–650, 1993.
Rao et al., (1992), *Proc. Natl. Acad. Sci. USA*, 89:7742–7746.
Reddy et al. (1978), *Science*, 200:494.
Rich et al., *Hum. Gene Ther.*, 4:461476,1993.
Ridgeway, In: Rodriguez R L, Denhardt D T, ed. Vectors: *A survey of molecular cloning vectors and their uses.* Stoneham: Butterworth, pp. 467–492, 1988.

Rippe et al., *Mol. Cell Biol.*, 10:689–695, 1990.
Robert et al (1985), *J. Virol*, 56:404.
Rosenfeld et al., *Cell*, 68:143–155, 1992.
Rosenfeld et al., *Science*, 252:431–434, 1991.
Roux et al, *Proc. Natl. Acad. Sci. USA*, 86:9079–9083, 1989.
Ruley, H. E. (1985), *Nature*(London), 304:602.
Rustgi et al. (1991), *Nature*, 352:541–544.
Sawada et al. (1985), *Virology*, 147:413–421.
Saya, H., et al., 3: 198–201, 1990.
Schechter et al., *Nature*, 312:513–516, 1984.
Schneider, J. F et al., *EMBO J.*, 6: 2053–2060, 1987.
Schneider, P. M., et al., *Cancer Res.*, 49: 4968–4971, 1989.
Schwartz et al., eds. (1979), *Atlas of protein Sequence and*
Senba et al. (1985), *Proc. Natl. Acad. Sci. USA*, 82:6497.
Shi, D., et al., *Mol. Carcinog.*, 5: 213–218, 1992.
Shih et al. (1981), *Nature* (London), 290:261–264.
Slamon, D. J., et al., *Science* (Washington D.C.), 244: 707–712, 1989.
Slamon, et al., *Science*, 240:177–182, 1987.
Smith and Rutledge, "Chemotherapy in advanced ovarian cancer," *Natl. Cancer Inst. Monogr.*, 42:141–143, 1975.
Smith et al. (1981), *Adv. Appl. Math.*, 2:482.
Smith, D. H., and Ziff, E. *Mol. Cell. Biol.*, 8: 3882–3890, 1988.
Southern et al. (1982), *J. Mol. Appl. Genet.*, 1:327.
Steeg et al. (1988), *Cancer Res.*, 48:6550–6554.
Stein et al. (1987), *Mol. Cell. Biol.*, 7:1164.
Stratford-Perricaudet and Perricaudet. 51–61, In: *Human Gene Transfer, Eds,* O. Cohen-Haguenauer and M. Boiron, Editions John Libbey Eurotext, France, 1991.
Stratford-Perricaudet et al., *Hum. Gene Ther.*, 1:241–256, 1990.
*Structure*, National Biomedical Research Foundation, pgs. 353–358.
Suen, T. C., and Hung, M. C. *Mol. Cell. Biol.*, 10: 6306–6315, 1990.
Tal., et al. (1987), *Mol. Cell. Biol.*, 7:2597.
Temin, In: *Gene Transfer, Kucherlapati (ed.)*, New York: Plenum Press, pp. 149–188, 1986.
Toikkanen, et al., *J Clin Onc*, 10:1044–48, 1992.
Tooze, J. (1981), *Molecular Biology of Tumor Viruses*, Part 2, 2d ed. Cold Spring Harbor Laboratory, Cold Spring Harbor, N.Y.
Top et al., *J. Infect. Dis.*, 124:155–160, 1971.
Towbin et al. (1979), *Proc. Natl. Acad. Sci., USA*, 76:4350.
Tsai, et al., *J Natl. Cancer Inst*, 87:6824, 1995.
Tur-Kaspa et al., *Mol. Cell Biol.*, 6:716–718, 1986.
Van Dam et al. (1989), *Oncogene*, 4:1207.
Van, d. V. M., et al., *Mol. Cell. Biol.*, 7: 2019–2023, 1987.
Varmus et al., *Cell*, 25:23–36, 1981.
Velcich et al. (1986), *Mol. Cell. Biol.*, 6:4019.
Vijver, et al., *Mol. Cell. Biol.*, 7:2019–23, 1987.
Wagner et al., *Science*, 260:1510–1513, 1990.
Wallich et al. (1985), *Nature* (London), 315:301.
Wang et al. (1991), *Mol. Cell. Biol.*, 11:4253–4265.

Weinberg, R. A. (1985), *Science*, 230:770–776.
Weiner, D. B., et al., *Cancer Res.*, 50: 421–425, 1990.
Whyte et al. (1988), *Nature* (London), 334:124–129.
Whyte, P., et al., *Cell*, 56: 67–75, 1989.
Wu and Wu, *Biochemistry*, 27:887–892, 1988.
Wu and Wu, *J. Biol Chem.*, 262:4429–4432, 1987.
Yan, et al., *Oncogene*, 6:343–345, 1991.
Yanisch-Perron et al. (1985), *Gene*, 33:103–109.
Yarden & Peles (1991), *Biochemistry*, 30:3543–3550.
Yeh et al, *Planta Med.*, 54:413–414, 1988.
Yokota, J., et al., *Oncogene*, 2: 283–287, 1988.
Young et al., *N. Engl. J. Med.*, 299:1261–1266, 1978
Yu, D. and Hung, M. C. *Oncogene*, 6: 1991–1996, 1991.
Yu, D. and Hung, M. C., pp. 131–162 in "Molecular Basis of Oncology" (Freireich and Stass, eds.), Blackwell Science, 1995.
Yu, D., et al., *Cancer Res.*, 53: 891–898, 1993.
Yu, D., et al., *Cancer Res.*, 54: 3260–3266, 1994.
Yu, D., et al., *J. Biol Chem.*, 267: 10203–10206, 1992b.
Yu, D., et al., *Oncogene*, 7: 2263–2270, 1992a.
Yu, D., et al., *Proc Natl Acad Sci USA*, 87:4499–503, 1990.
Yu, D., et al., *Oncogene*, 11: 1383–1388, 1995.
Zelenin et al., *FEBS Lett.*, 280:94–96, 1991.
Zerler, B., et al., *Mol. Cell. Biol.*, 6: 887–899, 1986.
Zerler, B., et al, *Mol. Cell Biol.*, 7: 821–829, 1987.
Zhang et al. (1989), *Oncogene*, 4:985–989.
Zhang, Y., et al., *Oncogene*, 10: 1947–1954, 1995.

What is claimed is:

1. A nucleic acid encoding a mini-E1A gene product, wherein said mini-E1A gene product comprises a C-terminal segment of E1A located within exon 2 of E1A and lacking at least a 25 amino acid portion of the N-terminal segment of E1A.

2. The nucleic acid segment of claim 1, wherein the mini-E1A gene product is an E1A gene product from which the CR1 region has been removed.

3. The nucleic acid segment of claim 1, wherein the mini-E1A gene product is an E1A gene product from which both the CR1 and CR2 regions have been removed.

4. The nucleic acid segment of claim 1, wherein the mini-E1A gene product is lacking all but about 80 amino acids from the C-terminus of E1A.

5. The nucleic acid segment of claim 1, wherein the mini-E1A gene product is lacking all but a tumor suppression domain found within the C-terminal 80 amino acids of E1A.

6. The nucleic acid segment of claim 1, wherein the mini-E1A gene product comprises an amino-terminal segment having the amino acid sequence found between about amino acid 4 and about amino acid 25 of an E1A gene product.

7. The nucleic acid segment of claim 1, wherein the mini-E1A gene product comprises an amino-terminal segment having the amino acid sequence found between about amino acid 40 and about amino acid 80 of an E1A gene product.

8. The nucleic acid segment of claim 7, wherein the mini-E1A gene product further comprises a spacer at the C-terminal end of CR1 domain of an E1A gene product.

9. The nucleic acid segment of claim 8, wherein the spacer comprises an amino acid segment having the amino acid sequence found between about amino acid 81 and about amino acid 101 of an E1A gene product.

10. The nucleic acid segment of claim 1, wherein the mini-E1A gene product has tumor suppression activity.

11. The nucleic acid segment of claim 1, wherein the mini-E1A gene product has neu repression activity.

12. The nucleic acid segment of claim 1, further defined as comprising a vector.

13. The nucleic acid segment of claim 1, further defined as complexed in a non-viral gene delivery complex.

14. A vector comprising a nucleic acid segment of a mini-E1A gene product, wherein said mini-E1A gene product comprises a C-terminal segment of E1A located within exon 2 of E1A and lacking at least a 25 amino acid portion of the N-terminal segment of E1A.

15. The vector of claim 14, wherein the vector is a plasmid.

16. The vector of claim 14, wherein the vector is a viral vector.

17. The vector of claim 16, wherein the viral vector is selected from the group consisting of an adenoviral vector, and adeno-associated viral vector and a retroviral vector.

18. The vector of claim 16, wherein the viral vector is a replication-deficient adenoviral vector.

19. A mammalian cell comprising a nucleic acid vector encoding a mini-E1A gene product, wherein said mini-E1A gene product comprises a C-terminal segment of E1A located within exon 2 of E1A and lacks at least a 25 amino acid portion of the N-terminal segment of E1A.

20. A non-viral gene delivery complex comprising a nucleic acid segment of a mini-E1A gene product, wherein said mini-E1A gene product comprises a C-terminal segment of E1A located within exon 2 of E1A and lacking at least a 25 amino acid portion of the N-terminal segment of E1A.

21. The non-virene delivery complex of claim 20, wherein the complex is a lipid-DNA complex.

22. The non-viral gene delivery complex of claim 21 further comprising a DNA condensation agent.

23. The non-viral gene delivery complex of claim 21, comprising a lipid selected from the group consisting of DOTMA, DOPE and DC-Chol.

24. The non-viral gene delivery complex of claim 21, comprising DC-Chol.

25. The non-viral gene delivery complex of claim 21, comprising protamine sulfate.

26. The non-viral gene delivery complex of claim 20, wherein the complex comprises a lipid, a polycation, and a polynucleotide encoding a mini-E1A gene product.

27. The non-viral gene delivery complex of claim 26, wherein the polycation is selected from the group consisting of a protamine, a polyarginine, a polyornithine, a polylysine, a polybrene, a spermine, a spermidine, a histone, and a cationic dendrimer.

28. A composition suitable for administration to an individual comprising a pharmaceutically acceptable carrier and a nucleic acid encoding a mini-E1A gene product, wherein the mini-E1A gene product comprises a C-terminal segment of E1A located within exon 2 of E1A and lacks at least a 25 amino acid portion of the N-terminal segment of E1A, and a pharmaceutically acceptable carrier.

* * * * *

UNITED STATES PATENT AND TRADEMARK OFFICE
CERTIFICATE OF CORRECTION

PATENT NO.   : 6,683,059 B1
DATED        : January 27, 2004
INVENTOR(S)  : Hung et al.

It is certified that error appears in the above-identified patent and that said Letters Patent is hereby corrected as shown below:

Title page,
Item [54], Title, delete "MINI-E1A GENE AND GENE PRODUCTS" and insert
-- NUCLEIC ACIDS ENCODING A MINI-E1A GENE PRODUCT --
Item [75], Inventors, delete "Ralph Wilfred Paul, Seattle, WA (US); Aaron Garth Loomis, Seattle, WA (US); Daniel Nathan Andrew LaFoc, Seattle, WA (US)".

Column 58,
Line 24, delete "A" and insert -- An isolated -- therefor.

Signed and Sealed this

Fourth Day of May, 2004

JON W. DUDAS
*Acting Director of the United States Patent and Trademark Office*

SEQUENCE LISTING

<160> NUMBER OF SEQ ID NOS: 2

<210> SEQ ID NO 1
<211> LENGTH: 315
<212> TYPE: DNA
<213> ORGANISM: Artificial Sequence
<220> FEATURE:
<223> OTHER INFORMATION: Description of Artificial Sequence: Synthetic Primer
<221> NAME/KEY: CDS
<222> LOCATION: (70)..(312)

<400> SEQUENCE: 1

```
cctgtgtctg aacctgagcc tgagcccgag ccagaaccgg agcctgcaag acctacccgc      60 cgtcctaaa atg gcg cct gct atc ctg aga cgc ccg aca tca cct gtg tct     111
           Met Ala Pro Ala Ile Leu Arg Arg Pro Thr Ser Pro Val Ser
             1               5                  10 aga gaa tgc aat agt agt acg gat agc gtg gac tcc ggt cct tct aac       159
Arg Glu Cys Asn Ser Ser Thr Asp Ser Val Asp Ser Gly Pro Ser Asn
 15                  20                  25                  30 aca cct cct gag aga cac ccg gtg gtc ccg ctg tgc ccc att aaa cca       207
Thr Pro Pro Glu Arg His Pro Val Val Pro Leu Cys Pro Ile Lys Pro
                 35                  40                  45 gtt gcc gtg aga gtt ggt ggg cgt cgc cag gct gtg gaa tgt atc gag       255
Val Ala Val Arg Val Gly Gly Arg Arg Gln Ala Val Glu Cys Ile Glu
             50                  55                  60 gac ttg ctt aac gag cct ggg caa cct ttg gac ttg agc tgt aaa cgc       303
Asp Leu Leu Asn Glu Pro Gly Gln Pro Leu Asp Leu Ser Cys Lys Arg
         65                  70                  75 ccc agg cca taa                                                        315
Pro Arg Pro
     80
```

<210> SEQ ID NO 2
<211> LENGTH: 81
<212> TYPE: PRT
<213> ORGANISM: Artificial Sequence
<220> FEATURE:
<223> OTHER INFORMATION: Description of Artificial Sequence: Synthetic Primer

<400> SEQUENCE: 2

```
Met Ala Pro Ala Ile Leu Arg Arg Pro Thr Ser Pro Val Ser Arg Glu
  1               5                  10                  15

Cys Asn Ser Ser Thr Asp Ser Val Asp Ser Gly Pro Ser Asn Thr Pro
             20                  25                  30
```

-continued

```
Pro Glu Arg His Pro Val Val Pro Leu Cys Pro Ile Lys Pro Val Ala
         35                  40                  45

Val Arg Val Gly Gly Arg Arg Gln Ala Val Glu Cys Ile Glu Asp Leu
     50                  55                  60

Leu Asn Glu Pro Gly Gln Pro Leu Asp Leu Ser Cys Lys Arg Pro Arg
 65                  70                  75                  80

Pro
```